(12) United States Patent
Sadelain et al.

(10) Patent No.: US 12,036,244 B2
(45) Date of Patent: Jul. 16, 2024

(54) CELLS COMPRISING NON-HLA RESTRICTED T CELL RECEPTORS

(71) Applicant: MEMORIAL SLOAN-KETTERING CANCER CENTER, New York, NY (US)

(72) Inventors: Michel Sadelain, New York, NY (US); Jorge A. Mansilla-Soto, Forest Hills, NY (US); Justin Eyquem, New York, NY (US); Anton Dobrin, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 17/505,515

(22) Filed: Oct. 19, 2021

(65) Prior Publication Data

US 2022/0031754 A1 Feb. 3, 2022

Related U.S. Application Data

(63) Continuation of application No. 16/990,185, filed on Aug. 11, 2020, which is a continuation of application No. PCT/US2019/017525, filed on Feb. 11, 2019.

(60) Provisional application No. 62/629,072, filed on Feb. 11, 2018.

(51) Int. Cl.
*C07K 14/725* (2006.01)
*A61K 35/17* (2015.01)
*C07K 16/28* (2006.01)

(52) U.S. Cl.
CPC .......... *A61K 35/17* (2013.01); *C07K 14/7051* (2013.01); *C07K 16/2803* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,956,778 A | 9/1990 | Naito | |
| 5,091,513 A | 2/1992 | Huston et al. | |
| 5,132,405 A | 7/1992 | Huston et al. | |
| 5,399,346 A | 3/1995 | Anderson et al. | |
| 5,843,728 A | 12/1998 | Seed et al. | |
| 5,912,172 A * | 6/1999 | Eshhar | C07K 16/44 424/134.1 |
| 7,446,190 B2 | 11/2008 | Sadelain et al. | |
| 2002/0018783 A1 | 2/2002 | Sadelain et al. | |
| 2005/0196754 A1 | 9/2005 | Drmanac et al. | |
| 2015/0313978 A1 | 11/2015 | Schadendorf et al. | |
| 2015/0337042 A1 | 11/2015 | Reilly et al. | |
| 2017/0173080 A1 | 6/2017 | Lee et al. | |
| 2017/0312350 A1 | 11/2017 | Maurer et al. | |
| 2017/0335010 A1 | 11/2017 | Jantz et al. | |
| 2018/0230224 A1 * | 8/2018 | Alvarez Rodriguez | C07K 16/2875 |
| 2018/0230429 A1 * | 8/2018 | Baeuerle | C12N 5/0638 |
| 2018/0282389 A1 | 10/2018 | Sahin et al. | |
| 2018/0291079 A1 | 10/2018 | Smith et al. | |
| 2018/0353588 A1 | 12/2018 | Boyd et al. | |
| 2018/0360883 A1 | 12/2018 | Galetto et al. | |
| 2018/0362926 A1 | 12/2018 | Conway et al. | |
| 2019/0055318 A1 | 2/2019 | Yankee et al. | |
| 2020/0368283 A1 | 11/2020 | Sadelain et al. | |

FOREIGN PATENT DOCUMENTS

| | | | |
|---|---|---|---|
| RU | 2 644 243 C2 | 2/2018 | |
| WO | WO 2014/055668 A1 | 4/2014 | |
| WO | WO 2014/091034 A1 | 6/2014 | |
| WO | WO 2019/157454 A1 | 6/2014 | |
| WO | WO 2016/187349 A1 | 11/2016 | |
| WO | WO-2017180989 A2 * | 10/2017 | A61K 35/17 |
| WO | WO 2017/192536 A1 | 11/2017 | |

OTHER PUBLICATIONS

Caruoso et al. (Cancer Res. Sep. 1, 2015; 75(17): 3505-3518). (Year: 2015).*
Hamieh et al. (Nature. Apr. 2019;568(7750):112-116). (Year: 2019).*
Song et al. (Journal of Hematology & Oncology (2016) 9:56). (Year: 2016).*
Ryan et al. (British Journal of Cancer (2010) 103, 676-684). (Year: 2010).*
Sandberg et al., Proc Natl Acad Sci U S A. Feb. 8, 2005;102(6):2052-7. (Year: 2005).*
Robert Weinberg, the Biology of Cancer, 2007, pp. 536-539. (Year: 2007).*
McKinney, J Neurol Neurosurg Psychiatry 2004;75(Suppl II):ii12-ii17. (Year: 2004).*
Lamberts et al. (Oncotarget. Sep. 29, 2015;6(29):28164-72). (Year: 2015).*
Hassan et al. (J Clin Oncol 34:4171-4179 (2016)). (Year: 2016).*
Chowdhury et al. (Nature biotechnology, 17(6), 568-572 (1999)). (Year: 1999).*
Hassan et al. (Cancer immunity, 7, 20 (2007)). (Year: 2007).*
Legut et al. (Blood. 2018;131(3):311-322). (Year: 2018).*
Natarajan et al., Cell Reports 14, 2833-2845, 2016. (Year: 2016).*
Birnbaum et al., Proc Natl Acad Sci U S A. 2014;111(49):17576-17581. (Year: 2014).*

(Continued)

*Primary Examiner* — Zachary S Skelding
(74) *Attorney, Agent, or Firm* — Baker Botts L.L.P.

(57) ABSTRACT

The presently disclosed subject matter provides methods and compositions for enhancing the immune response toward cancers and pathogens. It relates to novel designs of T cell receptors (TCRs) and engineered immunoresponsive cells comprising the same. The novel TCR binds to an antigen in an HLA-independent manner. In certain embodiments, the novel TCR provides enhanced sensitivity for a target gene having a low expression level.

21 Claims, 16 Drawing Sheets

Specification includes a Sequence Listing.

(56) References Cited

OTHER PUBLICATIONS

U.S. Appl. No. 16/990,185 (US 2020-0368283 A1) filed Aug. 11, 2020 (Nov. 26, 2020).
U.S. Appl. No. 17/075,142 (US 2021-0030804 A1) filed Oct. 20, 2020 (Feb. 4, 2021).
U.S. Appl. No. 17/075,142, Corrected Notice of Allowability Oct. 13, 2021.
U.S. Appl. No. 17/075,142, Notice of Allowance Sep. 30, 2021.
U.S. Appl. No. 17/075,142, Response to Non-Final Office Action Sep. 21, 2021.
U.S. Appl. No. 17/075,142, Non-Final Office Action Jun. 21, 2021.
U.S. Appl. No. 17/075,142, Amendment with Request for Continued Examination (RCE) Jun. 11, 2021.
U.S. Appl. No. 17/075,142, Final Office Action Apr. 2, 2021.
U.S. Appl. No. 17/075,142, Response to Non-Final Office Action Mar. 22, 2021.
U.S. Appl. No. 17/075,142, Non-Final Office Action Dec. 22, 2020.
Altschul et al., "Basic Local Alignment Search Tool," J. Mol. Biol. 215:403-410 (1990).
Altschul et al., "Gapped BLAST and PSI-BLAST: a new generation of protein database search programs," Nucleic Acids Res. 25(17):3389-3402 (1997).
Anderson, "Prospects for Human Gene Therapy," Science 226:401-409 (1984).
Attaf et al., "The T cell antigen receptor: the Swiss army knife of the immune system," Clinical and Experimental Immunology, 181:1-18 (2015).
Bannas et al., "Nanobodies and Nanobody-Based Human Heavy Chain Antibodies as Antitumor Therapeutics," Front Immunol. 8:1603 (1-13) (2017).
Benton et al., "Screening λgt Recombinant Clones by Hybridization to Single Plaques in situ," Science 196(4286):180-182 (1977).
Berry et al., "Modular Activating Receptors in Innate and Adaptive Immunity," Biochemistry 56:1383-1402 (2017).
Blomer et al., "Highly Efficient and Sustained Gene Transfer in Adult Neurons with a Lentivirus Vector," Journal of Virology 71:6641-6649 (1997).
Bregni, et al., "Human Peripheral Blood Hematopoietic Progenitors Are Optimal Targets of Retroviral-Mediated Gene Transfer," Blood 80(6):1418-1422 (1992).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Brocks et al., "A TNF receptor antagonistic scFv, which is not secreted in mammalian cells, is expressed as a soluble mono- and bivalent scFv derivative in insect cells," Immunotechnology 3:173-184 (1997).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Chang et al., "Rewiring T-cell responses to soluble factors with chimeric antigen receptors," Nat Chem Biol. 14(3):317-324 (2018).
Chmielewski et al., "Antigen-specific T-cell activation independently of the MHC: chimeric antigen receptor-redirected T cells," Frontiers in Immunology 4(371):7 pages (2013).
Cornetta et al., "Gene Transfer into Primates and Prospects for Gene Therapy in Humans," Nucleic Acid Research and Molecular Biology 36:311-322 (1987).
Danos et al., "Safe and efficient generation of recombinant retroviruses with amphotropic and ecotropic host ranges," Proc. Natl. Acad. Sci. USA 85:6460-6464 (1988).
Dotti et al., "Design and Development of Therapies using Chimeric Antigen Receptor-Expressing T cells," Immunol Rev. 257(1):107-126 (2014).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).

Eglitis et al., "Retroviral Vectors for Introduction of Genes into Mammalian Cells," BioTechniques 6(7):608-614 (1988).
Eyquem et al., "Targeting a CAR to the TRAC locus with CRISPR/Cas9 enhances tumour rejection," Nature 543(7653):113-117 (2017).
Felgner et al., "Lipofection: A highly efficient, lipid-mediated DNA-transfection procedure," Proc. Natl. Acad. Sci. U.S.A. 84:7413-7417 (1987).
Fife et al., "Inhibition of T cell activation and autoimmune diabetes using a B cell surface-linked CTLA-4 agonist," J Clin Invest 116(8):2252-2261 (2006).
Friedmann, "Progress toward Human Gene Therapy," Science 244:1275-1281 (1989).
Giomarelli et al., "Inhibition of thrombin-induced platelet aggregation using human single-chain Fv antibodies specific for TREM-like transcript-I," Thromb Haemost 97:955-963 (2007).
Gross et al., "Endowing T cells with antibody specificity using chimeric T cell receptors," FASEB J. 6:3370-3378 (1992).
Grunstein et al., "Colony hybridization: A method for the isolation of cloned DNAs that contain a specific gene," Proc. Natl. Acad. Sci., USA 72(10):3961-3965 (1975).
Ho et al., "Inhibition of Cocaine Binding to the Human Dopamine Transporter by a Single Chain Anti-Idiotypic Antibody: Its Cloning, Expression and Functional Properties," BioChim Biophys Acta 1638(3):257-266 (2003).
Hughes et al., "Retroviral Gene Transfer to Primitive Normal and Leukemic Hematopoietic Cells Using Clinically Applicable Procedures," J. Clin. Invest. 89:1817-1824 (1992).
Huston et al., "Protein engineering of antibody binding sites: Recovery of specific activity in an anti-digoxin single-chain Fv analogue produced in *Escherichia coli*," Proc. Nat. Acad. Sci USA, 85:5879-5883 (1988).
International Search Report dated May 30, 2019 in International Application No. PCT/US19/17525.
Johnson, "Gene Therapy for Cystic Fibrosis," Chest 107:77S-83S (1995).
Kabat et al., Sequences of Proteins of Immunological Interest, 4th U.S. Department of Health and Human Services, National Institutes of Health (1987).
Kabat et al., Sequences of Proteins of Immunological Interest, vol. I, Fifth Edition, U.S. Department of Health and Human Services, NIH Publication No. 91-3242 (1991).
Kido et al., "Use of a retroviral vector with an internal opsin promoter to direct gene expression to retinal photoreceptor cells," Current Eye Research 15:833-844 (1996).
Kimmel, "Identification and Characterization of Specific Clones: Strategy for Confirming the Validity of Presumptive Clones," Methods Enzymol. 152:507-511 (1987).
Kloss et al., "Combinatorial antigen recognition with balanced signaling promotes selective tumor eradication by engineered T cells," Nature Biotechnology 31(1):71-75 (2013).
Krause et al., "Antigen-dependent CD28 Signaling Selectively Enhances Survival and Proliferation in Genetically Modified Activated Human Primary T Lymphocytes," J. Exp Med. 188(4):619-626 (1998).
Le Gal La Salle et al., "An Adenovirus Vector for Gene Transfer into Neurons and Glia in the Brain," Science 259:988-990 (1993).
Ledbetter et al., "Agonistic Activity of a CD40-Specific Single-Chain Fv Constructed from the Variable Regions of mAb G28-5," Crit Rev Immunol 17:427-435 (1997).
MacLeod et al., "Integration of a CD19 Car into the TCR Alpha Chain Locus Streamlines Production of Allogeneic Gene-Edited Car T Cells," Mol. Ther. 25(4):949-961 (2017).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Improved Retroviral Vectors for Gene Transfer and Expression," Biotechniques 7:980-990 (1989).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).

(56) References Cited

OTHER PUBLICATIONS

Miyoshi et al., "Stable and efficient gene transfer into the retina using an HIV-based lentiviral vector," Proc. Natl. Acad. Sci. U.S.A. 94:10319-10323 (1997).
Moen, "Directions in Gene Therapy," Blood Cells 17:407-416 (1991).
Moosmayer et al., "A single-chain TNF receptor antagonist is an effective inhibitor of TNF mediated cytotoxicity," Ther Immunol 2:31-40 (1995).
Morgan et al., "Cancer Regression in Patients After Transfer of Genetically Engineered Lymphocytes," Science 314:126-129 (2006).
Myers et al., "Optimal alignments in linear space," Cabios 4:11-17 (1988).
Naldini et al., "In Vivo Gene Delivery and Stable Transduction of Nondividing Cells by a Lentiviral Vector," Science 272:263-267 (1996).
Needleman et al., "A General Method Applicable to the Search for Similarities in the Amino Acid Sequence of Two Proteins," J. Mol. Biol. 48:443-453 (1970).
Ono et al., "Plasmid DNAs directly injected into mouse brain with lipofectin can be incorporated and expressed by brain cells," Neuroscience Letters 117:259-263 (1990).
Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus-specific cytotoxic T lymphocytes by artificial antigen-presenting cells expressing a single HLA allele," Blood 102:2498-2505 (2003).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the β2-Adrenergic Receptor," J Biol Chem 278(38):36740-36747 (2003).
Rosenberg et al., "Gene Transfer into Humans-Immunotherapy of Patients With Advanced Melanoma, Using Tumor-Infiltrating Lymphocytes Modified By Retroviral Gene Transduction," N. Engl. J Med 323:570-578 (1990).
Sadelain et al., "Targeting Tumours with Genetically Enhanced T Lymphocytes," Nat Rev Cancer 3:35-45 (2003).
Sadelain et al., "Targeting tumours with genetically enhanced T lymphocytes," Nature Reviews Cancer; 3:35-45 (2003).
Sadelain et al., "The basic principles of chimeric antigen receptor (CAR) design," Cancer Discovery 3(4):388-398 (2013).
Sharp, "Gene Therapy," The Lancet 337:1277-1278 (1991).
Shieh et al., "Transgenic Expression of Single-Chain Anti-CTLA-4 Fv on β Cells Protects Nonobese Diabetic Mice from Autoimmune Diabetes," J Immunol 183:2277-2285 (2009).
Stec et al., "Cyclic trans-phosphorylation in a homodimer as the predominant mechanism of EGFRvIII action and regulation," Oncotarget 9(9):8560-8572 (2018).
Straubinger et al., "Liposomes as Carriers for Intracellular Delivery of Nucleic Acids," Methods in Enzymology 101:512-527 (1983).
Tolstoshev et al., "Gene expression using retroviral vectors," Current Opinion in Biotechnology 1:55-61 (1990).
Wahl et al., "Improved Radioimaging and Tumor Localization with Monoclonal F(ab')2," J. Nucl Med 24:316-325 (1983).
Wahl et al., "Molecular Hybridization of Immobilized Nucleic Acids: Theoretical Concepts and Practical Considerations," Methods Enzymol 152:399-407 (1987).
Walseng et al., "A TCR-based Chimeric Antigen Receptor," Sci Rep. 7(1):10713; 1-10 (2017).
Wolff et al., "Direct Gene Transfer into Mouse Muscle in Vivo," Science 247:1465-1468 (1990).
Wu et al., "Receptor-mediated Gene Delivery and Expression in Vivo," Journal of Biological Chemistry 263:14621-14624 (1988).
Wu et al., "Targeting Genes: Delivery and Persistent Expression of a Foreign Gene Driven by Mammalian Regulatory Elements in Vivo," Journal of Biological Chemistry 264:16985-16987 (1989).
Xie et al., "Direct demonstration of MuSK involvement in acetylcholine receptor clustering through identification of agonist ScFv," Nat Biotech 15:768-771 (1997).
Xu et al., "Correction of the enzyme deficiency in hemapoietic cells of Gaucher patients using a clinically acceptable retroviral supernatant transduction protocol," Exp. Hemat. 22:223-230 (1994).
Zhao et al., "Characteristics of an scFv Antibody Fragment That Binds to Immunoglobulin G of Graves' Disease Patients and Inhibits Autoantibody-Mediated Thyroid-Stimulating Activity," Hyrbidoma (Larchmt) 27(6):445-451 (2008).
Extended European Search Report, mailed Nov. 30, 2021, for European Application No. 19751805.3.
Torikai et al., "A foundation of universal T-cell based immunotherapy: T cells engineered to express a CD19-specific chimeric-antigen-receptor and eliminate expression of endogenous TCR", Blood, American Society of Hematology, vol. 119, No. 24, 5697-5705 (2012).
Mansilla-Soto et al., "HLA-independent T cell receptors for targeting tumors with low antigen density" Nature Medicine vol. 28, pp. 345-352 (2022).
Bridgeman et al., "CD3ζ-based chimeric antigen receptors mediate T cell activation via cis- and trans-signalling mechanisms: implications for optimization of receptor structure for adoptive cell therapy," Clinical and Experimental Immunology, 175:258-267 (2013).
Brudno et al., "Toxicities of chimeric antigen receptor T cells: recognition and management," Blood, 127(26):3321-3330 (2016).
Singer at al., Genes and Genomes, Moscow, "Mir", 1998, vol. 1 (see pp. 63-64).
U.S. Appl. No. 16/990,185, Oct. 13, 2023 Restriction Requirement.
Li et al., "Prevention of carcinogenesis and inhibition of breast cancer tumor burden by dietary stearate," Carcinogenesis 32(8):1251-1258 (2011).
Marzi et al., "Cloning, expression, and interaction of human T-cell receptors with the bacterial superantigen SSA," Eur. J. Biochem. 271:4075-4083 (2004).
U.S. Appl. No. 16/990,185, filed Apr. 18, 2024 Non-Final Office Action.

* cited by examiner

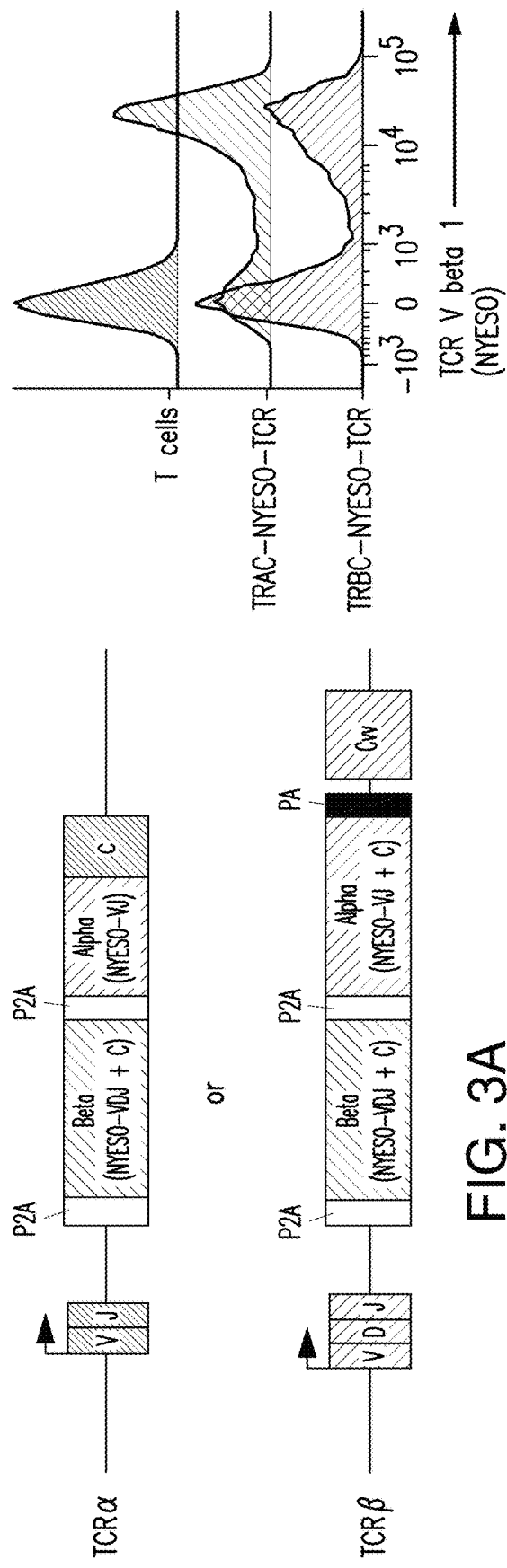
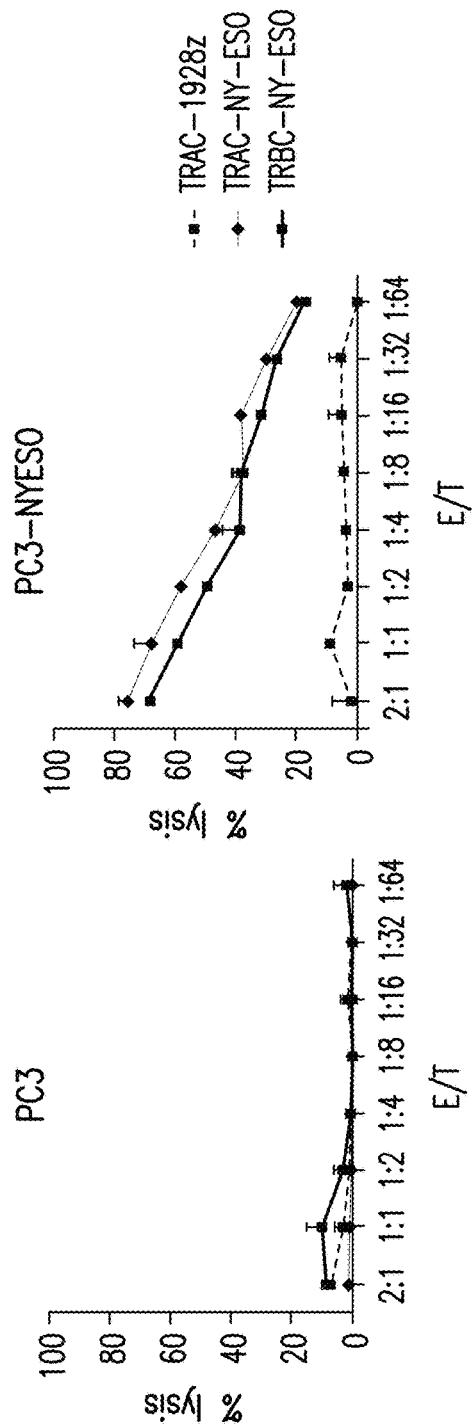
FIG. 3A
FIG. 3B
FIG. 3C

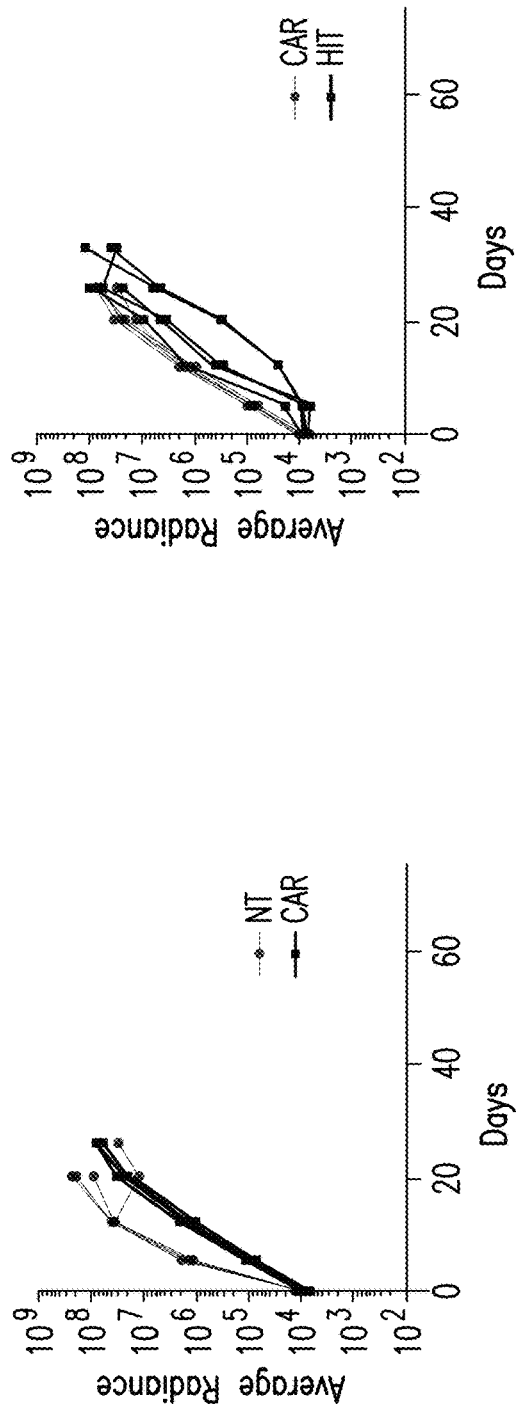
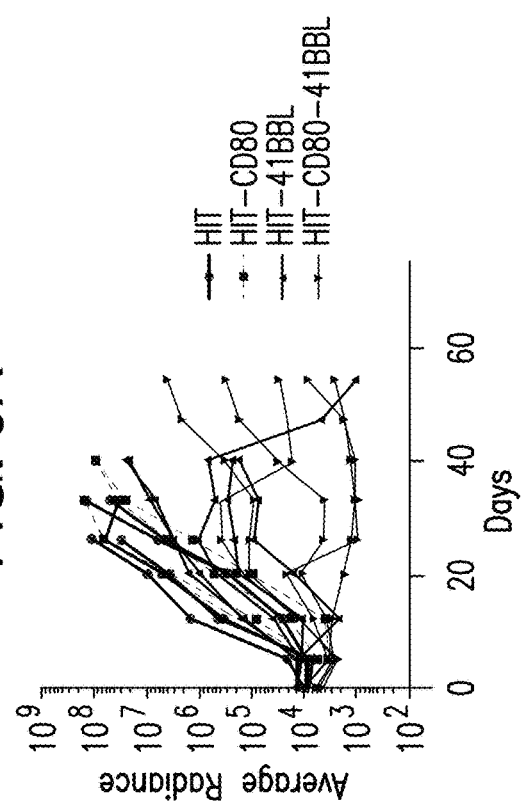
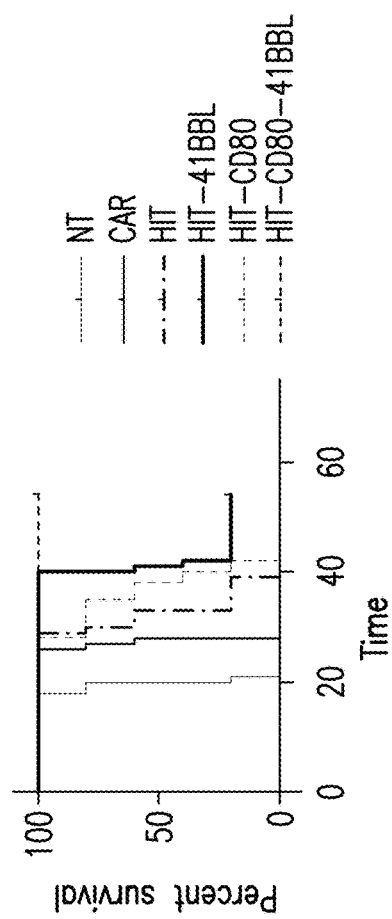
FIG. 9A
FIG. 9B
FIG. 9C
FIG. 9D

CELLS COMPRISING NON-HLA RESTRICTED T CELL RECEPTORS

CROSS-REFERENCE TO RELATED APPLICATIONS

This application is a Continuation of U.S. patent application Ser. No. 16/990,185, filed Aug. 11, 2020, which is a Continuation of International Patent Application No.: PCT/US2019/017525 filed Feb. 11, 2019, which claims priority to U.S. Provisional Patent Application Ser. No. 62/629,072, filed Feb. 11, 2018, the content of each of which is incorporated by reference in its entirety, and to each of which priority is claimed.

SEQUENCE LISTING

The specification further incorporates by reference the Sequence Listing submitted herewith via EFS on Oct. 19, 2021. Pursuant to 37 C.F.R. § 1.52(e)(5), the Sequence Listing text file, identified as 0884860120_SL.txt, is 72,389 bytes and was created on Oct. 19, 2021. The entire contents of the Sequence Listing are hereby incorporated by reference. The Sequence Listing does not extend beyond the scope of the specification and thus does not contain new matter.

INTRODUCTION

The presently disclosed subject matter provides methods and compositions for enhancing the immune response toward cancers and pathogens. It relates to novel designs of T cell receptors (TCRs) and engineered immunoresponsive cells comprising the same. The engineered immunoresponsive cells comprising the novel TCRs are antigen-directed.

BACKGROUND OF THE INVENTION

Adoptive immunotherapy using antigen recognizing receptors (e.g., chimeric antigen receptors (CARs)) has shown remarkable clinical results in the treatment of leukemia and is one of the most promising new strategies to treat cancer. To generate CAR therapies, current clinical protocols employ autologous T cells and randomly integrating vectors, including gamma-retroviral, lentiviral and transposons, which all result in semi-random integration and variable expression of the CAR owing to transgene variegation. Altogether, the conjunction of autologous cell sourcing and random vector integration is prone to generating cell products with variable potency. Thus, there is a need of novel designs of antigen recognizing receptors having consistent potency and increased ability to detect low levels of target antigen.

SUMMARY OF THE INVENTION

The presently disclosed subject matter generally provides HLA-independent (or non-HLA restricted) T cell receptors (referred to as "HI-TCRs") that bind to an antigen of interest in an HLA-independent manner and immunoresponsive cells comprising thereof. The presently disclosed subject matter also provides methods of using such cells for inducing and/or enhancing an immune response to a target antigen, and/or treating and/or preventing neoplasia or other diseases/disorders where an increase in an antigen-specific immune response is desired.

The presently disclosed subject matter provides recombinant T cell receptor (TCR) comprising an antigen binding chain that comprises an extracellular antigen-binding domain and a constant domain, wherein the recombinant TCR binds to an antigen in an HLA-independent manner.

In certain embodiments, the constant domain comprises a native or modified TRAC peptide, and/or a native or modified TRBC peptide. In certain embodiments, the constant domain is capable of forming a homodimer or a heterodimer with another constant domain.

In certain embodiments, the recombinant TCR is expressed from an expression cassette placed in an endogenous TRAC locus and/or a TRBC locus of an immunoresponsive cell. In certain embodiments, the placement of the recombinant TCR expression cassette disrupts or abolishes the endogenous expression of a TCR comprising a native TCR α chain and/or a native TCR β chain in the immunoresponsive cell. In certain embodiments, the placement of the recombinant TCR expression cassette prevents or eliminates mispairing between the recombinant TCR and a native TCR α chain and/or a native TCR β chain in the immunoresponsive cell. In certain embodiments, the antigen binding chain is capable of associating with a CD3ζ polypeptide. The antigen binding chain, upon binding to an antigen, is capable of activating the CD3ζ polypeptide associated to the antigen binding chain. The activation of the CD3ζ polypeptide is capable of activating an immunoresponsive cell. The CD3ζ polypeptide can be endogenous or exogenous. In certain embodiments, the CD3ζ polypeptide is endogenous and is endogenous and integrated in the native CD3 complex. In certain embodiments, the CD3ζ polypeptide is exogenous and optionally integrated with a co-stimulatory molecule selected from the group consisting of a CD28 polypeptide, a 4-1BB polypeptide, an OX40 polypeptide, an ICOS polypeptide, a DAP-10 polypeptide and any combination thereof. In certain embodiments, the antigen binding chain further comprises a co-stimulatory region, wherein the recombinant TCR, upon binding to an antigen, is capable of stimulating an immunoresponsive cell. The co-stimulatory region can include a co-stimulatory molecule selected from the group consisting of a CD28 polypeptide, a 4-1BB polypeptide, an OX40 polypeptide, an ICOS polypeptide, a DAP-10 polypeptide and any combination thereof. In certain embodiments, the co-stimulatory region comprises a CD28 polypeptide.

In certain embodiments, the recombinant TCR is capable of associating with a CD3 complex. In certain embodiments, the recombinant TCR is capable of integrating with a CD3 complex and providing HLA-independent antigen recognition. In certain embodiments, the CD3 complex is endogenous. In certain embodiments, the recombinant TCR replaces an endogenous TCR in a CD3/TCR complex.

In certain embodiments, the extracellular antigen-binding domain is capable of dimerizing with another extracellular antigen-binding domain. The extracellular antigen-binding domain can include a ligand for a cell-surface receptor, a receptor for a cell surface ligand, an antigen binding portion of an antibody or a fragment thereof or an antigen binding portion of a TCR. In certain embodiments, the extracellular antigen-binding domain comprises a heavy chain variable region ($V_H$) of an antibody, or a VHH from a camelid $V_H$-only antibody and/or a light chain variable region ($V_L$) of an antibody. In certain embodiments, the extracellular antigen-binding domain is capable of dimerizing with another extracellular antigen-binding domain. In certain embodiments, the extracellular antigen-binding domain comprises a $V_H$ of an antibody, wherein the human, murine, or camelid $V_H$ is capable of dimerizing with another extracellular antigen-binding domain comprising a $V_L$ of the antibody and form a fragment variable (Fv). In certain embodiments, the extracellular antigen-binding domain comprises a $V_L$ of an antibody, wherein the $V_L$ is capable of dimerizing with another extracellular antigen-binding domain comprising a $V_H$ of the antibody and form a fragment variable (Fv).

In certain embodiments, the recombinant TCR binds to a tumor antigen. The tumor antigen can be selected from the group consisting of CD19, MUC16, MUC1, CAIX, CEA, CD8, CD7, CD10, CD20, CD22, CD30, CLL1, CD33, CD34, CD38, CD41, CD44, CD49f, CD56, CD74, CD133, CD138, EGP-2, EGP-40, EpCAM, erb-B2,3,4, FBP, Fetal acetylcholine receptor, folate receptor-a, GD2, GD3, HER-2, hTERT, IL-13R-a2, K-light chain, KDR, LeY, L1 cell adhesion molecule, MAGE-A1, Mesothelin, ERBB2, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, and CD99, CD70, ADGRE2, CCR1, LILRB2, LILRB4, PRAME, and ERBB. In certain embodiments, the tumor antigen is CD19.

In certain embodiments, the recombinant TCR exhibits greater antigen sensitivity than a CAR targeting the same antigen. In certain embodiments, the recombinant TCR is capable of inducing an immune response when binds to an antigen that has a low density on the surface of a tumor cell. In certain embodiments, the antigen that has a low density on the cell surface has below about 2,000 molecules per cell.

The presently disclosed subject matter further provides immunoresponsive cells comprising a recombinant TCR described herein. In certain embodiments, the expression cassette of at least one antigen binding chain of the recombinant TCR is placed at an endogenous gene locus of the immunoresponsive cell. In certain embodiments, the expression cassettes of two antigen binding chains of the recombinant TCR are placed at an endogenous gene locus of the immunoresponsive cell, wherein the two antigen binding chains are capable of dimerization. The placement of the expression cassette of the recombinant TCR can disrupt or abolish the endogenous expression of a TCR comprising a native TCR α chain and/or a native TCR β chain in the immunoresponsive cell, whereby preventing or eliminating mispairing between the recombinant TCR and a native TCR α chain and/or a native TCR β chain in the immunoresponsive cell. The endogenous gene locus can be a CD3δ locus, a CD3ε locus, a CD247 locus, a B2M locus, a TRAC locus, a TRBC locus or a TRGC locus or a TRDC locus. In certain embodiments, the endogenous gene locus is a TRAC locus and/or a TRBC locus. The endogenous gene locus can include a modified transcription terminator region. In certain embodiments, the modified transcription terminator region comprises a genomic element selected from the group consisting of a TK transcription terminator, a GCSF transcription terminator, a TCRA transcription terminator, an HBB transcription terminator, a bovine growth hormone transcription terminator, a SV40 transcription terminator and a P2A element; the P2A element allows the use of the endogenous transcription terminator of the targeted gene. In certain embodiments, when one endogenous T cell receptor locus in a cell is modified to express the at least one antigen binding chain of the recombinant TCR, one or more other endogenous T cell receptor locus in the cell is modified to eliminate the expression of an endogenous TCR chain. In certain embodiments, the one or more other endogenous T cell receptor loci are further modified to express a gene of interest. The gene of interest can be an anti-tumor cytokine, a co-stimulatory molecule ligand, a tracking gene or a suicide gene. In certain embodiments, one or more endogenous TCR loci are further modified to incorporate a sequence encoding co-stimulatory signaling domain(s) to generate a TCR chain containing such signaling domain(s) at the carboxy terminus.

In certain embodiments, the immunoresponsive cell is selected from the group consisting of a T cell, a cytotoxic T lymphocyte (CTL), a regulatory T cell, a Natural Killer T (NKT) cell, a human embryonic stem cell, and a pluripotent stem cell from which lymphoid cells may be differentiated. In certain embodiments, the immunoresponsive cell is autologous.

In certain embodiments, the immunoresponsive cell further comprises at least one exogenous co-stimulatory ligand. In certain embodiments, the co-stimulatory ligand is selected from the group consisting of CD80, CD86, 41BBL, CD275, CD40L, OX40L and any combination thereof. In certain embodiments, the cell further comprises or consists of one exogenous co-stimulatory ligand. In certain embodiments, the one exogenous co-stimulatory ligand is CD80 or 4-1BBL. In certain embodiments, the cell further comprises or consists of two exogenous co-stimulatory ligands. In certain embodiments, In certain embodiments, the two exogenous co-stimulatory ligands are CD80 and 4-1BBL.

In certain embodiments, the immunoresponsive cell further comprises at least one chimeric costimulatory receptor (CCR). In certain embodiments, the CCR comprising a co-stimulatory molecule selected from the group consisting of a CD28 polypeptide, a 4-1BB polypeptide, an OX40 polypeptide, an ICOS polypeptide, a DAP-10 polypeptide and any combination thereof.

The presently disclosed subject matter also provides pharmaceutical compositions comprising the immunoresponsive cell(s) disclosed herein and a pharmaceutically acceptable excipient. The pharmaceutical composition can be used for treating a neoplasia.

Further provided are methods of reducing tumor burden in a subject. In addition, the presently disclosed subject matter provides methods of lengthening survival of a subject having a neoplasm (e.g., cancer). In certain embodiments, the method comprises administering to the subject an effective amount of the immunoresponsive cells described herein or the pharmaceutical composition described herein.

The presently disclosed subject matter also provides methods of treating or preventing a neoplasm. In certain embodiments, the method comprises administering to the subject an effective amount of the immunoresponsive cells described herein or the pharmaceutical composition described herein. The neoplasm can be selected from the group consisting of blood cancer, B cell leukemia, multiple myeloma, acute lymphoblastic leukemia (ALL), chronic lymphocytic leukemia, non-Hodgkin's lymphoma and adenocarcinoma. In certain embodiments, the neoplasm is B cell leukemia, multiple myeloma, acute lymphoblastic leukemia (ALL), chronic lymphocytic leukemia, or non-Hodgkin's lymphoma, and the recombinant TCR binds to CD19. In certain embodiments, the neoplasm is B cell leukemia, multiple myeloma, acute lymphoblastic leukemia (ALL), chronic lymphocytic leukemia, an adenocarcinoma, or non-Hodgkin's lymphoma, and the recombinant TCR binds to CD19, MUC16, MUC1, CAIX, CEA, CD8, CD7, CD10, CD20, CD22, CD30, CLL1, CD33, CD34, CD38, CD41, CD44, CD49f, CD56, CD74, CD133, CD138, EGP-2, EGP-40, EpCAM, Erb-B2,3,4, FBP, Fetal acetylcholine receptor, folate receptor-a, GD2, GD3, HER-2, hTERT, IL-13R-a2, K-light chain, KDR, LeY, L1 cell adhesion molecule, MAGE-A1, Mesothelin (MSLN), ERBB2, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, CD99, CD70, ADGRE2, CCR1, LILRB2, LILRB4, PRAME, and ERBB. In certain embodiments, the neoplasm is CD19+ ALL.

The presently disclosed subject matter further provides methods for producing an antigen-specific immunoresponsive cell. In certain embodiments, the method comprises introducing into an immunoresponsive cell a nucleic acid sequence encoding a recombinant TCR described herein. The nucleic acid sequence can be comprised in a vector. In certain embodiments, the expression cassette of at least one antigen binding chain of the recombinant TCR is placed at an endogenous gene locus of the immunoresponsive cell. In certain embodiments, the expression cassettes of two antigen binding chains of the recombinant TCR are placed at an endogenous gene locus of the immunoresponsive cell, wherein the two antigen binding chains are capable of dimerization. The endogenous gene locus can be a CD3δ locus, a CD3ε locus, a CD247 locus, a B2M locus, a TRAC locus, a TRBC locus, a TRDC locus and/or a TRGC locus. In certain embodiments, the endogenous gene locus is a TRAC locus or a TRBC locus. In certain embodiments, the placement of the expression cassette of the recombinant TCR disrupts or abolishes the endogenous expression of a TCR comprising a native TCR α chain and/or a native TCR β chain in the immunoresponsive cell, whereby preventing or eliminating mispairing between the recombinant TCR and a native TCR α chain and/or a native TCR β chain in the immunoresponsive cell. In certain embodiments, the endogenous gene locus comprises a modified transcription terminator region. In certain embodiments, the modified transcription terminator region comprises a genomic element selected from the group consisting of a TK transcription terminator, a GCSF transcription terminator, a TCRA transcription terminator, an HBB transcription terminator, a bovine growth hormone transcription terminator, an SV40 transcription terminator and a P2A element. In certain embodiments, when one endogenous T cell receptor locus in a cell is modified to express the at least one antigen binding chain of the recombinant TCR, one or more other endogenous T cell receptor locus in the cell is modified to eliminate the expression of an endogenous TCR chain. In certain embodiments, the one or more other endogenous T cell receptor locus are further modified to express a gene of interest. In certain embodiments, the gene of interest is an anti-tumor cytokine, a co-stimulatory molecule ligand, a tracking gene or a suicide gene.

The presently disclosed subject matter further provides nucleotide acids encoding a recombinant TCR described herein, and nucleic acid compositions comprising a recombinant TCR described herein. In certain embodiments, the nucleic acid sequences are comprised in a vector. The presently disclosed subject matter also provides vectors comprising the nucleic acid composition described herein. Further provided are kits comprising a recombinant TCR described herein, an immunoresponsive cell described herein, a pharmaceutical composition described herein, a nucleic acid composition described herein, or a vector described herein. In certain embodiments, the kit further comprises written instructions for treating and/or preventing a neoplasm, a pathogen infection, an autoimmune disorder, or an allogeneic transplant.

Illustrative neoplasms for which the presently disclosed subject matter can be used include, but are not limited to leukemias (e.g., acute leukemia, acute lymphocytic leukemia, acute myelocytic leukemia a, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

The presently disclosed subject matter further provides use of any recombinant TCR, any pharmaceutical composition or any immunoresponsive cell disclosed herein for used in a therapy.

BRIEF DESCRIPTION OF THE FIGURES

The following Detailed Description, given by way of example, but not intended to limit the presently disclosed subject matter to specific embodiments described, may be understood in conjunction with the accompanying drawings.

FIG. 1A depicts schematic representation of the T Cell Receptor (TCR), the B Cell Receptor (BCR), a Chimeric Antigen Receptor (CAR) and the HLA-Independent TCR-based Chimeric Antigen Receptor (HIT-CAR, i.e., HI-TCR or HIT). FIG. 1B depicts CRISPR/Cas9-targeted integration of the 3 receptors into the TRAC locus. Top: TRAC locus; middle: rAAV6 containing the different receptor cassette flanked by homology arms. FIG. 1C depicts representative TCR/Mouse F(ab')2 flow cytometry plots 4 days after TRAC targeting. The TCR antibody epitope recognize the constant chain of the TCR alpha and beta. FIG. 1D depicts cytotoxic activity using an 18-hour bioluminescence assay, using firefly luciferase (FFL)-expressing NALM-6 as targets cells (n=3). (E) Relative CAR MFI (1=MFI at 0 h) of CART cells after 1, 2 or 4 (arrows) stimulations on CD19 positive target cells.

FIG. 2A depicts representative TCR/Mouse F(ab')2 flow cytometry plots 4 days after TRAC targeting.

FIG. 2B depicts Kaplan-Meier analysis of the mice survival where NALM-6-bearing mice were treated with $5\times10^5$ CAR T cells.

FIGS. 3A-3E depict gene targeting strategy and expression of NYESO TCR. FIG. 3A depicts schematic representation of the NYESO TCR genes integrated into the TCR alpha or beta chain. FIG. 3B depicts representative TCR-V-beta-1 flow cytometry plots 4 days after TRAC or TRBC targeting. FIG. 3C depicts cytotoxic activity using an 18-hour bioluminescence assay, using firefly luciferase (FFL)-expressing PC3 as targets cells (n=3). FIG. 3D depicts schematic representation of a co-targeting into both the TCR alpha and the TCR beta. (E) Representative TCR-V-beta-1/4-1BBL flow cytometry plots 4 days after TRAC and TRBC co-targeting.

FIG. 4A depicts schematic representation of the 1928z CAR gene integrated into the TRAC locus. Poly A (black box) corresponds to the segment of the CAR cassette that was modified to test different viral and mammalian 3'UTRs. FIG. 4B depicts representative CAR flow plots 3 days after TRAC (left panel). and geometric mean fluorescence intensity (gMFI), MFI, and Median values for the CAR-expressing population (right panel). Boxed is the original 3'UTR sequence of bovine growth hormone poly A. FIG. 4C depicts absolute (top) and relative (bottom) CAR MFI (1=MFI at 0 h) of CAR T cells after 1, 2 stimulations on CD19 positive target cells (as shown in FIG. 1).

FIG. 5A depicts FFL-NALM-6-bearing mice were treated with $1\times10^5$ CAR T cells, where tumor burden is shown as bioluminescent signal quantified per animal 14 days post T-cell injection. n=6 mice per group. FIG. 5B depicts tumor burden (average radiance) of NALM-6-bearing mice treated with $1\times10^5$ CAR T cells (n=6; line=one mouse) quantified at days 7, 14, and 21 post T-cell injection.

FIG. 6A depicts CRISPR/Cas9-targeted CAR or HIT gene integration into the TRAC locus. Top, TRAC locus; middle, rAAV6 containing the CAR cassette flanked by homology arms; bottom, rAAV6 containing the HIT cassette flanked by homology arms. FIG. 6B depicts representative CAR/HIT flow plots 4 days after transfection of T cells with Cas9 mRNA and TRAC gRNA and addition of AAV6. CAR and HIT surface protein were detected using a goat anti-mouse IgG. FIG. 6C depicts average CAR/HIT mean fluorescence intensity (MFI) analyzed by FACS 4 days after transduction (n=6 independent experiments).

FIG. 7A depicts FACS analysis of representative Nalm6 clones for each CD19 expression level group (Neg=negative). FIG. 7B depicts cytotoxic activity using an 4 h bioluminescence assay, using NALM6 as targets cells expressing different CD19 levels and CAR (red squares) or HIT (blue circles) T cells at 1:1 effector (E):target (T) ratio.

FIGS. 9A-9D depict HIT T cells expressing costimulatory ligands outperform CAR T cells in controlling established B-ALL tumor with very low CD19 levels. NALM-6-bearing mice were treated with $4\times10^5$ untransduced (NT), CAR, or HIT T cells. Tumor burden was quantified weekly over a 54-day period using BLI. Quantification is the average photon count of ventral and dorsal acquisitions per animal at all given time points. Each line represents one mouse, and n=5 mice per group. FIG. 9A depicts untransduced (black) vs CAR (red) T cells. FIG. 9B depicts CAR (red) vs HIT (green) T cells. FIG. 9C depicts T cells expressing HIT alone (green), HIT+CD80 co-stimulatory ligand (orange), HIT+41BBL co-stimulatory ligand (pink), or HIT+CD80+41BBL co-stimulatory ligands (blue). FIG. 9D depicts mouse survival analysis.

FIG. 10A depicts CRISPR/Cas9-targeted CAR gene integration into the TRAC locus. The targeting construct (AAV) contains the 1928z CAR coding sequence followed by a 3'UTR sequence, flanked by sequences homologous to the TRAC locus (LHA and RHA, left and right homology arm). FIG. 10B depicts each 3'UTR sequence provides different CAR surface levels (measured by FACS). TK thymidine kinase (short version); GCSF: human GCSF, derived from pEF-BOS plasmid; TCRa: TCR alpha, exon 4; HBB: human B-globin; RBG: rabbit B-globin; SV40: simian virus 40 poly A; P2A: porcine teschovirus-1 self-cleaving 2A sequence; it allowed the use of the endogenous TRAC poly A sequence. FIG. 10C depicts CAR T cells were stimulated once (indicated by a red arrow) with CD19-expressing 3T3 cells, and CAR MFI was measured every 24 h over a 3-day period. All CAR T cells show similar CAR expression regulation.

DETAILED DESCRIPTION OF THE INVENTION

Figures 1A, 1B:
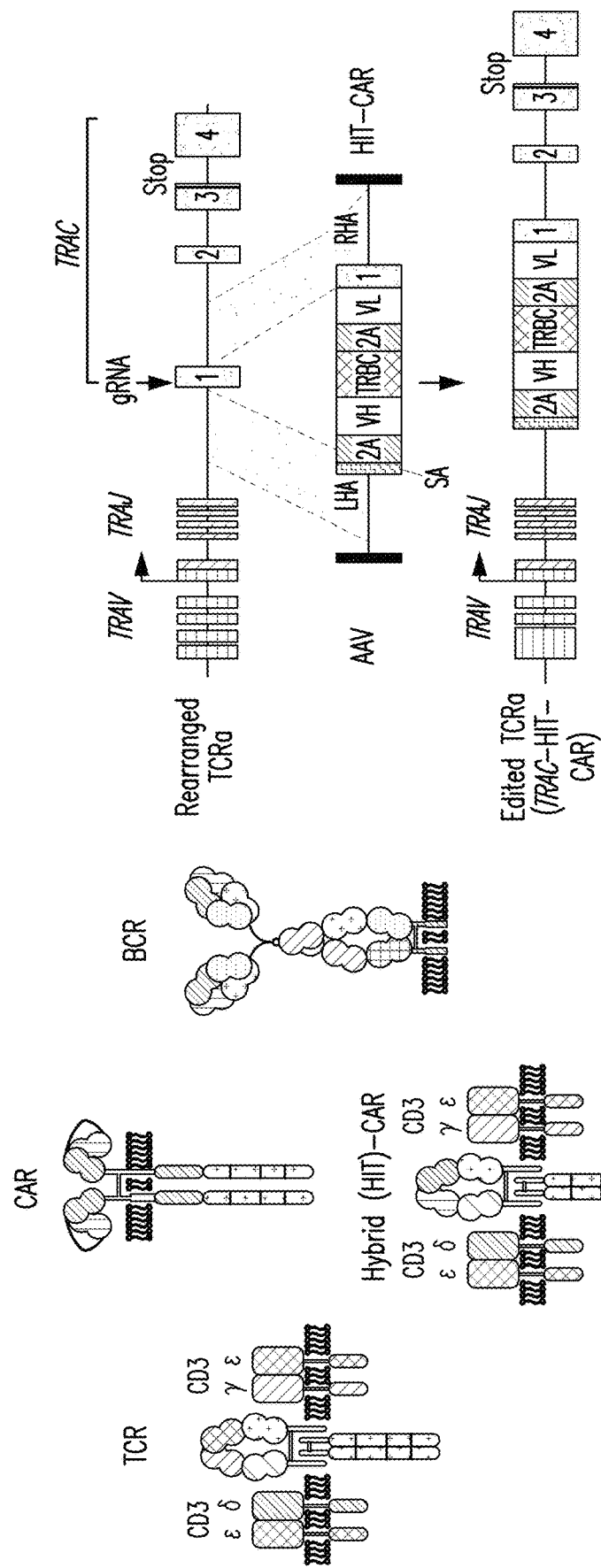
FIGS. 1A-1E depict HLA-Independent TCR-based Chimeric Antigen Receptor HIT (HIT-CAR, i.e., HI-TCR or HIT) and gene targeting strategy at the TRAC locus in human T cells.

The presently disclosed subject matter provides HLA-independent (or non-HLA restricted) T cell receptors (referred to as "HI-TCRs") that bind to an antigen of interest in an HLA-independent manner. In certain embodiments, the HI-TCRs are TCR molecules where the TCR variable domain is replaced by the variable domain from an antibody (Fv), resulting in a FvTCR. In certain non-limiting embodiments, the HI-TCR can bind to a tumor antigen or a pathogen antigen. The presently disclosed subject matter also provides cells, including genetically modified immunoresponsive cells (e.g., T cells, NKT cells, or CTL cells) comprising the presently disclosed HI-TCR. In certain non-limiting embodiments, binding of the antigen by the HI-TCR is capable of activating the immunoresponsive cell. The presently disclosed subject matter also provides methods of using such cells for inducing and/or enhancing an immune response to a target antigen, and/or treating and/or preventing neoplasia or other diseases/disorders where an increase in an antigen-specific immune response is desired.

1. Definitions

Unless defined otherwise, all technical and scientific terms used herein have the meaning commonly understood by a person skilled in the art. The following references provide one of skill with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to about 20%, e.g., up to about 10%, up to about 5%, or up to about 1% of a given value. Alternatively, particularly with respect to biological systems or processes, the term can mean within an order of magnitude, e.g., within about 5-fold or within about 2-fold, of a value.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds to an antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated. This phosphorylation in turn initiates a T cell activation pathway ultimately activating transcription factors, such as NF-κB and AP-1. These transcription factors induce global gene expression of the T cell to increase IL-2 production for proliferation and expression of master regulator T cell proteins in order to initiate a T cell mediated immune response.

By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Receiving multiple stimulatory signals can be important to mount a robust and long-term T cell mediated immune response. T cells can quickly become inhibited and unresponsive to antigen. While the effects of these co-stimulatory signals may vary, they generally result in increased gene expression in order to generate long lived, proliferative, and anti-apoptotic T cells that robustly respond to antigen for complete and sustained eradication.

The term "antigen recognizing receptor" as used herein refers to a receptor that is capable of activating an immune or immunoresponsive cell (e.g., a T-cell) in response to its binding to an antigen. Non-limiting examples of antigen recognizing receptors include native or endogenous T cell receptors ("TCRs"), and chimeric antigen receptors ("CARs").

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., J. Nucl. Med. 24:316-325 (1983). As used herein, antibodies include whole native antibodies, bispecific antibodies; chimeric antibodies; Fab, Fab', single chain V region fragments (scFv), fusion polypeptides, and unconventional antibodies. In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242).

As used herein, the term "single-chain variable fragment" or "scFv" is a fusion protein of the variable regions of the heavy ($V_H$) and light chains ($V_L$) of an immunoglobulin covalently linked to form a $V_H$::$V_L$ heterodimer. The $V_H$ and $V_L$ are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Biol Chern 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, the term "affinity" is meant a measure of binding strength. Affinity can depend on the closeness of stereochemical fit between antibody combining sites and antigen determinants, on the size of the area of contact between them, and/or on the distribution of charged and hydrophobic groups. As used herein, the term "affinity" also includes "avidity", which refers to the strength of the antigen-antibody bond after formation of reversible complexes. Methods for calculating the affinity of an antibody for an antigen are known in the art, including, but not limited to, various antigen-binding experiments, e.g., functional assays (e.g., flow cytometry assay).

The term "chimeric antigen receptor" or "CAR" as used herein refers to a molecule comprising an extracellular antigen-binding domain that is fused to an intracellular signaling domain that is capable of activating or stimulating an immunoresponsive cell, and a transmembrane domain. In certain embodiments, the extracellular antigen-binding domain of a CAR comprises a scFv. The scFv can be derived from fusing the variable heavy and light regions of an antibody. Alternatively or additionally, the scFv may be derived from Fab's (instead of from an antibody, e.g., obtained from Fab libraries). In certain embodiments, the scFv is fused to the transmembrane domain and then to the intracellular signaling domain. In certain embodiments, the CAR has a high binding affinity or avidity for the antigen.

As used herein, the term "nucleic acid molecules" include any nucleic acid molecule that encodes a polypeptide of interest or a fragment thereof. Such nucleic acid molecules need not be 100% homologous or identical with an endogenous nucleic acid sequence, but may exhibit substantial identity. Polynucleotides having "substantial identity" or "substantial homology" to an endogenous sequence are typically capable of hybridizing with at least one strand of a double-stranded nucleic acid molecule. By "hybridize" is meant a pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, e.g., less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, e.g., at least about 50% formamide. Stringent temperature conditions will ordinarily include temperatures of at least about 30° C., at least about 37° C., or of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In certain embodiments, hybridization will occur at 30° C. in 750 mM NaCl, 75 mM trisodium citrate, and 1% SDS. In certain embodiments, hybridization will occur at 37° C. in 500 mM NaCl, 50 mM trisodium citrate, 1% SDS, 35% formamide, and 100 µg/ml denatured salmon sperm DNA (ssDNA). In certain embodiments, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, e.g., less than about 15 mM NaCl and 1.5 mM trisodium citrate. Stringent temperature conditions for the wash steps will ordinarily include a temperature of at least about 25° C., of at least about 42° C., or of at least about 68° C. In certain embodiments, wash steps will occur at 25° C. in 30 mM NaCl, 3 mM trisodium citrate, and 0.1% SDS. In certain embodiments, wash steps will occur at 42° C. in 15 mM NaCl, 1.5 mM trisodium citrate, and 0.1% SDS. In certain embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" or "substantially homologous" is meant a polypeptide or nucleic acid molecule exhibiting at least about 50% homologous or identical to a reference amino acid sequence (for example, any one of the amino acid sequences described herein) or nucleic acid sequence (for example, any one of the nucleic acid sequences described herein). In certain embodiments, such a sequence is at least about 60%, at least about 65%, at least about 70%, at least about 75%, at least about 80%, at least about 85%, at least about 90%, at least about 95%, at least about 99%, or at least about 100% homologous or identical to the sequence of the amino acid or nucleic acid used for comparison.

Sequence identity can be measured by using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "analog" is meant a structurally related polypeptide or nucleic acid molecule having the function of a reference polypeptide or nucleic acid molecule.

The term "ligand" as used herein refers to a molecule that binds to a receptor. In certain embodiments, the ligand binds to a receptor on another cell, allowing for cell-to-cell recognition and/or interaction.

The term "constitutive expression" or "constitutively expressed" as used herein refers to expression or expressed under all physiological conditions.

By "disease" is meant any condition, disease or disorder that damages or interferes with the normal function of a cell, tissue, or organ, e.g., neoplasia, and pathogen infection of cell.

By "effective amount" is meant an amount sufficient to have a therapeutic effect. In certain embodiments, an "effective amount" is an amount sufficient to arrest, ameliorate, or inhibit the continued proliferation, growth, or metastasis (e.g., invasion, or migration) of a neoplasia.

By "enforcing tolerance" is meant preventing the activity of self-reactive cells or immunoresponsive cells that target transplanted organs or tissues.

By "endogenous" is meant a nucleic acid molecule or polypeptide that is normally expressed in a cell or tissue.

By "exogenous" is meant a nucleic acid molecule or polypeptide that is not endogenously present in a cell, or not present at a level sufficient to achieve the functional effects obtained when over-expressed. The term "exogenous" would therefore encompass any recombinant nucleic acid molecule or polypeptide expressed in a cell, such as foreign, heterologous, and over-expressed nucleic acid molecules and polypeptides. By "exogenous" nucleic acid is meant a nucleic acid not present in a native wild-type cell; for example, an exogenous nucleic acid may vary from an endogenous counterpart by sequence, by position/location, or both. For clarity, an exogenous nucleic acid may have the same or different sequence relative to its native endogenous counterpart; it may be introduced by genetic engineering into the cell itself or a progenitor thereof, and may optionally be linked to alternative control sequences, such as a non-native promoter or secretory sequence.

By a "heterologous nucleic acid molecule or polypeptide" is meant a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

By "immunoresponsive cell" is meant a cell that functions in an immune response or a progenitor, or progeny thereof.

By "modulate" is meant positively or negatively alter. Exemplary modulations include a about 1%, about 2%, about 5%, about 10%, about 25%, about 50%, about 75%, or about 100% change.

By "increase" is meant to alter positively by at least about 5%. An alteration may be by about 5%, about 10%, about 25%, about 30%, about 50%, about 75%, about 100% or more.

By "reduce" is meant to alter negatively by at least about 5%. An alteration may be by about 5%, about 10%, about 25%, about 30%, about 50%, about 75%, or even by about 100%.

By "isolated cell" is meant a cell that is separated from the molecular and/or cellular components that naturally accompany the cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

The term "antigen-binding domain" as used herein refers to a domain capable of specifically binding a particular antigenic determinant or set of antigenic determinants present on a cell.

"Linker", as used herein, shall mean a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In certain embodiments, the linker comprises a sequence set forth in GGGGSGGGGSGGGGS [SEQ ID NO: 31].

By "neoplasm" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells). In certain embodiments, the neoplasm is a solid tumor.

Illustrative neoplasms for which the presently disclosed subject matter can be used include, but are not limited to leukemias (e.g., acute leukemia, acute lymphocytic leukemia, acute myelocytic leukemia a, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

By "receptor" is meant a polypeptide, or portion thereof, present on a cell membrane that selectively binds one or more ligand.

By "recognize" is meant selectively binds to a target. A T cell that recognizes a tumor can expresses a receptor (e.g., a TCR or CAR) that binds to a tumor antigen.

By "reference" or "control" is meant a standard of comparison. For example, the level of scFv-antigen binding by a cell expressing a CAR and an scFv may be compared to the level of scFv-antigen binding in a corresponding cell expressing CAR alone.

By "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

By "signal sequence" or "leader sequence" is meant a peptide sequence (e.g., 5, 10, 15, 20, 25 or 30 amino acids) present at the N-terminus of newly synthesized proteins that directs their entry to the secretory pathway. Exemplary leader sequences include, but is not limited to, the IL-2 signal sequence: MYRMQLLSCIALSLALVTNS [SEQ ID NO: 12] (human), MYSMQLASCVTLTLVLLVNS [SEQ ID NO: 13] (mouse); the kappa leader sequence: METPAQLLFLLLLWLPDTTG [SEQ ID NO: 14] (human), METDTLLLWVLLLWVPGSTG [SEQ ID NO: 15] (mouse); the CD8 leader sequence: MALPVTALLLPLALLLHAARP [SEQ ID NO: 16] (human); the truncated human CD8 signal peptide: MALPVTALLLPLALLLHA [SEQ ID NO: 28] (human); the albumin signal sequence: MKWVTFISLLFSSAYS [SEQ ID NO: 29] (human); and the prolactin signal sequence: MDSKGSSQKGSRLLLLL-VVSNLLLCQGVVS [SEQ ID NO: 30] (human). By "soluble" is meant a polypeptide that is freely diffusible in an aqueous environment (e.g., not membrane bound).

By "specifically binds" is meant a polypeptide or fragment thereof that recognizes and binds to a biological molecule of interest (e.g., a polypeptide), but which does not substantially recognize and bind other molecules in a sample, for example, a biological sample, which naturally includes a presently disclosed polypeptide.

The term "tumor antigen" as used herein refers to an antigen (e.g., a polypeptide) that is uniquely or differentially expressed on a tumor cell compared to a normal or non-IS neoplastic cell. In certain embodiments, a tumor antigen includes any polypeptide expressed by a tumor that is capable of activating or inducing an immune response via an antigen recognizing receptor (e.g., CD19, MUC-16) or capable of suppressing an immune response via receptor-ligand binding (e.g., CD47, PD-L1/L2, B7.1/2).

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

Other aspects of the presently disclosed subject matter are described in the following disclosure and are within the ambit of the presently disclosed subject matter.

2. HLA-Independent T Cell Receptor (HI-TCR)

The present disclosure provides an HI-TCR that binds to an antigen of interest in an HLA-independent manner. In certain non-limiting embodiments, binding of the antigen is capable of activating an immunoresponsive cell comprising the HI-TCR. In certain non-limiting embodiments, the HI-TCR comprises an antigen binding chain. In certain embodiments, the antigen binding chain comprises an extracellular antigen-binding domain. In certain embodiments, the extracellular antigen-binding domain is derived from a scFv, Fab, or antibody of murine, human or camelid (e.g., lama) origin. In certain embodiments, the antigen binding chain further comprises a constant domain.

2.1. Antigens

In certain embodiments, the HI-TCR binds to a tumor antigen. Any tumor antigen (antigenic peptide) can be used in the tumor-related embodiments described herein. Sources of antigen include, but are not limited to, cancer proteins. The antigen can be expressed as a peptide or as an intact protein or portion thereof. The intact protein or a portion thereof can be native or mutagenized. Non-limiting examples of tumor antigens include carbonic anhydrase IX (CAIX), carcinoembryonic antigen (CEA), CD8, CD7, CD10, CD19, CD20, CD22, CD30, CD33, CLL1, CD34, CD38, CD41, CD44, CD49f, CD56, CD74, CD133, CD138, CD123, CD44V6, an antigen of a cytomegalovirus (CMV) infected cell (e.g., a cell surface antigen), epithelial glycoprotein-2 (EGP-2), epithelial glycoprotein-40 (EGP-40), epithelial cell adhesion molecule (EpCAM), receptor tyrosine-protein kinases erb-B2,3,4 (erb-B2,3,4), folate-binding protein (FBP), fetal acetylcholine receptor (AChR), folate receptor-α, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis Y (LeY), L1 cell adhesion molecule (L1CAM), melanoma antigen family A, 1 (MAGE-A1), Mucin 16 (MUC16), Mucin 1 (MUC1), Mesothelin (MSLN), ERBB2, MAGEA3, p53, MART1, GP100, Proteinase3 (PR1), Tyrosinase, Survivin, hTERT, EphA2, NKG2D ligands, cancer-testis antigen NY-ESO-1, oncofetal antigen (h5T4), prostate stem cell antigen (PSCA), prostate-specific membrane antigen (PSMA), ROR1, tumor-associated glycoprotein 72 (TAG-72), vascular endothelial growth factor R2 (VEGF-R2), and Wilms tumor protein (WT-1), BCMA, NKCS1, EGF1R, EGFR-VIII, CD99, CD70, ADGRE2, CCR1, LILRB2, LILRB4, PRAME and ERBB.

In certain embodiments, the HI-TCR binds to CD19. In certain embodiments, the HI-TCR binds to a human CD19 polypeptide. In certain embodiments, the human CD19 polypeptide comprises the amino acid sequence set forth in SEQ ID NO: 11.

```
                                            [SEQ ID NO: 11]
PEEPLVVKVEEGDNAVLQCLKGTSDGPTQQLTWSRESPLK

PFLKLSLGLPGLGIHMRPLAIWLFIFNVSQQMGGFYLCQP

GPPSEKAWQPGWTVNVEGSGELFRWNVSDLGGLGCGLKNR

SSEGPSSPSGKLMSPKLYVWAKDRPEIWEGEPPCLPPRDS

LNQSLSQDLTMAPGSTLWLSCGVPPDSVSRGPLSWTHVHP

KGPKSLLSLELKDDRPARDMWVMETGLLLPRATAQDAGKY

YCHRGNLTMSFHLEITARPVLWHWLLRTGGWK.
```

In certain embodiments, the HI-TCR binds to the extracellular domain of a CD19 protein.

In certain embodiments, the HI-TCR binds to a pathogen antigen, e.g., for use in treating and/or preventing a pathogen infection or other infectious disease, for example, in an immunocompromised subject. Non-limiting examples of pathogen includes a virus, bacteria, fungi, parasite and protozoa capable of causing disease.

Non-limiting examples of viruses include, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Caliciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Naira viruses); Arena viridae (hemorrhagic fever viruses); Reoviridae (e.g. reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Non-limiting examples of bacteria include *Pasteurella, Staphylococci, Streptococcus, Escherichia coli, Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtherias, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, ickettsia*, and *Actinomyces israelli*.

In certain embodiments, the pathogen antigen is a viral antigen present in Cytomegalovirus (CMV), a viral antigen present in Epstein Barr Virus (EBV), a viral antigen present in Human Immunodeficiency Virus (HIV), or a viral antigen present in influenza virus.

2.2. Extracellular Antigen Binding Domain

In certain embodiments, the antigen binding chain comprises an extracellular antigen-binding domain. In certain embodiments, the extracellular antigen-binding domain specifically binds to an antigen, e.g., a tumor antigen or a pathogen antigen, e.g., those disclosed in Section 2.1. In certain embodiments, the extracellular antigen-binding domain is capable of dimerizing with another extracellular antigen-binding domain (e.g., forming a fragment variable (Fv)), wherein the dimerized antigen-binding domains (e.g., an Fv) specifically bind to an antigen, e.g., a tumor antigen or a pathogen antigen.

In certain embodiments, the extracellular antigen-binding domain comprises a ligand for a cell-surface receptor. In certain embodiments, the extracellular antigen-binding domain comprises a receptor for a cell surface ligand.

In certain embodiments, the extracellular antigen-binding domain specifically binds to an antigen, e.g., a tumor antigen or a pathogen antigen. In certain embodiments, the antigen binding chain is capable of forming a dimer with another antigen binding chain. In certain embodiments, the HI-TCR comprises a heterodimer comprising two different antigen binding chains. In certain embodiments, the HI-TCR comprises a homodimer comprising two identical antigen binding chains. In certain embodiments, the antigen binding chains dimerize through one or more disulfide-links. In certain embodiments, the antigen binding chain is capable of forming a trimer or oligomer with one or more identical or different antigen binding chains. In certain embodiments, the extracellular antigen-binding domain is capable of dimerizing with another extracellular antigen-binding domain (e.g., forming a fragment variable (Fv)), wherein the dimerized antigen-binding domains (e.g., a Fv) specifically bind to an antigen, e.g., a tumor antigen or a pathogen antigen.

In certain non-limiting embodiments, the extracellular antigen-binding domain of the HI-TCR (for example, an Fv or an analog thereof) binds to an antigen with a dissociation constant ($K_d$) of about $2 \times 10^{-7}$ M or less. In certain embodiments, the $K_d$ is about $2 \times 10^{-7}$ M or less, about $1 \times 10^{-7}$ M or less, about $9 \times 10^{-8}$ M or less, about $1 \times 10^{-8}$ M or less, about $9 \times 10^{-9}$ M or less, about $5 \times 10^{-9}$ M or less, about $4 \times 10^{-9}$ M or less, about $3 \times 10^{-9}$ or less, about $2 \times 10^{-9}$ M or less, or about $1 \times 10^{-9}$ M or less. In certain non-limiting embodiments, the $K_d$ is about $3 \times 10^{-9}$ M or less. In certain non-limiting embodiments, the $K_d$ is from about $1 \times 10^{-9}$ M to about $3 \times 10^{-7}$ M. In certain non-limiting embodiments, the $K_d$ is from about $1.5 \times 10^{-9}$ M to about $3 \times 10^{-7}$ M. In certain non-limiting embodiments, the $K_d$ is from about $1.5 \times 10^{-9}$ M to about $2.7 \times 10^{-7}$ M.

Binding of the extracellular antigen-binding domain (for example, a Fv or an analog thereof) can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or an Fv) specific for the complex of interest. For example, the Fv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the extracellular antigen-binding domain is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet).

In certain embodiments, the extracellular antigen-binding domain comprises an antigen binding portion of a TCR.

In certain embodiments, the extracellular antigen-binding domain comprises an antigen binding portion of an antibody or a fragment thereof. In certain embodiments, the extracellular antigen-binding domain comprises a heavy chain variable region ($V_H$) and/or a light chain variable region ($V_L$) of an antibody. In certain embodiments, the extracellular antigen-binding domain comprises a single-chain variable fragment (scFv). In certain embodiments, the extracellular antigen-binding domain comprises a heavy chain-only antibodies (VHH). In certain embodiments, the extracellular antigen-binding domain comprises a Fab, which is optionally crosslinked. In certain embodiments, the extracellular antigen-binding domain comprises a F(ab)$_2$. In certain embodiments, any of the foregoing molecules can be comprised in a fusion protein with a heterologous sequence to form the extracellular antigen-binding domain.

In certain embodiments, the extracellular antigen-binding domain comprises a heavy chain variable region ($V_H$) and/or a light chain variable region ($V_L$) of an antibody, wherein the $V_H$ or the $V_L$ is capable of dimerizing with another extracellular antigen-binding domain comprising a VL or a VH (e.g., forming a fragment variable (Fv)). In certain embodiments, the Fv is a human Fv. In certain embodiments, the Fv is a humanized Fv. In certain embodiments, the Fv is a murine Fv. In certain embodiments, the Fv is identified by screening a Fv phage library with an antigen-Fc fusion protein.

Additional extracellular antigen-binding domains targeting an interested antigen can be obtained by sequencing an existing scFv or a Fab region of an existing antibody targeting the same antigen.

In certain embodiments, the dimerized extracellular antigen-binding domain of a presently disclosed HI-TCR is a murine Fv. In certain embodiments, the dimerized extracellular antigen-binding domain is an Fv that binds to a human CD19 polypeptide. In certain embodiments, the extracellular antigen-binding domain is an Fv, which comprises the amino acid sequence of SEQ ID NO: 9 and specifically binds to a human CD19 polypeptide (e.g., a human CD19 polypeptide comprising the amino acid sequence set forth in SEQ ID NO: 11). In certain embodiments, the nucleotide sequence encoding the amino acid sequence of SEQ ID NO: 9 is set forth in SEQ ID NO: 10.

In certain embodiments, the Fv comprises a heavy chain variable region ($V_H$) comprising the amino acid sequence set forth in SEQ ID NO: 7. In certain embodiments, the Fv comprises a light chain variable region ($V_L$) comprising the amino acid sequence set forth in SEQ ID NO: 8. In certain embodiments, the Fv comprises $V_H$ comprising the amino acid sequence set forth in SEQ ID NO: 7 and a $V_L$ comprising the amino acid sequence set forth in SEQ ID NO: 8. In certain embodiments, the extracellular antigen-binding domain comprises a $V_H$ comprising an amino acid sequence that is at least about 80% (e.g., at least about 85%, at least about 90%, or at least about 95%) homologous or identical to SEQ ID NO: 7. For example, the extracellular antigen-binding domain comprises a $V_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to SEQ ID NO: 7. In certain embodiments, the extracellular antigen-binding domain comprises a $V_H$ comprising the amino sequence set forth in SEQ ID NO: 7. In certain embodiments, the extracellular antigen-binding domain comprises a $V_L$ comprising an amino acid sequence that is at least about 80% (e.g., at least about 85%, at least about 90%, or at least about 95%) homologous to SEQ ID NO: 8. For example, the extracellular antigen-binding domain comprises a $V_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to SEQ ID NO: 8. In certain embodiments, the extracellular antigen-binding domain comprises a $V_L$ comprising the amino acid sequence set forth in SEQ ID NO: 8. In certain embodiments, the extracellular antigen-binding domain comprises a $V_H$ comprising an amino acid sequence that is at least about 80% (e.g., at least about 85%, at least about 90%, or at least about 95%) homologous to SEQ ID NO: 7, and a $V_L$ comprising an amino acid sequence that is at least about 80% (e.g., at least about 85%, at least about 90%, or at least about 95%) homologous or identical to SEQ ID NO: 8. In certain embodiments, the extracellular antigen-binding domain comprises a $V_H$ comprising the amino acid sequence set forth in SEQ ID NO: 7 and a $V_L$ comprising the amino acid sequence set forth in SEQ ID NO: 8.

In certain embodiments, the Fv comprises a heavy chain variable region (V$_H$) comprising the amino acid sequence set forth in SEQ ID NO: 44. In certain embodiments, the Fv comprises a light chain variable region (V$_L$) comprising the amino acid sequence set forth in SEQ ID NO: 45. In certain embodiments, the Fv comprises V$_H$ comprising the amino acid sequence set forth in SEQ ID NO: 44 and a V$_L$ comprising the amino acid sequence set forth in SEQ ID NO: 45. In certain embodiments, the extracellular antigen-binding domain comprises a V$_H$ comprising an amino acid sequence that is at least about 80% (e.g., at least about 85%, at least about 90%, or at least about 95%) homologous or identical to SEQ ID NO: 44. For example, the extracellular antigen-binding domain comprises a V$_H$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to SEQ ID NO: 44. In certain embodiments, the extracellular antigen-binding domain comprises a V$_H$ comprising the amino sequence set forth in SEQ ID NO: 44. In certain embodiments, the extracellular antigen-binding domain comprises a V$_L$ comprising an amino acid sequence that is at least about 80% (e.g., at least about 85%, at least about 90%, or at least about 95%) homologous to SEQ ID NO: 45. For example, the extracellular antigen-binding domain comprises a V$_L$ comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to SEQ ID NO: 45. In certain embodiments, the extracellular antigen-binding domain comprises a V$_L$ comprising the amino acid sequence set forth in SEQ ID NO: 45. In certain embodiments, the extracellular antigen-binding domain comprises a V$_H$ comprising an amino acid sequence that is at least about 80% (e.g., at least about 85%, at least about 90%, or at least about 95%) homologous to SEQ ID NO: 44, and a V$_L$ comprising an amino acid sequence that is at least about 80% (e.g., at least about 85%, at least about 90%, or at least about 95%) homologous or identical to SEQ ID NO: 45. In certain embodiments, the extracellular antigen-binding domain comprises a V$_H$ comprising the amino acid sequence set forth in SEQ ID NO: 44 and a V$_L$ comprising the amino acid sequence set forth in SEQ ID NO: 45.

In certain embodiments, the extracellular antigen-binding domain comprises a V$_H$ CDR1 comprising the amino acid sequence set forth in SEQ ID NO: 1, or a conservative modification thereof, a V$_H$ CDR2 comprising the amino acid sequence set forth in SEQ ID NO: 2 or a conservative modification thereof, and a V$_H$ CDR3 comprising the amino acid sequence set forth in SEQ ID NO: 3, a conservative modification thereof. In certain embodiments, the extracellular antigen-binding domain comprises a V$_H$ CDR1 comprising the amino acid sequence set forth in SEQ ID NO: 1, a V$_H$ CDR2 comprising the amino acid sequence set forth in SEQ ID NO: 2, and a V$_H$ CDR3 comprising the amino acid sequence set forth in SEQ ID NO: 3. In certain embodiments, the extracellular antigen-binding domain comprises a V$_L$ CDR1 comprising the amino acid sequence set forth in SEQ ID NO: 4 or a conservative modification thereof, a V$_L$ CDR2 comprising the amino acid sequence set forth in SEQ ID NO: 5 or a conservative modification thereof, and a V$_L$ CDR3 comprising the amino acid sequence set forth in SEQ ID NO: 6 or a conservative modification thereof. In certain embodiments, the extracellular antigen-binding domain comprises a V$_L$ CDR1 comprising the amino acid sequence set forth in SEQ ID NO: 4, a V$_L$ CDR2 comprising the amino acid sequence set forth in SEQ ID NO: 5, and a V$_L$ CDR3 comprising the amino acid sequence set forth in SEQ ID NO: 6. In certain embodiments, the extracellular antigen-binding domain comprises a V$_H$ CDR1 comprising the amino acid sequence set forth in SEQ ID NO: 1 or a conservative modification thereof, a V$_H$ CDR2 comprising the amino acid sequence set forth in SEQ ID NO: 2 or a conservative modification thereof, a V$_H$ CDR3 comprising the amino acid sequence set forth in SEQ ID NO: 3, a conservative modification thereof, a V$_L$ CDR1 comprising the amino acid sequence set forth in SEQ ID NO: 4 or a conservative modification thereof, a V$_L$ CDR2 comprising the amino acid sequence set forth in SEQ ID NO: 5 or a conservative modification thereof, and a V$_L$ CDR3 comprising the amino acid sequence set forth in SEQ ID NO: 6 or a conservative modification thereof. In certain embodiments, the extracellular antigen-binding domain comprises a V$_H$ CDR1 comprising amino acids having the sequence set forth in SEQ ID NO: 1, a V$_H$ CDR2 comprising the amino acid sequence set forth in SEQ ID NO: 2, a V$_H$ CDR3 comprising the amino acid sequence set forth in SEQ ID NO: 3, a V$_L$ CDR1 comprising the amino acid sequence set forth in SEQ ID NO: 4, a V$_L$ CDR2 comprising the amino acid sequence set forth in SEQ ID NO: 5 and a V$_L$ CDR3 comprising the amino acid sequence set forth in SEQ ID NO: 6.

TABLE 1

| | | anti-human CD19scFv (SJ25C1) | | |
|---|---|---|---|---|
| CDRs | | 1 | 2 | 3 |
| VH | a.a. | GYAFSS [SEQ ID NO: 1] | YPGDGD [SEQ ID NO: 2] | KTIS SWDF [SEQ ID NO: 3] |
| VL | a.a. | KASQNV GTNVA [SEQ ID NO: 4] | SATYRN [SEQ ID NO: 5] | QQYNR YPYT [SEQ ID NO: 6] |
| Full VH | | EVKLQQSGAE LVRPGSSVKI SCKASGYAFS SYWMNWVKQR PGQGLEWIGQ IYPGDGDTNY NGKFKGQATL TADKSSSTAY MQLSGLTSED SAVYFCARKT ISSVVDFYFD YWGQGTTVTV SS [SEQ ID NO: 7] EVKLQQSGAELVRPGSSVKISCKASGYAFSSY WMNWVKQRPGQGLEWIGQIYPGDGDTNYNGKF KGQATLTADKSSSTAYMQLSGLTSEDSAVYFC ARKTISSWDFYFDYWGQGT TVTV [SEQ ID NO: 44] | | |
| Full VL | | DIELTQSPKF MSTSVGDRVS VTCKASQNVG TNVAWYQQKP GQSPKPLIYS ATYRNSGVPD RFTGSGSGTD FTLTITNVQS KDLADYFCQQ YNRYPYTSGG GTKLEIKR [SEQ ID NO: 8] DIELTQSPKFMSTSVGDRVSVTCKASQNVGTN VAWYQQKPGQSPKPLIYSATYRNSGVPDRFTG SGSGTDFTLTITNVQSKDLADYFCQQYNRYPY TSGGGTKLEI [SEQ ID NO: 45] | | |
| scFv | | MALPVTALLL PLALLLHAEV KLQQSGAELV RPGSSVKISC KASGYAFSSY WMNWVKQRPG QGLEWIGQIY PGDGDTNYNG KFKGQATLTA DKSSSTAYMQ LSGLTSEDSA VYFCARKTIS SVVDFYFDYW GQGTTVTVSS GGGGSGGGGS GGGGSDIELT QSPKFMSTSV GDRVSVTCKA | | |

TABLE 1-continued anti-human CD19scFv (SJ25C1)

| CDRs | 1 | 2 | 3 |
|---|---|---|---|
| | SQNVGTNVAW | YQQKPGQSPK | PLIYSATYRN |
| | SGVPDRFTGS | GSGTDFTLTI | TNVQSKDLAD |
| | YFCQQYNRYP | YTSGGGTKLE | IKR |
| | [SEQ ID NO: 9] | | |

| DNA | ATGGCTCTCCCAGTGACTGCCCTACTGCTTCC |
|---|---|
| | CCTAGCGCTTCTCCTGCATGCAGAGGTGAAGC |
| | TGCAGCAGTCTGGGGCTGAGCTGGTGAGGCCT |
| | GGGTCCTCAGTGAAGATTTCCTGCAAGGCTTC |
| | TGGCTATGCATTCAGTAGCTACTGGATGAACT |
| | GGGTGAAGCAGAGGCCTGGACAGGGTCTTGAG |
| | TGGATTGGACAGATTTATCCTGGAGATGGTGA |
| | TACTAACTACAATGGAAAGTTCAAGGGTCAAG |
| | CCACACTGACTGCAGACAAATCCTCCAGCACA |
| | GCCTACATGCAGCTCAGCGGCCTAACATCTGA |
| | GGACTCTGCGGTCTATTTCTGTGCAAGAAAGA |
| | CCATTAGTTCGGTAGTAGATTTCTACTTTGAC |
| | TACTGGGGCCAAGGGACCACGGTCACCGTCTC |
| | CTCAGGTGGAGGTGGATCAGGTGGAGGTGGAT |
| | CTGGTGGAGGTGGATCTGACATTGAGCTCACC |
| | CAGTCTCCAAAATTCATGTCCACATCAGTAGG |
| | AGACAGGGTCAGCGTCACCTGCAAGGCCAGTC |
| | AGAATGTGGGTACTAATGTAGCCTGGTATCAA |
| | CAGAAACCAGGACAATCTCCTAAACCACTGAT |
| | TTACTCGGCAACCTACCGGAACAGTGGAGTCC |
| | CTGATCGCTTCACAGGCAGTGGATCTGGGACA |
| | GATTTCACTCTCACCATCACTAACGTGCAGTC |
| | TAAAGACTTGGCAGACTATTTCTGTCAACAAT |
| | ATAACAGGTATCCGTACACGTCCGGAGGGGGG |
| | ACCAAGCTGGAGATCAAACGG |
| | [SEQ ID NO: 10] |

As used herein, the term "a conservative sequence modification" refers to an amino acid modification that does not significantly affect or alter the binding characteristics of the presently disclosed HI-TCR comprising the amino acid sequence. Conservative modifications can include amino acid substitutions, additions and deletions. Modifications can be introduced into the Fv of the presently disclosed HI-TCR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered.

The $V_H$ and/or $V_L$ amino acid sequences having at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology to a specific sequence (e.g., SEQ ID NOs: 7, and 8) may contain substitutions (e.g., conservative substitutions), insertions, or deletions relative to the specified sequence(s), but retain the ability to bind to a target antigen (e.g., CD19). In certain embodiments, a total of 1 to 10 amino acids are substituted, inserted and/or deleted in a specific sequence (e.g., SEQ ID NOs: 7, and 8). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from the group consisting of SEQ ID NOs: 7, and 8, including post-translational modifications of that sequence (SEQ ID NOs: 7 and 8).

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the specified sequences (e.g., heavy and light chain variable region sequences of scFv m903, m904, m905, m906, and m900) disclosed herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

2.3. Constant Domain

In certain embodiments, the antigen binding chain further comprises a constant domain. In certain embodiments, the constant domain comprises a hinge/spacer region and a transmembrane domain. In certain embodiments, the constant domain is capable of forming a homodimer or a heterodimer with another constant domain. In certain embodiments, the constant domain dimerizes through one or more disulfide-links. In certain embodiments, the antigen binding chain is capable of forming a trimer or oligomer with one or more identical or different constant domains.

In certain non-limiting embodiments, the constant domain comprises a T cell receptor constant region, e.g., T cell receptor alpha constant region (TRAC), T cell receptor beta constant region (TRBC, e.g., TRBC1 or TRBC2), T cell receptor gamma constant region (TRGC, e.g., TRGC1 or TRGC2), T cell receptor delta constant region (TRDC) or any variants or functional fragments thereof.

In certain embodiments, the constant domain of a presently disclosed HI-TCR comprises a native or modified TRAC peptide. In certain embodiments, the TRAC polypeptide comprises an amino acid sequence that is at least about 80%, at least about 85%, at least about 90%, at least about 95%, at least about 96%, at least about 97%, at least about 98%, at least about 99% or at least about 100% homologous or identical to the amino acid sequence set forth in SEQ ID NO:38, which is provided below), or fragments thereof, and/or may optionally comprise up to one or up to two or up to three conservative amino acid substitutions.

[SEQ ID NO: 38]
IQNPDPAVYQLRDSKSSDKSVCLFTDFDSQTNVSQSKDSD

VYITDKTVLDMRSMDFKSNSAVAWSNKSDFACANAFNNSI

IPEDTFFPSPESSCDVKLVEKSFETDTNLNFQNLSVIGFR

ILLLKVAGFNLLMTLRLWSS

In certain embodiments, the TRAC polypeptide has an amino acid sequence that is at least about 80%, at least about 85%, at least about 90%, at least about 95%, at least about 96%, at least about 97%, at least about 98%, at least about 99% or at least about 100% homologous or identical to the amino acid sequence encoded by a transcript expressed by the gene of NCBI Genbank ID: 28755, NG_001332.3, range 925603 to 930229 (SEQ ID NO:29, which is provided below), or fragments thereof, and/or may optionally comprise up to one or up to two or up to three conservative amino acid substitutions.

```
                                      [SEQ ID NO: 29]
   1 atatccagaa ccctgaccct gccgtgtacc agctgagaga ctctaaatcc agtgacaagt 61 ctgtctgcct attcaccgat tttgattctc aaacaaatgt gtcacaaagt aaggattctg 121 atgtgtatat cacagacaaa actgtgctag acatgaggtc tatggacttc aagagcaaca 181 gtgctgtggc ctggagcaac aaatctgact ttgcatgtgc aaacgccttc aacaacagca 241 ttattccaga agacaccttc ttccccagcc caggtaaggg cagctttggt gccttcgcag 301 gctgtttcct tgcttcagga atggccaggt tctgcccaga gctctggtca atgatgtcta 361 aaactcctct gattggtggt ctcggcctta tccattgcca ccaaaaccct cttttttacta 421 agaaacagtg agccttgttc tggcagtcca gagaatgaca cgggaaaaaa gcagatgaag 481 agaaggtggc aggagagggc acgtggccca gcctcagtct ctccaactga gttcctgcct 541 gcctgccttt gctcagactg tttgccctt actgctcttc taggcctcat tctaagcccc 601 ttctccaagt tgcctctcct tatttctccc tgtctgccaa aaaatctttc ccagctcact 661 aagtcagtct cacgcagtca ctcattaacc caccaatcac tgattgtgcc ggcacatgaa 721 tgcaccaggt gttgaagtgg aggaattaaa aagtcagatg aggggtgtgc ccagaggaag 781 caccattcta gttggggggag cccatctgtc agctgggaaa agtccaaata acttcagatt 841 ggaatgtgtt ttaactcagg gttgagaaaa cagctacctt caggacaaaa gtcagggaag 901 ggctctctga agaaatgcta cttgaagata ccagccctac caagggcagg gagaggaccc 961 tatagaggcc tgggacagga gctcaatgag aaaggagaag agcagcaggc atgagttgaa 1021 tgaaggaggc agggccgggt cacagggcct tctaggccat gagagggtag acagtattct 1081 aaggacgcca gaaagctgtt gatcggcttc aagcagggga gggacaccta atttgctttt 1141 ctttttttt ttttttttt ttttttttt tgagatggag ttttgctctt gttgcccagg 1201 ctggagtgca atggtgcatc ttggctcact gcaacctccg cctcccaggt tcaagtgatt 1261 ctcctgcctc agcctcccga gtagctgaga ttacaggcac ccgccaccat gcctggctaa 1321 ttttttgtat ttttagtaga cagggttt cactatgttg gccaggctgg tctcgaactc 1381 ctgacctcag gtgatccacc cgcttcagcc tcccaaagtg ctgggattac aggcgtgagc 1441 caccacaccc ggcctgcttt tcttaaagat caatctgagt gctgtacgga gagtgggttg 1501 taagccaaga gtagaagcag aaagggagca gttgcagcag agagatgatg gaggcctggg
```

-continued

```
1561  cagggtggtg gcagggaggt aaccaacacc
      attcaggttt caaaggtaga accatgcagg
1621  gatgagaaag caaagagggg atcaaggaag
      gcagctggat tttggcctga gcagctgagt
1681  caatgatagt gccgtttact aagaagaaac
      caaggaaaaa atttggggtg cagggatcaa
1741  aacttttcgg aacatatgaa agtacgtgtt
      tatactcttt atggcccttg tcactatgta
1801  tgcctcgctg cctccattgg actctagaat
      gaagccaggc aagagcaggg tctatgtgtg
1861  atggcacatg tggccagggt catgcaacat
      gtactttgta caaacagtgt atattgagta
1921  aatagaaatg gtgtccagga gccgaggtat
      cggtcctgcc agggccaggg gctctcccta
1981  gcaggtgctc atatgctgta agttccctcc
      agatctctcc acaaggaggc atggaaaggc
2041  tgtagttgtt cacctgccca agaactagga
      ggtctggggt gggagagtca gcctgctctg
2101  gatgctgaaa gaatgtctgt ttttcctttt
      agaaagttcc tgtgatgtca agctggtcga
2161  gaaaagcttt gaaacaggta agacagggct
      ctagcctggg tttgcacagg attgcggaag
2221  tgatgaaccc gcaataaccc tgcctggatg
      agggagtggg aagaaattag tagatgtggg
2281  aatgaatgat gaggaatgga aacagcggtt
      caagacctgc ccagagctgg gtggggtctc
2341  tcctgaatcc ctctcaccat ctctgacttt
      ccattctaag cactttgagg atgagtttct
2401  agcttcaata gaccaaggac tctctcctag
      gcctctgtat tcctttcaac agctccactg
2461  tcaagagagc cagagagagc ttctgggtgg
      cccagctgtg aaatttctga gtcccttagg
2521  gatagcccta acgaaccag atcatcctga
      ggacagccaa gaggttttgc cttctttcaa
2581  gacaagcaac agtactcaca taggctgtgg
      gcaatggtcc tgtctctcaa gaatcccctg
2641  ccactcctca cacccaccct gggcccatat
      tcatttccat ttgagttgtt cttattgagt
2701  catccttcct gtggtagcgc aactcactaa
      ggggcccatc tggacccgag gtattgtgat
2761  gataaattct gagcacctac cccatcccca
      gaagggctca gaaataaaat aagagccaag
2821  tctagtcggt gtttcctgtc ttgaaacaca
      atactgttgg ccctggaaga atgcacagaa
2881  tctgtttgta agggatatg cacagaagct
      gcaagggaca ggaggtgcag gagctgcagg
2941  cctcccccac ccagcctgct ctgccttggg
      gaaaaccgtg ggtgtgtcct gcaggccatg
3001  caggcctggg acatgcaagc ccataaccgc
      tgtggcctct tggttttaca gatacgaacc
3061  taaactttca aaacctgtca gtgattgggt
      tccgaatcct cctcctgaaa gtggccgggt
3121  ttaatctgct catgacgctg cggctgtggt
      ccagctgagg tgaggggcct tgaagctggg
3181  agtggggttt agggacgcgg gtctctgggt
      gcatcctaag ctctgagagc aaacctccct
3241  gcagggtctt gcttttaagt ccaaagcctg
      agcccaccaa actctcctac ttcttcctgt
3301  tacaaattcc tcttgtgcaa taataatggc
      ctgaaacgct gtaaaatatc ctcatttcag
3361  ccgcctcagt tgcacttctc ccctatgagg
      taggaagaac agttgtttag aaacgaagaa
3421  actgaggccc cacagctaat gagtggagga
      agagagacac ttgtgtacac cacatgcctt
3481  gtgttgtact tctctcaccg tgtaacctcc
      tcatgtcctc tctccccagt acggctctct
3541  tagctcagta gaaagaagac attacactca
      tattacaccc caatcctggc tagagtctcc
3601  gcaccctcct cccccagggt ccccagtcgt
      cttgctgaca actgcatcct gttccatcac
3661  catcaaaaaa aaactccagg ctgggtgcgg
      gggctcacac ctgtaatccc agcactttgg
3721  gaggcagagg caggaggagc acaggagctg
      gagaccagcc tgggcaacac agggagaccc
3781  cgcctctaca aaaagtgaaa aaattaacca
      ggtgtggtgc tgcacacctg tagtcccagc
3841  tacttaagag gctgagatgg gaggatcgct
      tgagccctgg aatgttgagg ctacaatgag
3901  ctgtgattgc gtcactgcac tccagcctgg
      aagacaaagc aagatcctgt ctcaaataat
```

-continued

```
3961 aaaaaaaata agaactccag ggtacatttg
     ctcctagaac tctaccacat agcccaaac
4021 agagccatca ccatcacatc cctaacagtc
     ctgggtcttc ctcagtgtcc agcctgactt
4081 ctgttcttcc tcattccaga tctgcaagat
     tgtaagacag cctgtgctcc ctcgctcctt
4141 cctctgcatt gcccctcttc tccctctcca
     aacagaggga actctcctac ccccaaggag
4201 gtgaaagctg ctaccacctc tgtgccccc
     cggcaatgcc accaactgga tcctacccga
4261 atttatgatt aagattgctg aagagctgcc
     aaacactgct gccaccccct ctgttcccctt
4321 attgctgctt gtcactgcct gacattcacg
     gcagaggcaa ggctgctgca gcctcccctg
4381 gctgtgcaca ttccctcctg ctccccagag
     actgcctccg ccatcccaca gatgatggat
4441 cttcagtggg ttctcttggg ctctaggtcc
     tgcagaatgt tgtgaggggt ttatttttt
4501 ttaatagtgt tcataaagaa atacatagta
     ttcttcttct caagacgtgg ggggaaatta
4561 tctcattatc gaggccctgc tatgctgtgt
     atctgggcgt gttgtatgtc ctgctgccga
4621 tgccttc
```

In accordance with the presently disclosed subject matter, an "TRAC nucleic acid molecule" refers to a polynucleotide encoding an TRAC polypeptide.

In certain embodiments, the constant domain of a presently disclosed HI-TCR comprises a native or modified TRBC peptide. In certain embodiments, the constant domain of a presently disclosed HI-TCR comprises a native or modified TRBC2 peptide. In certain embodiments, the TRBC2 polypeptide comprises an amino acid sequence that is at least about 80%, at least about 85%, at least about 90%, at least about 95%, at least about 96%, at least about 97%, at least about 98%, at least about 99% or at least about 100% homologous or identical to the amino acid sequence set forth in SEQ ID NO:39, which is provided below, or fragments thereof, and/or may optionally comprise up to one or up to two or up to three conservative amino acid substitutions.

[SEQ ID NO: 39]
DLKNVEPPEVAVFEPSEAEISHTQKATLVCLATGFYPDHV

ELSWWVNGKEVHSGVSTDPQPLKEQPALNDSRYCLSSRLR

VSATFWQNPRNHFRCQVQFYGLSENDEWTQDRAKPVTQIV

SAEAWGRADCGFTSESYQQGVLSATILYEILLGKATLYAV

LVSALVLMAMVKRKDSRG

In certain embodiments, the constant domain of a presently disclosed HI-TCR comprises a native or modified TRBC1 peptide. In certain embodiments, the TRBC1 polypeptide comprises an amino acid sequence that is at least about 80%, at least about 85%, at least about 90%, at least about 95%, at least about 96%, at least about 97%, at least about 98%, at least about 99% or at least about 100% homologous or identical to the amino acid sequence set forth in SEQ ID NO:40, which is provided below, or fragments thereof, and/or may optionally comprise up to one or up to two or up to three conservative amino acid substitutions.

[SEQ ID NO: 40]
DLNKVFPPEV AVFEPSEAEI SHTQKATLVC

LATGFFPDHV ELSWWVNGKE VHSGVSTDPQ

PLKEQPALND SRYCLSSRLR VSATFWQNPR

NHFRCQVQFY GLSENDEWTQ DRAKPVTQIV

SAEAWGRADC GFTSVSYQQG VLSATILYEI

LLGKATLYAV LVSALVLMAM VKRKDF

In certain embodiments, the TRBC polypeptide has an amino acid sequence that is at least about 80%, at least about 85%, at least about 90%, at least about 95%, at least about 96%, at least about 97%, at least about 98%, at least about 99% or at least about 100% homologous or identical to the amino acid sequence encoded by a transcript expressed by a gene of NCBI Genbank ID: 28639, NG_001333.2, range 645749 to 647196 (TRBC1, SEQ ID NO: 30), NCBI Genbank ID: 28638, NG_001333.2 range 655095 to 656583 (TRBC2, SEQ ID NO:31) or fragments thereof, and/or may optionally comprise up to one or up to two or up to three conservative amino acid substitutions.

```
                                        [SEQ ID NO: 30]
  1 aggacctgaa caaggtgttc ccacccgagg
    tcgctgtgtt tgagccatca gaagcagaga
 61 tctcccacac ccaaaaggcc acactggtgt
    gcctggccac aggcttcttc cccgaccacg
121 tggagctgag ctggtgggtg aatgggaagg
    aggtgcacag tggggtcagc acagaccccg
181 agccctcaa ggagcagccc gcctcaatg
    actccagata ctgcctgagc agccgcctga
241 gggtctcggc caccttctgg cagaacccc
    gcaaccactt ccgctgtcaa gtccagttct
301 acgggctctc ggagaatgac gagtggaccc
    aggatagggc caaacccgtc acccagatcg
361 tcagcgccga ggcctggggt agagcaggtg
    agtgggcct ggggagatgc ctggaggaga
421 ttaggtgaga ccagctacca gggaaaatgg
    aaagatccag gtagcagaca agactagatc
481 caaaagaaa ggaaccagcg cacaccatga
    aggagaattg ggcacctgtg gttcattctt
```

```
541 ctcccagatt ctcagcccaa cagagccaag
    cagctgggtc ccctttctat gtggcctgtg
601 taactctcat ctgggtggtg ccccccatcc
    ccctcagtgc tgccacatgc catggattgc
661 aaggacaatg tggctgacat ctgcatggca
    gaagaaagga ggtgctgggc tgtcaggaga
721 agctggtctg ggcctgggag tctgtgccaa
    ctgcaaatct gactttactt ttaattgcct
781 atgaaaataa ggtctctcat ttattttcct
    ctccctgctt tctttcagac tgtggcttta
841 cctcgggtaa gtaagccctt ccttttcctc
    tccctctctc atggttcttg acctagaacc
901 aaggcatgaa gaactcacag acactggagg
    gtggaggggtg ggagagacca gagctacctg
961 tgcacaggta cccacctgtc cttcctccgt
    gccaacagtg tcctaccagc aagggtcct
1021 gtctgccacc atcctctatg agatcctgct
     agggaaggcc acctgtatg ctgtgctggt
1081 cagcgccctt gtgttgatgg ccatggtaag
     caggagggca ggatggggcc agcaggctgg
1141 aggtgacaca ctgacaccaa gcacccagaa
     gtatagagtc cctgccagga ttggagctgg
1201 gcagtaggga gggaagagat ttcattcagg
     tgcctcagaa gataacttgc acctctgtag
1261 gatcacagtg gaagggtcat gctgggaagg
     agaagctgga gtcaccagaa aacccaatgg
1321 atgttgtgat gagccttact attgtgtgg
     tcaatgggcc ctactacttt ctctcaatcc
1381 tcacaactcc tggctcttaa taaccccaa
     aactttctct tctgcaggtc aagagaaagg
1441 atttctga
```

[SEQ ID NO: 31]
```
  1 aggacctgaa aaacgtgttc ccacccgagg
    tcgctgtgtt tgagccatca gaagcagaga
 61 tctcccacac ccaaaaggcc acactggtat
    gcctggccac aggcttctac cccgaccacg
121 tggagctgag ctggtgggtg aatgggaagg
    aggtgcacag tggggtcagc acagaccgc
181 agcccctcaa ggagcagccc gccctcaatg
    actccagata ctgcctgagc agccgcctga
```

```
241 gggtctcggc caccttctgg cagaacccc
    gcaaccactt ccgctgtcaa gtccagttct
301 acgggctctc ggagaatgac gagtggaccc
    aggatagggc caaacccgtc acccagatcg
361 tcagcgccga ggcctggggt agagcaggtg
    agtgggcct gggagatgc ctggaggaga
421 ttaggtgaga ccagctacca gggaaaatgg
    aaagatccag gtagcggaca agactagatc
481 cagaagaaag ccagagtgga caaggtggga
    tgatcaaggt tcacagggtc agcaaagcac
541 ggtgtgcact tcccccacca agaagcatag
    aggctgaatg gagcacctca agctcattct
601 tccttcagat cctgacacct tagagctaag
    ctttcaagtc tccctgagga ccagccatac
661 agctcagcat ctgagtggtg tgcatcccat
    tctcttctgg ggtcctggtt tcctaagatc
721 atagtgacca cttcgctggc actggagcag
    catgagggag acagaaccag ggctatcaaa
781 ggaggctgac tttgtactat ctgatatgca
    tgtgtttgtg gcctgtgagt ctgtgatgta
841 aggctcaatg tccttacaaa gcagcattct
    ctcatccatt tttcttcccc tgttttcttt
901 cagactgtgg cttcacctcc ggtaagtgag
    tctctccttt ttctctctat cttcgccgt
961 ctctgctctc gaaccagggc atggagaatc
    cacggacaca ggggcgtgag ggaggccaga
1021 gccacctgtg cacaggtgcc tacatgctct
     gttcttgtca acagagtctt accagcaagg
1081 ggtcctgtct gccaccatcc tctatgagat
     cttgctaggg aaggccacct tgtatgccgt
1141 gctggtcagt gccctcgtgc tgatggccat
     ggtaaggagg agggtgggat agggcagatg
1201 atggggggcag gggatggaac atcacacatg
     ggcataaagg aatctcagag ccagagcaca
1261 gcctaatata tcctatcacc tcaatgaaac
     cataatgaag ccagactggg gagaaaatgc
1321 agggaatatc acagaatgca tcatgggagg
     atggagacaa ccagcgagcc ctactcaaat
1381 taggcctcag agcccgcctc ccctgcccta
     ctcctgctgt gccatagccc ctgaaaccct
```

```
    1441 gaaaatgttc tctcttccac aggtcaagag aaaggattcc agaggctag
```

In accordance with the presently disclosed subject matter, an "TRBC nucleic acid molecule" refers to a polynucleotide encoding an TRBC polypeptide.

In certain embodiments, the constant domain of a presently disclosed HI-TCR comprises a native or modified TRGC peptide. In certain embodiments, the constant domain of a presently disclosed HI-TCR comprises a native or modified TRGC1 peptide. In certain embodiments, the TRGC1 polypeptide has an amino acid sequence that is at least about 85%, about 90%, about 95%, about 96%, about 97%, about 98%, about 99% or 100% homologous or identical to the amino acid sequence set forth in SEQ ID NO: 42, which is provided below.

```
                                          [SEQ ID NO: 42]
        DKQLDADVSP KPTIFLPSIA ETKLQKAGTY

LCLLEKFFPD VIKIHWQEKK SNTILGSQEG

NTMKINDTYM KFSWLTVPEK SLDKEHRCIV

RHENNKNGVD QEIIFPPIKT DVITMDPKDN

CSKDANDTLL LQLTNTSAYY MYLLLLLKSV

VYFAIITCCL LRRTAFCCNG EKS
```

In certain embodiments, the constant domain of a presently disclosed HI-TCR comprises a native or modified TRGC2 peptide. In certain embodiments, the TRGC2 polypeptide has an amino acid sequence that is at least about 85%, about 90%, about 95%, about 96%, about 97%, about 98%, about 99% or 100% homologous or identical to the amino acid sequence set forth in SEQ ID NO: 43, which is provided below.

```
                                          [SEQ ID NO: 43]
        DKQLDADVSP KPTIFLPSIA ETKLQKAGTY

LCLLEKFFPD IIKIHWQEKK SNTILGSQEG

NTMKINDTYM KFSWLTVPEE SLDKEHRCIV

RHENNKNGID QEIIFPPIKT DVTTVDPKYN

YSKDANDVIT MDPKDNWSKD ANDTLLLQLT

NTSAYYTYLL LLLKSVVYFA IITCCLLRRT

AFCCNGEKS
```

In certain embodiments, the TRGC polypeptide has an amino acid sequence that is at least about 85%, about 90%, about 95%, about 96%, about 97%, about 98%, about 99% or 100% homologous or identical to the amino acid sequence encoded by a transcript expressed by a gene of NCBI Genbank ID: 6966, NG_001336.2, range 108270 to 113860 (TRGC1, SEQ ID NO: 32), NCBI Genbank ID: 6967, NG_001336.2, range 124376 to 133924 (TRGC2, SEQ ID NO: 33) or fragments thereof, and/or may optionally comprise up to one or up to two or up to three conservative amino acid substitutions.

```
                                          [SEQ ID NO: 32]
       1 ataaacaact tgatgcagat gtttccccca agcccactat tttcttcct tcaattgctg 61 aaacaaagct ccagaaggct ggaacatacc tttgtcttct tgagaaattt ttccctgatg 121 ttattaagat acattggcaa gaaaagaaga gcaacacgat tctgggatcc caggagggga 181 acaccatgaa gactaacgac acatacatga aatttagctg gttaacggtg ccagaaaagt 241 cactggacaa agaacacaga tgtatcgtca gacatgagaa taataaaaac ggagttgatc 301 aagaaattat ctttcctcca ataaagacag gtatgtgttt acgcatatca tctgtcagaa 361 cacttctttg aaagtgaatg ctgcattttt tcctttcagt attaatgaaa aacaaacata 421 aatctttctt aaatattgtt acatttaatg gtagcataaa tgccctgcta cttttctata 481 gaattaaaat ggtataggtt ttggagaaaa caaaattgaa aaagttactg aaggtttgtc 541 agcctcagct ccattatcca aaataagaaa gtcacgtgct ggtttttagg gttgttagat 601 ggattaaaga aacaacatac acagaagcat ctagcaacgt gacacgtggt aaacgctcaa 661 aaagtgttct cccttctttt gatgacttta cttgatcagg aaataacata tatatgtctt 721 tcaggaatgt tctgcccaag caggagagtc actcacctca atcttgctac ccacaaagtt 781 taacctaaaa acaacgggtt cattgttgac aaaatgatgt ttatctgttg ttgacagaat 841 gatgtttatc taaaaacagt tccaattttc tatttccttt gctgagacac aaagggagg 901 caaatgtgca aagcttgagg gtagtcttac cactgtgctt aagtgttctg attttctag 961 tgatcagggc aaaataaaaa gtatagtaag ttccaaggca gtgaatatta tacaggagag 1021 aagttacagt tttataatgt gttttccttt acactaaatt ctaaaagtaa aaagtctttt 1081 ttttttttg acagagtttc actcttgttg cccaagcagg tgtgctatgg tatgatctca 1141 gctcactgca acctccacct cccgggttca agtgattctc ttacttcagc ctcccgacag
```

-continued

```
1201 gctgggattg caggcgcctg ccaccacacc
     tggctaattt ttgtgttttt agtagagatg
1261 gggtttcacc atgttggcca ggctggtctc
     aaattcctga cctcaagtga tccatccacc
1321 tcggcctcca agtgctggga ttatgggcgt
     cagccactgt gcccagccta aaagtaaaat
1381 gtctttcatg agcttcccaa ggcagctacg
     ttaaggagga cacttctctt aatgtcattc
1441 tacagtagat ttctaatgct ctttcttgga
     agtttgtttt tctgagaaaa gctaaaaata
1501 taacatggaa gtgatcatat tatataatca
     atgaagtgct tttcaaggag ataaaactaa
1561 tctggtccac acttgcaacc aaccttgatt
     gagagagaga gagaactcag gatacacttg
1621 aagatttat tatggggaac agttactta
     ttctttttac ctcaatcaat gcatggaaat
1681 aagtgatagt cattttcatt tatcttttaa
     taaatgaagt caccatgagg aaaataaaaa
1741 gacattgaaa acccattaaa gtcagccctt
     aaagatattt ggacatgcag acttgataac
1801 taacgtttgc attcttgaga cttacccaaa
     acccatacct caagtccaag ttttagaat
1861 tcatgaaata aagatctcag tgagtgcata
     aaattgcgca ccagaatcat atccgtatag
1921 acaagaacac atctactaga aaaataataa
     accaacacac caatgcaact gtgttttctt
1981 ctgttttaaa gtatgttgtc tttgtatgca
     tgtttgcttc ttcctttttt tttttaacat
2041 cacagataaa ttcaactctc acctcaggtt
     ttattgagag aactgtcaat gtgacttggc
2101 ctctgtcttt ctagtcccag aaagaattgc
     actgaaatct gagctcctgt aataaaaaca
2161 accatttgct gagagtaatt aacatactga
     aagagatttt cttagagtac acaatggtga
2221 cattatattg cctctttata aataactttc
     tatctatttc tgtggattat tcctacaaag
2281 tacttttcat atgtccaatt tcttttcttc
     ccctacaact actgtctgaa tactggctct
2341 gctatttgct gatatgattc tcggcaagtt
     gcctgcactt tttaaacttt atttcctcat
2401 tcagaacatg gggccataca taatacaact
     cacttcagtg ttattgggga attaaacaaa
2461 aaatgcatgg gaagcattta acatagtgcc
     tgacacaata atgagtactc agtagatgtt
2521 agctttttatt aatattgttg ttgttatgtc
     cagaaacact atacctccag aaaatcatgg
2581 gtacttgctg gggacattgg ggatatgcat
     gatttggaaa agaatgactg cttttttttgc
2641 ttagatgaga aattttttcta agccagactc
     cttcaaatat gtaagattct gttgtggatt
2701 caaggactga agaattctt ggccgagtgt
     ggtggcttat ccctgtaatc ccagcatttt
2761 gtgaggacaa ggcaggaaga ttgcttgagt
     ccaggagttt gaaaccagcc tgcgcaacat
2821 ggcgaaaccc tgtctctaca aaaaatacaa
     acattagctc ggagtgagtg ctgacatgtg
2881 cctgtactcc cagctactca gaaggctgag
     atggaggat ctcatgagcc tggggagttt
2941 gaggcttcag tgagccgtga tgacaccgta
     ctatactcca ctccagcctg ggtgacagtg
3001 agaccctgcc tcaaaaaaca aacaaacaaa
     caaacaaaac aaaattaatc ttttgctga
3061 tgtcatgtca gcagtgtgtg ttgaaggctg
     taaagcagcc atttgttcag tttattttttc
3121 cattgaacaa gtatttatca aaaacatact
     ttgtggcagt cactatgcta ggagctatga
3181 atacagaagg aaaagtaaat gctcttggat
     actacactcc agttgtgata aaaaagaaaa
3241 aatgtattct tcaccaactt caacatcttg
     atgtgcaaaa acataataca tgaattagat
3301 ctacctaatt acacagaatt agaccaattg
     tttctggaat tgtgggctca tatttttaat
3361 aactgtcctc ctgcctctct gtcgacaggt
     tttataaata ttcatttaat tacacacaca
3421 cacacgaaca attgactagt acttgctctc
     attcttctag atgtcatcac aatggatccc
3481 aaagacaatt gttcaaaaga tgcaaatggt
     aagcttttgt gtttttccct tcctcctgat
3541 catttttgttt tgaacttctc tggcttgaaa
     aatcagggaa tggatttttgc taggttggat
```

-continued

```
3601 gctgcagaat ggacctagtg atattttaaa
     ttagtccctc attttctagg agttgtatta
3661 acaaacctaa ctactgcttt ggggtatgag
     atgactgtaa attagagagg gtacagtggt
3721 atagtgatat gcttttaatt atttcaaaaa
     aaagatttta ttcattcatg tgtcttttt
3781 ctttttcttt tctttttttt ttttttttgg
     acagagtctt gctctgtcac ccaggctgga
3841 gtgcggtggc agtatctcag ctcaccacaa
     cctccgcctc ccggcttcaa gtgattctcc
3901 tgcctcagct tctcgagtag ctgggactac
     aggcgcgtgc caccatgccc ggctaatttt
3961 tgtatttta gtagagttgg ggtttcacca
     tgttggccag gatggcctcg aatttgtgac
4021 ctcgtgatct gcccctcgc cctcccgaac
     tgttgggatt acaggcgtga gtcactgtgc
4081 ccggcctcct gtcctgtctt ttgtttaatg
     actgggaaaa acatgatacc atgttgcttc
4141 tcgagttgtt ttgttttagt ctttggtctt
     tgctagtagc taataacacg aactagtgtt
4201 tatcaagtgc tttttacaca gaagggcttg
     ggctgtgttc tgcattttct tgtttaaccc
4261 tcttaaaact cctataaaat ggtacatatt
     tttctcccaa tttacagtcc cttaaagca
4321 aataattata aaaatcccta tacatgtcac
     acagctagat ctgggattc aaatcaggcc
4381 atcaaacaaa gagtttatgt acttagtaag
     ttttctgttc tttttctaca atagagtcag
4441 atagcaagaa attaccaagc caggaacctg
     aaacaaaacg gacatcatgt ggggctgggt
4501 gggtgcatgg gctttgcaga ctggactttc
     actccagctc ttttaatgat taggtgtaag
4561 tgacctacat tttgtgagca acagttttct
     catcagccaa caaagaataa ttacaccaga
4621 ttcacagtta ttgaagagat aaaggcatga
     atgtgagatg tctggcatag ggcatctcat
4681 ttagcagaca cagaatgagt acttgtttct
     ggcttttct ctctacatat gcacaaagaa
4741 tgcgactaga agcatgggct ctagccctgc
     tcaactttcc tctatttcca ataccaaggg
4801 gctctgactt aggctgccac accaggcaag
     gagggcagta ccacctcact tgaccaaggg
4861 cagggagtca cggacacatc acttcttgag
     atccttttcc acaccaagga ctgatgtttc
4921 tggaattctc actttatgaa gacaaaacat
     ataaatggaa atttctcag gtagagactc
4981 actcttgtag ctcattgagt aggcactagt
     ggtccacccc cactgtcttt acttattcct
5041 tgacatcaca tatctcttgc aaaacctcaa
     ataatattaa atgcaatcac ccaataatag
5101 catagccata attagaggca tttaggaaag
     acaggtgagt gtgccacaac tacctaacac
5161 atcagcaaat ctgattaac cactttcttt
     gattttccac aatgcaacct tactttttaa
5221 tagttgggaa tgttctaagt gaatttagca
     gaggttgtta atcaacttga aagctgaatt
5281 ctgacttgtc tgactcttgg tggtgctggt
     agcagtagat gtttactttt aggttttggt
5341 ggtggtggaa tatcacttca acgtaaatca
     tcagaaataa gtatttgtga acccctctcg
5401 cattaatgta tcttattctg taaaaagaac
     atgtgcaatt tctcttagat acactactgc
5461 tgcagctcac aaacacctct gcatattaca
     tgtacctcct cctgctcctc aagagtgtgg
5521 tctattttgc catcatcacc tgctgtctgc
     ttagaagaac ggctttctgc tgcaatggag
5581 agaaatcata a
```

[SEQ ID NO: 33]

```
  1 ataaacaact tgatgcagat gtttcccca
    agcccactat ttttcttcct tcgattgctg
 61 aaacaaaact ccagaaggct ggaacatacc
    tttgtcttct tgagaaattt ttcccagata
121 ttattaagat acattggcaa gaaaagaaga
    gcaacacgat tctgggatcc caggaggga
181 acaccatgaa gactaacgac acatacatga
    aatttagctg gttaacggtg ccagaagagt
241 cactggacaa agaacacaga tgtatcgtca
    gacatgagaa taataaaaac ggaattgatc
301 aagaaattat ctttcctcca ataaagacag
    gtatgtgttt acacatatca tctgtcagaa
```

```
 361 cacttctttg aaagtgaatg ctgcattttt
     tcctttcagt attaatgaaa aacataaatc
 421 tttcttaaaa attgttacat ttaatggtag
     cgtaaatgcc ctgctacttt tctatagaat
 481 taaaatggta taggttttgg agaaaacaaa
     attgaaaaag ttgctgaagg tttgtcagcc
 541 tcagctccat tatccaaaat aagaaagtca
     cgtgctggtt tttagggttg ttagatggat
 601 taaagaaaca acatacacag aagcatctag
     caacgtgaca cgtggtaaac gctcaaaaag
 661 tgttctccct tcttttgatg actttacttg
     atcaggaaat aacatatata tgtctttcag
 721 gaatgttctg cccaagcagg agagtcactc
     acctcaatct tgctacccac aaagtttaac
 781 ctaaaaacaa cgggttcatt gttgacaaaa
     taatgtttat ctgaagataa ctgtagatca
 841 tatttatctg tagataatgt ttatctgtgg
     agtgtggctc tacaaaacat agaatagtct
 901 tggtcactgc agttttatag aggccttggg
     tttttcagag tttcatttta tatatcacca
 961 taaagtaaca tttcataatt acaggttggt
     aaggcttaca tgtacaaaca ttcttccatt
1021 ttccataata aatgcatttc ctgccattgg
     tgaatgcagc tcaataaaca tttattgtac
1081 aattatgaca cgccaggctt agtggaaatg
     tggatgaaca gacaaggatg agttactgtc
1141 ctaaggatga tgcatgacag tgcagagaat
     atactctctt cctgatcact cagggtcact
1201 catgattcat gcgcgaggtc ccaaaacagt
     gcctttgatg cagattctgt acatctctag
1261 acgattggtc caagggctga atgtgctctg
     gcccagtggt ccagtctgtc actatatgtc
1321 aacatcctga atatgaacat aacagtccaa
     catctcaaga gtgggcatga aaaggactca
1381 ttttgtgctt ttcctgtgg ttaacaagtc
     ctttttagcc tgggggaaca agcattaaca
1441 aaatgtttga agatctttgc cacgtaccat
     tccaaatttc tagggtaagt ctttagcttt
1501 tcagatcctg agtttctgca atgatcaaat
     gtgatttgga cagttgcgtt gactttctcc
1561 tggggctata atggagtgca aaggaaacaa
     tggcagggaa aatgcttgct ttcaaaatgg
1621 tagcatggat gtgttcattc gtgtagttac
     tgtattaggt atagcctttc ctgaaactaa
1681 ctgaagtggg gttataaaaa cagtcccaat
     tttctatttc ctttgctgag acacaaagag
1741 gagacaaaag agcaaagctt gagggtagtt
     ttaccactgt gcttaagtgt tctgatttt
1801 ccagtgatca gggtgaaata aaaagcatag
     taagttccag ggcagtgaat accatacagg
1861 agacaagtta cagttttata atgtgtttta
     ctttacacta aattctaaaa gtaaaatgtc
1921 tttttttttt tccgagacag agtttcactc
     ttgtagccca ggcaggagtg ctatggtgtg
1981 atctcggctc acagcaacct ccacctccca
     gtttcaagcg attcttctgc ctcagcctcc
2041 cgagaagttg aaattacagg tgcctggcac
     catatctcgc taattattct attttttagta
2101 gagatcgggt tttaccatgt tggccaggct
     ggtctcgaac tcctgacttc aagtgatcca
2161 cccgcctcag cctcccaaag tgctgggatt
     acaggtgtga gtcactgtgc cggacctaac
2221 agtaaaatgt cttcatgtg cttctcaagg
     caactacatt aaggaggaca catctcttaa
2281 tgtcattcta cagtagattt ctaatgctct
     ttcttggaag tttgtttttc tgagaagagc
2341 taaaaatata ataacatgga agtgatcata
     ttatataatc aatgaagtgc tttcaaagga
2401 gataaaacta acctggtctg catttgcaac
     cagccttgat tgagagagag agaactcagg
2461 atacacttag agattttatt atggggaata
     gttactttat tcattttacc tcaatcaatg
2521 catggaaata agtgacagtc attttcattt
     atcttttaat aaataaagtc accatgagga
2581 aaatgaaaac ccattaaagt cagtccttaa
     agatatttgg acatgcagac atgataacta
2641 acatttccat tcgtgagact tacccaaaac
     ctatacctca agtccatttc ttagaataca
2701 tgaaataaag atctcagtga gtgtataaaa
     ctgcacacca gaatcatatc cgtatagaca
```

-continued

```
2761 agaatacatc tactagaaaa atataaacca
     aaacaccaag gtgactctgt ttttttctgt
2821 tttaaaatat gttgtctttg tatgcatgtt
     tgcttcttcc tttttttttt taaacatcgc
2881 agataaattc aactctcacc tcagttgaga
     gagaactgtc aatgtgactt ggcctctctc
2941 tttctagtcc cagaaagaat tgcactgaaa
     tgctgagctc ctgtaataaa aatgaccatt
3001 tgctgagagt aattaacata ctgaaagaga
     ttttcttaga atagtgcaca atggcccaat
3061 ggtgacatta tattgtctct ttataaatta
     ttttctatct atttctgtgg attatttcta
3121 caaagcactt ttcatatgtc caattccttt
     tattccccta caagtactga ctgactactg
3181 gctctgctgt tcactgatat gactttcggc
     aagttgcctg cactttttaa acgttatttc
3241 ctcattcaga acatggggcc atacaaaata
     caactcactt cagtgttatt ggggaattaa
3301 acaaataaat gcatgggaag catttaacat
     agtgcctgac acaataatga gcactcagta
3361 gatgttagct tttattaata ttgttgttgc
     tatgtccaga aacactatac ctccagaaaa
3421 tcatgggtac ttgctgggga cgttgggat
     atgcatgatt ttgaaaggag tgactgctct
3481 ttactgctca gatgagaaat ttttctaagc
     cagactcctc caaacatgta agattctgtt
3541 gtggattcta ggactgaaag aattcttggc
     cgagtgtggt ggcttatcct ggtaatctca
3601 tcatttggga ggacaaggca ggaagattgc
     ttgagcccag gagttggaaa caagcctgga
3661 caacatgcg aaaccctgtc tctacaaaaa
     atacaaacat tagctggtca tgggagtgag
3721 tgcctgtact cccagctact caggaggcta
     agataggagg atcacctgag cctgggcagt
3781 ttgaggtttc agtgagccgt gatgacacca
     tactatactc cactccagcc tgggtgacag
3841 tgacatcctg cctcaaaaaa accccaaaa
     ttattctttt tgctgatttc atgtcagcag
3901 tgtgtgctga aggctgtaaa gtagccactt
     gttctgttta ttttttccatt gaacaagtat
```

-continued

```
3961 ttatcaaaaa cgtactttgt ggaaggcact
     gtgctaggaa ctatgcatac agaaggaaaa
4021 ccaaatgttc ttggatacta cactccagtt
     gtgataaaaa agaaaaaagt attcttcaca
4081 aacttcaaca ttttgatgtg caaaaacata
     atatatgaat tagatctacc taactacaca
4141 gaattagacc aattatttct gggattatgg
     gctcatattt ttaataactg tcctcctacc
4201 tctctgttga caggttttat aaatattcat
     ttaattacac acagtcacag acacactcag
4261 acacacacac atacacacac acacacacct
     tgacaaataa tgggcatgaa caattgactg
4321 gtacttgctc tcattcttct agatgtcacc
     acagtggatc ccaaatacaa ttattcaaag
4381 gatgcaaatg gtaagttttt gtgttttta
     tttcctcctg atcattttaa gttttgaact
4441 tctctggctt gaaaaatcag ggaatggatt
     ttgctaggtt ggatgctgca gaatggacct
4501 aatcatattt taaattagtc cctctttttc
     taggagttgt attaacaaac ctaactactg
4561 cttcatgtaa gagatgactg taaattgaag
     ggtacagtga tatgctttca gttatttcaa
4621 aaaacagact ttactcatcc atgtgtcttt
     tttcttttct tttttttctt ttttgagacg
4681 gagtctcgct ctgttgaaca ggctggattg
     cagtgacgcg atctcacctc actacaacct
4741 ccgcctctgg agttcaagcg attctccagc
     ctcagcttct caagtagctg ggactacagg
4801 cacatgccac catgtccggg tcatctttgt
     attttagca gagaccgggt ttcactatgt
4861 tggccaggct ggtctagaat tcctgacttc
     gtgatctgcc ccctcagccc tccgaagtgc
4921 tgggattaca gacgtgagtc actgtgcccg
     gcctaacagt aaaatgtctt tcatgcgctt
4981 ctcaaggcaa ctacgttaag gaggacactt
     ctcttaatgt cattctacag tagatttcta
5041 atgctctttc ttggaagttt gttttttctga
     gaaaagctaa aaatataaca tggaagtgat
5101 catattgtat aatcaatgaa gtgcttttca
     aggagataaa actaatctgg tccacgtttg
```

-continued

```
5161 caaccaacct tgattgagag agagagagaa
     ctcaggatac acttggagat tttattatgg
5221 ggaatagtta ctttattctt ttttcctcaa
     tcaattcatg gaaataagtg atagtcatat
5281 tcatttatct tttaataaat gaagtcacca
     tgaggaaaat aaaaagacat tgaaaaccca
5341 ttaaagttag cccttaaaga tatttggaca
     tgcagacttg ataactaacg tttgcattct
5401 tgagacttac ccaaaaccca tacctcaagt
     ccatgttttt agaattcatg aaataaagat
5461 ctcagtgagt gcataaaatt gcgcaccaga
     atcatatccg tatagacaag aacacatcta
5521 ctagaaaaat aataaaccaa cacaccaatg
     caactgtgtt ttcttctgtt ttaaaatatg
5581 ttgtctttgt atgcatgttt gcttcttcct
     tttttttttt taacatcaca gataaattca
5641 actctcacct caggttttat tgagagaact
     gtcaatgtga cttggcctct gtctttctag
5701 tcccagaaag aatcgcactg aaatgctgag
     ctcctgtaat aaaaatgacc atttgctgag
5761 agtaattaac atactgaaag agattttctt
     agagtacaca atggtgacat tatattgtct
5821 ctttataaat aactttctat ctatttctgt
     ggattattcc tacaaagtac ttttcatatg
5881 tccagtttct tttcttcccc tacaactacc
     gtctgaatac tggctctgct atttgctgat
5941 atgattctcg gcaagttgcc tgcactttt
     aaactttatt tcctcattca gaacatgggg
6001 ccatgtaata ctcatgtacg tgagtattac
     gtaataatgc tcacttaagt gttactgggg
6061 aattaaacaa aaaaatgcat ggcaagcatt
     taacatagtg cctgacacaa taatgagcac
6121 tcagtagatg ttagatttta ttaatattgt
     tgttgttatg tccggaaaca ctatacctcc
6181 agaaaatcat gggtacttgc ttgggatgtt
     ggggatatgc atgatttgga aaggtatgac
6241 tgcttttttc tgcttagatg agaaattttt
     ctaagccaga ctccttcaaa tatgtaagat
6301 tctgttgtgg attctaggac ggaaagaatt
     cttggtcagg tgtggtttct tatccctgta
6361 atcccagaat tttgggagga caaggcagga
     agattgcttg agcccaggag tttgaaacca
6421 gcctgggcaa caagacgaaa ccctgtctct
     acaaaagtac ataaattagc ttggcttggt
6481 ggtgtgtgcc tgtattacca gctattcggg
     agactgagat gggaggatct cctgaacctg
6541 tgaagtttga ggcttcagtg agccgtgatg
     acaccatact atactcgact ccagcctgtg
6601 cgacagtgag actctgcgtc aaaaaaaaaa
     ccccaaaatt attgtttttg ctgatttcag
6661 gtcagcagtg tgtgctgaag ggtgtaaagt
     agccacttga tcagtttatt tttccactga
6721 acaagtattt atcaaaaaca tactttgtgg
     tctgtttttg ataaataaaa aggcactgtg
6781 ctaggagcca tgaatacaga aggaaaacca
     aatgttcttg gatactacac tccagttgtg
6841 ataaaaaaga aaaatgtatt cttcacgaac
     ttcaacattt tgatatgcaa aaacatagta
6901 tataaattag atctacctga ttacgtagaa
     tcagaccaat tatttctgga attgagggct
6961 catatttta ataactgtcc tcctgcctct
     ctgttgacag gttttataaa tattcattta
7021 attacacaca cacacacaca caccttgaca
     ataatggac atgaacaatt gactagtact
7081 tgctctcatt cttctagatg tcatcacaat
     ggatcccaaa gacaattggt caaaagatgc
7141 aaatggtaag cttttgtgtt tttcctttcc
     tcctgatcat tttaagtttt gaacttctct
7201 ggcttgaaaa atcagggaat gggccgggtg
     cggtggctca cgcctgtaat cccagcactt
7261 tgggaggcca aggcgggcgg atcacgaggt
     caggagatcg agaccatccc ggctaaaacg
7321 gtgaaacccc gtctctacta aaaatacaaa
     aaattagccg ggcttagtgg cgggcgcctg
7381 tagtcccagc tacttgggag gctgaggcag
     gagaatggcg tgaacccggg aggcggagct
7441 tgcagtgagc cgagattgcg ccactgcact
     ccactccagc ctgggcgaca gagcgagact
7501 ccgtctcaaa aaaaaaaaaa aaaaaaaaa
     aagaaaaatc agggaatgga ttttgctagg
```

-continued

```
7561 ttggatgctg cagaatggac ctagtgatat
     tttaaattag tccctctttt tctaggagtt
7621 gtattaacaa acctaactac tgcttcgggt
     atgagatgac tgtaaattag agggtacagt
7681 gatatgcttt cagttatttc aaaaaacaga
     ctttattcat ccgtctgtct tttttttttt
7741 tttttttttt ttttttttgag acggaggagt
     ctcactctat cacccaggct ggagtgcagt
7801 ggcgcgatct cggctcacca taacctccgc
     cttactggtt caagcgattc tccagcctca
7861 gcttctcaag tagctgggac tacaggtgca
     caccaccata cctggctaat ttttgtattt
7921 ttaatagaga tggggtttca ccacgctggc
     caggatggtc ttgaattctt gacctcgtga
7981 tctgccccct cgggctccca aacttctggg
     attataggcg tgagccactg tgcccggcct
8041 tctgtctttt gttataatga ctggggaaaa
     catgatacca tgttgcttct tgagttgttt
8101 tgttttagtc tttggtcttt gctagtagct
     aataacacga actagtgttt atcaagtgct
8161 ttttacacag aagggcttgt tctgcatttt
     ctagtttaat catcttaata ctcctataaa
8221 gtagtacaat atatttctc ccattttaca
     gtccctttaa agtaaataac tataaaaatc
8281 ccttatacat gtcacacagc taggtctggc
     atttcaaatc aggacatcaa acaaagaatt
8341 cgtgcagtta ctaagtcctc tatttttttct
     acaatagaaa aaatagcaag aattacagat
8401 agcaagacat tacaaggcag gaatctgaaa
     cgaaagggac ataatgtggg gctgggtggg
8461 tgcatgagct ttgcagacta gactttcatt
     ccagctcttt taatgattag gtgtaagtga
8521 cctacatttt gtgagtaaca gttttctcat
     cagccaacta agaataatta caccagattc
8581 acagttattg aagagataag ggcatgaatg
     tgagatgtct ggcgtagggt atctcattta
8641 gcagacacag aatgaatact tgtttctggc
     ttttctctc tacatatgca caaagaatgt
8701 gactagaagc attggctcta gccctgctca
     actttcctct atttccaata ccaggggct
8761 ctgacttagg ctgccacacc aggcaaggag
     gggcagtacc acctcacttg accaagggca
8821 gggagtcacg gacacatcac ttcctgagat
     ccttttccac accaaggact gatgtttctg
8881 gaattctcac tttatgaaga caaaacatat
     aaatggaaat ttctgcagga agagactcac
8941 tcttgtagct cattgagtag gcactagtgg
     tccacccca ctgtctttac ttattccttg
9001 acatcacata tctcttgtaa aacctcaaat
     aatgttaaat gcaatcaccc aataatagca
9061 tagccataat tagaggcatt taggaaagac
     aggtgagtgt gccacaacta cctaacacat
9121 cagcaaatct ggattaacca ctttctttga
     ttttccacaa tgcaaccta cttttaata
9181 gttgggaatg ttctaagtga atttagcaga
     ggttgttaat caacttgaaa gctgaattct
9241 gacttgtctg actcttggtg gtgctggtag
     cagtagatgt ttacttttag gttttggtgg
9301 tggtggaata tcacttcaac gtaaatcatc
     agaaataagt atttgtgaac ccctctcgca
9361 ttaatatatc ttattctgta aaaagaacat
     gtgcaatttc tcttagatac actactgctg
9421 cagctcacaa acacctctgc atattacacg
     tacctcctcc tgctcctcaa gagtgtggtc
9481 tattttgcca tcatcacctg ctgtctgctt
     agaagaacgg ctttctgctg caatggagag
9541 aaatcataa
```

In accordance with the presently disclosed subject matter, an "TRGC nucleic acid molecule" refers to a polynucleotide encoding an TRGC polypeptide.

In certain embodiments, the constant domain of a presently disclosed HI-TCR comprises a native or modified TRDC peptide. In certain embodiments, the TRDC polypeptide has an amino acid sequence that is at least about 85%, about 90%, about 95%, about 96%, about 97%, about 98%, about 99% or 100% homologous or identical to the amino acid sequence set forth in SEQ ID NO: 41, which is provided below.

[SEQ ID NO: 41]
SQPHTKPSVF VMKNGTNVAC LVKEFYPKDI RINLVSSKKI

TEFDPAIVIS PSGKYNAVKL GKYEDSNSVT CSVQHDNKTV

HSTDFEVKTD STDHVKPKET ENTKQPSKSC HKPKAIVHTE

KVNMMSLTVL GLRMLFAKTV AVNFLLTAKL FFL

In certain non-limiting embodiments, T cell receptor constant region comprises a hinge/spacer region that links the extracellular antigen-binding domain to the constant domain. The hinge/spacer region can be flexible enough to allow the antigen binding domain to orient in different directions to facilitate antigen recognition. In certain non-limiting embodiments, the hinge/spacer region can be the hinge region from IgG1, or the $CH_2CH_3$ region of immunoglobulin and portions of CD3, a portion of a CD28 polypeptide, a portion of a CD8 polypeptide, a variation of any of the foregoing which is at least about 80%, at least about 85%, at least about 90%, or at least about 95% homologous or identical thereto, or a synthetic spacer sequence. In certain non-limiting embodiments, the hinge/spacer region of the CAR can comprise a native or modified hinge region of a CD3ζ polypeptide, a CD40 polypeptide, a 4-1BB polypeptide, an OX40 polypeptide, a CD166 peptide, a CD166 peptide, a CD8a peptide, a CD8b peptide, an ICOS polypeptide, an ICAM-1 peptide, a CTLA-4 peptide, a synthetic peptide (not based on a protein associated with the immune response), or a combination thereof.

2.4. Intracellular Signaling Domain

In certain non-limiting embodiments, a presently disclosed HI-TCR comprises an antigen binding chain, which does not comprise an intracellular domain. In certain embodiments, the antigen binding chain is capable of associating with a CD3ζ polypeptide. In certain embodiments, the antigen binding chain comprises a constant domain, which is capable of associating with a CD3ζ polypeptide. In certain embodiments, the CD3ζ polypeptide is endogenous. In certain embodiments, the CD3ζ polypeptide is exogenous. In certain embodiments, binding of the antigen binding chain to an antigen is capable of activating the CD3ζ polypeptide associated to the antigen binding chain. In certain embodiments, the exogenous CD3ζ polypeptide is fused to or integrated with a costimulatory molecule disclosed herein.

In certain non-limiting embodiments, a presently disclosed HI-TCR comprises an antigen binding chain that comprises an intracellular domain. In certain embodiments, the intracellular domain comprises a CD3ζ polypeptide. In certain embodiments, binding of the antigen binding chain to an antigen is capable of activating the CD3ζ polypeptide of the antigen binding chain.

The activated CD3ζ polypeptide can activate and/or stimulate an immunoresponsive cell (e.g., a cell of the lymphoid lineage, e.g., a T cell). CD3ζ comprises three immunoreceptor tyrosine-based activation motifs (ITAM1, ITAM2 and ITAM3), three basic-rich stretch (BRS) regions (BRS1, BRS2 and BRS3), and transmits an activation signal to the cell (e.g., a cell of the lymphoid lineage, e.g., a T cell) after antigen is bound to the antigen binding chain. The intracellular signaling domain of the CD3ζ-chain is the primary transmitter of signals from endogenous TCRs. In certain embodiments, the CD3ζ polypeptide comprises or has an amino acid sequence that is at least about 85%, about 90%, about 95%, about 96%, about 97%, about 98%, about 99% or about 100% homologous to the sequence having a NCBI Reference No: NP_932170 (SEQ ID NO: 17), NCBI Reference No: NP_000725.1 (SEQ ID NO: 18) or fragments thereof, and/or may optionally comprise up to one or up to two or up to three conservative amino acid substitutions. In certain non-limiting embodiments, the CD3ζ polypeptide comprises or has an amino acid sequence that is a consecutive portion of SEQ ID NO: 17, which is at least 20, or at least 30, or at least 40, or at least 50, and up to 164 amino acids in length. Alternatively or additionally, in non-limiting various embodiments, the CD3ζ polypeptide comprises or has an amino acid sequence of amino acids 1 to 164, 1 to 50, 50 to 100, 100 to 150, or 150 to 164 of SEQ ID NO: 17. In certain embodiments, the CD3ζ polypeptide comprises or has an amino acid sequence of amino acids 52 to 164 of SEQ ID NO: 17.

SEQ ID NO: 17 is provided below:

```
                                                [SEQ ID NO: 17]
   1  MKWKALFTAA ILQAQLPITE AQSFGLLDPK LCYLLDGILF

IYGVILTALF LRVKFSRSAD

61  APAYQQGQNQ LYNELNLGRR EEYDVLDKRR GRDPEMGGKP

QRRKNPQEGL YNELQKDKMA

121  EAYSEIGMKG ERRRGKGHDG LYQGLSTATK DTYDALHMQA

LPPR
```

In certain embodiments, the intracellular signaling domain comprises a human CD3ζ polypeptide. The human CD3ζ polypeptide can comprise or have an amino acid sequence that is at least about 85%, about 90%, about 95%, about 96%, about 97%, about 98%, about 99% or about 100% homologous or identical to SEQ ID NO: 18 or fragments thereof, and/or may optionally comprise up to one or up to two or up to three conservative amino acid substitutions. SEQ ID NO: 18 is provided below:

```
                                                [SEQ ID NO: 18]
   RVKFSRSADA PAYQQGQNQL YNELNLGRRE EYDVLDKRRG

RDPEMGGKPR RKNPQEGLYN ELQKDKMAEA YSEIGMKGER

RRGKGHDGLY QGLSTATKDT YDALHMQALP PR.
```

An exemplary nucleic acid sequence encoding the amino acid sequence of SEQ ID NO: 18 is set forth in SEQ ID NO: 19, which is provided below.

```
                                                [SEQ ID NO: 19]
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC
```

2.4.1. Co-Stimulatory Region

In certain non-limiting embodiments, a presently disclosed HI-TCR comprises an antigen binding chain that comprises an intracellular domain, wherein the intracellular domain comprises a co-stimulatory region. In certain embodiments, the intracellular domain comprises a co-stimulatory region and a CD3ζ polypeptide. In certain embodiments, the intracellular domain comprises a co-stimulatory region and does not comprise a CD3ζ polypeptide.

In certain embodiments, the co-stimulatory region comprises at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a DAP-10 polypeptide, or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, and 4-1BBL. As one example, a 4-1BB ligand (i.e., 4-1BBL) may bind to 4-1BB (also known as "CD137") for providing an intracellular signal that in combination with a CAR signal induces an effector cell function of the CAR$^+$ T cell. CARs comprising an intracellular signaling domain that comprises a co-stimulatory signaling region comprising 4-1BB, ICOS or DAP-10 are disclosed in U.S. Pat. No. 7,446,190, which is herein incorporated by reference in its entirety.

In certain embodiments, the co-stimulatory region of an antigen binding chain of a HI-TCR comprises a co-stimulatory signaling region that comprises a CD28 polypeptide. The CD28 polypeptide can comprise or have an amino acid sequence that is at least about 85%, about 90%, about 95%, about 96%, about 97%, about 98%, about 99% or 100% homologous or identical to the sequence having a NCBI Reference No: P10747 or NP_006130 (SEQ ID NO: 20), or fragments thereof, and/or may optionally comprise up to one or up to two or up to three conservative amino acid substitutions. In non-limiting certain embodiments, the CD28 polypeptide comprises or has an amino acid sequence that is a consecutive portion of SEQ ID NO: 20 which is at least 20, or at least 30, or at least 40, or at least 50, and up to 220 amino acids in length. Alternatively or additionally, in non-limiting various embodiments, the CD28 polypeptide comprises or has an amino acid sequence of amino acids 1 to 220, 1 to 50, 50 to 100, 100 to 150, 114 to 220, 150 to 200, or 200 to 220 of SEQ ID NO: 20. In certain embodiments, the co-stimulatory region comprises a co-stimulatory signaling region that comprises a CD28 polypeptide comprising or having an amino acid sequence of amino acids 180 to 220 of SEQ ID NO: 20.

```
                                              [SEQ ID NO: 20]
  1  MLRLLLALNL  FPSIQVTGNK  ILVKQSPMLV  AYDNAVNLSC

KYSYNLFSRE  FRASLHKGLD

61  SAVEVCVVYG  NYSQQLQVYS  KTGFNCDGKL  GNESVTFYLQ

NLYVNQTDIY  FCKIEVMYPP

121  PYLDNEKSNG  TIIHVKGKHL  CPSPLFPGPS  KPFWVLVVVG

GVLACYSLLV  TVAFIIFWVR

181  SKRSRLLHSD  YMNMTPRRPG  PTRKHYQPYA  PPRDFAAYRS
```

In certain embodiments, the co-stimulatory region comprises a human intracellular signaling domain of CD28. The human intracellular signaling domain of CD28 can comprise or have an amino acid sequence that is at least about 85%, about 90%, about 95%, about 96%, about 97%, about 98%, about 99% or about 100% homologous or identical to SEQ ID NO: 21 or fragments thereof, and/or may optionally comprise up to one or up to two or up to three conservative amino acid substitutions. SEQ ID NO: 21 is provided below:

```
                                              [SEQ ID NO: 21]
     RSKRSRLLHS  DYMNMTPRRP  GPTRKHYQPY  APPRDFAAYR  S.
```

An exemplary nucleic acid sequence encoding the amino acid sequence of SEQ ID NO: 21 is set forth in SEQ ID NO: 22, which is provided below.

```
                                              [SEQ ID NO: 22]
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC
```

In certain embodiments, the co-stimulatory region comprises a co-stimulatory signaling region that comprises two co-stimulatory molecules, e.g., co-stimulatory signaling regions of CD28 and 4-1BB or co-stimulatory signaling regions of CD28 and OX40.

4-1BB can act as a tumor necrosis factor (TNF) ligand and have stimulatory activity. The 4-1BB polypeptide can comprise or have an amino acid sequence that is at least about 85%, about 90%, about 95%, about 96%, about 97%, about 98%, about 99% or about 100% homologous or identical to the sequence having a NCBI Reference No: P41273 or NP_001552 (SEQ ID NO: 23) or fragments thereof, and/or may optionally comprise up to one or up to two or up to three conservative amino acid substitutions.

SEQ ID NO: 23 is provided below:

```
                                              [SEQ ID NO: 23]
  1  MGNSCYNIVA  TLLLVLNFER  TRSLQDPCSN  CPAGTFCDNN

RNQICSPCPP  NSFSSAGGQR

61  TCDICRQCKG  VFRTRKECSS  TSNAECDCTP  GFHCLGAGCS

MCEQDCKQGQ  ELTKKGCKDC

121  CFGTFNDQKR  GICRPWTNCS  LDGKSVLVNG  TKERDVVCGP

SPADLSPGAS  SVTPPAPARE

181  PGHSPQIISF  FLALTSTALL  FLLFFLTLRF  SVVKRGRKKL

LYIFKQPFMR  PVQTTQEEDG

241  CSCRFPEEEE  GGCEL
```

In accordance with the presently disclosed subject matter, a "4-1BB nucleic acid molecule" refers to a polynucleotide encoding a 4-1BB polypeptide.

In certain embodiments, the co-stimulatory region comprises an intracellular signaling domain of 4-1BB. The intracellular signaling domain of 4-1BB can comprise or have an amino acid sequence that is at least about 85%, about 90%, about 95%, about 96%, about 97%, about 98%, about 99% or about 100% homologous or identical to SEQ ID NO: 24 or fragments thereof, and/or may optionally comprise up to one or up to two or up to three conservative amino acid substitutions. SEQ ID NO: 24 is provided below:

```
                                              [SEQ ID NO: 24]
     KRGRKKLLYI  FKQPFMRPVQ  TTQEEDGCSC  RFPEEEEGGC  EL.
```

An exemplary nucleic acid sequence encoding the amino acid sequence of SEQ ID NO: 24 is set forth in SEQ ID NO: 27, which is provided below.

[SEQ ID NO: 27]
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

An OX40 polypeptide can comprise or have an amino acid sequence that is at least about 85%, about 90%, about 95%, about 96%, about 97%, about 98%, about 99% or about 100% homologous or identical to the sequence having a NCBI Reference No: P43489 or NP_003318 (SEQ ID NO: 25), or fragments thereof, and/or may optionally comprise up to one or up to two or up to three conservative amino acid substitutions.

SEQ ID NO: 25 is provided below:

```
                                                [SEQ ID NO: 25]
  1  MCVGARRLGR  GPCAALLLLG  LGLSTVTGLH  CVGDTYPSND
     RCCHECRPGN  GMVSRCSRSQ
 61  NTVCRPCGPG  FYNDVVSSKP  CKPCTWCNLR  SGSERKQLCT
     ATQDTVCRCR  AGTQPLDSYK
121  PGVDCAPCPP  GHFSPGDNQA  CKPWTNCTLA  GKHTLQPASN
     SSDAICEDRD  PPATQPQETQ
181  GPPARPITVQ  PTEAWPRTSQ  GPSTRPVEVP  GGRAVAAILG
     LGLVLGLLGP  LAILLALYLL
241  RRDQRLPPDA  HKPPGGGSFR  TPIQEEQADA  HSTLAKI
```

In accordance with the presently disclosed subject matter, an "OX40 nucleic acid molecule" refers to a polynucleotide encoding an OX40 polypeptide.

An ICOS polypeptide can comprise or have an amino acid sequence that is at least about 85%, about 90%, about 95%, about 96%, about 97%, about 98%, about 99% or about 100% homologous or identical to the sequence having a NCBI Reference No: NP_036224 (SEQ ID NO: 26) or fragments thereof, and/or may optionally comprise up to one or up to two or up to three conservative amino acid substitutions.

SEQ ID NO: 26 is provided below:

```
                                                [SEQ ID NO: 26]
  1  MKSGLWYFFL  FCLRIKVLTG  EINGSANYEM  FIFHNGGVQI
     LCKYPDIVQQ  FKMQLLKGGQ
 61  ILCDLIKTKG  SGNTVSIKSL  KFCHSQLSNN  SVSFFLYNLD
     HSHANYYFCN  LSIFDPPPFK
121  VTLIGGYLHI  YESQLCCQLK  FWLPIGCAAF  VVVCILGCIL
     ICWLTKKKYS  SSVHDPNGEY
181  MFMRAVNTAK  KSRLTDVTL
```

In accordance with the presently disclosed subject matter, an "ICOS nucleic acid molecule" refers to a polynucleotide encoding an ICOS polypeptide.

In certain embodiments, mutation sites and/or junction between domains/motifs/regions of the CAR derived from different proteins are de-immunized. Immunogenicity of junctions between different CAR moieties can be predicted using NetMHC 4.0 Server. For each peptide containing at least 1 aa from next moiety, binding affinity to HLA A, B and C, for all alleles, can be predicted. A score of immunogenicity of each peptide can be assigned for each peptide. Immunogenicity score can be calculated using the formula Immunogenicity score=$[(50-\text{binding affinity})*\text{HLA frequency}]_n$. n is the number of prediction for each peptide.

2.5. CD3 Complex

In certain embodiments, a presently disclosed HI-TCR is capable of associating with a CD3 complex (also known as "T-cell co-receptor"). In certain embodiments, the HI-TCR and the CD3 complex form an antigen recognizing receptor complex similar to a native TCR/CD3 complex. In certain embodiments, the CD3 complex is endogenous. In certain embodiments, the CD3 complex is exogenous. In certain embodiments, the presently disclosed HI-TCR replaces a native and/or an endogenous TCR in the CD3/TCR complex. In certain embodiments, the CD3 complex comprises a CD3γ chain, a CD3δ chain, and two CD3ε chains.

In certain embodiments, the CD3γ chain comprises or has an amino acid sequence that is at least about 85%, about 90%, about 95%, about 96%, about 97%, about 98%, about 99% or about 100% homologous or identical to NCBI reference number: NP_000064.1 (SEQ ID NO: 34, which is provided below) or fragments thereof, and/or may optionally comprise up to one or up to two or up to three conservative amino acid substitutions.

```
                                                [SEQ ID NO: 34]
  1  meqgkglavl  ilaiillqgt  laqsikgnhl  vkvydyqedg
     svlltcdaea  knitwfkdgk
 61  migfltedkk  kwnlgsnakd  prgmyqckgs  qnkskplqvy
     yrmcqnciel  naatisgflf
121  aeivsifvla  vgvyfiagqd  gvrqsrasdk  qtllpndqly
     qplkdreddq  yshlqgnqlr
181  rn
```

In certain embodiments, the CD3δ chain comprises or has an amino acid sequence that is at least about 85%, about 90%, about 95%, about 96%, about 97%, about 98%, about 99% or about 100% homologous or identical to NCBI reference numbers: NP_000723.1 (SEQ ID NO: 35, which is provided below), NP_001035741.1 (SEQ ID NO: 36, which is provided below) or fragments thereof, and/or may optionally comprise up to one or up to two or up to three conservative amino acid substitutions.

```
                                                [SEQ ID NO: 35]
  1  mehstflsgl  vlatllsqvs  pfkipieele  drvfvncnts
     itwvegtvgt  llsditrldl
 61  gkrildprgi  yrcngtdiyk  dkestvqvhy  rmcgscveld
     patvagiivt  dviatlllal
121  gvfcfaghet  grlsgaadtq  allrndqvyq  plrdrddaqy
     shlggnwarn  k
```

```
                                                [SEQ ID NO: 36]
  1  mehstflsgl  vlatllsqvs  pfkipieele  drvfvncnts
     itwvegtvgt  llsditrldl
```

```
 61  gkrildprgi yrcngtdiyk dkestvqvhy rtadtqallr ndqvyqplrd rddagyshlg 121  gnwarnk
```

In certain embodiments, the CD3ε chain comprises or has an amino acid sequence that is at least about 85%, about 90%, about 95%, about 96%, about 97%, about 98%, about 99% or about 100% homologous or identical to NCBI reference number: NP_000724.1 (SEQ ID NO: 37, which is provided below) or fragments thereof, and/or may optionally comprise up to one or up to two or up to three conservative amino acid substitutions.

```
                                              [SEQ ID NO: 37]
  1  mqsgthwrvl glcllsvgvw gqdgneemgg itqtpykvsi sgttviltcp qypgseilwq 61  hndkniggde ddknigsded hlslkefsel eqsgyyvcyp rgskpedanf ylylrarvce 121  ncmemdvmsv ativivdici tgglllvyy wsknrkakak pvtrgagagg rqrgqnkerp 181  ppvpnpdyep irkgqrdlys glnqrri
```

In certain embodiments, the recombinant TCR exhibits a greater antigen sensitivity than a CAR targeting the same antigen. In certain embodiments, the recombinant TCR is capable of inducing an immune response when binding to an antigen that has a low density on the surface of a tumor cell. In certain embodiments, immunoresponsive cells comprising a presently disclosed HI-TCR can be used to treat a subject having tumor cells with a low expression level of a surface antigen, e.g., from a relapse of a disease, wherein the subject received treatment which leads to residual tumor cells. In certain embodiments, the tumor cells have a low density of a target molecule on the surface of the tumor cells. In certain embodiments, a target molecule having a low density on the cell surface has a density of less than about 5,000 molecules per cell, less than about 4,000 molecules per cell, less than about 3,000 molecules per cell, less than about 2,000 molecules per cell, less than about 1,500 molecules per cell, less than about 1,000 molecules per cell, less than about 500 molecules per cell, less than about 200 molecules per cell, or less than about 100 molecules per cell. In certain embodiments, a target molecule having a low density on the cell surface has a density of less than about 2,000 molecules per cell. In certain embodiments, a target molecule having a low density on the cell surface has a density of less than about 1,500 molecules per cell. In certain embodiments, a target molecule having a low density on the cell surface has a density of less than about 1,000 molecules per cell. In certain embodiments, a target molecule having a low density on the cell surface has a density of between about 4,000 molecules per cell and about 2,000 molecules per cell, between about 2,000 molecules per cell and about 1,000 molecules per cell, between about 1,500 molecules per cell and about 1,000 molecules per cell, between about 2,000 molecules per cell and about 500 molecules per cell, between about 1,000 molecules per cell and about 200 molecules per cell, or between about 1,000 molecules per cell and about 100 molecules per cell.

2.6. HI-TCR 19

In certain embodiments, a presently disclosed HI-TCR comprises two antigen binding chains, e.g., VL-TRAC and VH-TRBC, which are capable of dimerizing, wherein the HI-TCR binds to CD19 (e.g., human CD19).

VL-TRAC

In certain embodiments, a presently disclosed HI-TCR comprises an antigen binding chain that comprises an extracellular antigen-binding domain of a $V_L$ domain of an antibody and a constant domain of TRAC. In certain embodiments, the antibody binds to CD19 (e.g., human CD19). In certain embodiments, the antigen binding chain is designated as "VL-TRAC".

VH-TRBC

In certain embodiments, a presently disclosed HI-TCR comprises an antigen binding chain that comprises an extracellular antigen-binding domain of a $V_H$ domain of an antibody and a constant domain of TRBC. In certain embodiments, the antibody binds to CD19 (e.g., human CD19). In certain embodiments, the antigen binding chain is designated as "VH-TRBC".

3. Immunoresponsive Cells

The presently disclosed subject matter provides immunoresponsive cells comprising a presently disclosed HI-TCR. In certain embodiments, the HI-TCR is capable of activating the immunoresponsive cell. Upon binding to the antigen, the immunoresponsive cells exhibit cytolytic effects towards cells bearing the antigen. In certain embodiments, the immunoresponsive cells comprising the HI-TCR exhibits comparable or better therapeutic potency compared to cells comprising a chimeric antigen receptor (CAR) targeting the same antigen. In certain embodiments, the immunoresponsive cells comprising the HI-TCR exhibit comparable or better cytolytic effects compared to cells comprising a chimeric antigen receptor (CAR) targeting the same antigen. In certain embodiments, the immunoresponsive cells comprising the HI-TCR secrete anti-tumor cytokines. The cytokines secreted by the immunoresponsive cells include, but are not limited to, TNFα, IFNγ and IL2.

The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of immunoresponsive cells of the lymphoid lineage include T cells, Natural Killer T (NKT) cells, and precursors thereof including embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, helper T cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. A patient's own T cells may be genetically modified to target specific antigens through the introduction of an HI-TCR. In certain embodiments, the immunoresponsive cell is a T cell. The T cell can be a CD4$^+$ T cell or a CD8+ T cell. In certain embodiments, the T cell is a CD4+ T cell. In certain embodiments, the T cell is a CD8+ T cell.

In certain embodiments, the immunoresponsive cell comprises an exogenous or a recombinant (e.g., the cell is transduced with) at least one co-stimulatory ligand. In certain embodiments, the immunoresponsive cell co-expresses the HI-TCR and the at least one exogenous co-stimulatory ligand. The interaction between the HI-TCR and at least one exogenous co-stimulatory ligand provides a non-antigen-specific signal important for full activation of an immunoresponsive cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, but are not limited to, nerve growth factor (NGF), CD40L (CD40L)/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28. In certain embodiments, the at least one co-stimulatory ligand is selected from the group consisting of 4-1BBL, CD275, CD80, CD86, CD70, OX40L, CD48, TNFRSF14, and combinations thereof. In certain embodiments, the immunoresponsive cell comprises or consists of one exogenous or recombinant co-stimulatory ligand. In certain embodiments, the one exogenous or recombinant co-stimulatory ligand is 4-1BBL or CD80. In certain embodiments, the one exogenous or recombinant co-stimulatory ligand is 4-1BBL. In certain embodiments, the immunoresponsive cell comprises or consists of two exogenous or recombinant co-stimulatory ligands. In certain embodiments, the two exogenous or recombinant co-stimulatory ligands are 4-1BBL and CD80.

In certain embodiments, the immunoresponsive cell can comprise or be transduced with at least one chimeric co-stimulatory receptor (CCR). As used herein, the term "chimeric co-stimulatory receptor" or "CCR" refers to a chimeric receptor that binds to an antigen, and, upon its binding to the antigen, provides a co-stimulatory signal to a cell (e.g., a T cell) comprising the CCR, but does not alone provide an activation signal to the cell. CCR is described in Krause, et al., J. Exp. Med. (1998); 188(4):619-626, and US20020018783, which is incorporated by reference in its entirety. CCRs mimic co-stimulatory signals, but unlike, CARs, do not provide a T-cell activation signal, e.g., CCRs lack a CD3ζ polypeptide. CCRs provide co-stimulation, e.g., a CD28-like signal, in the absence of the natural co-stimulatory ligand on the antigen-presenting cell. A combinatorial antigen recognition, i.e., use of a CCR in combination with a CAR, can augment T-cell reactivity against the dual-antigen expressing T cells, thereby improving selective tumor targeting. See WO2014/055668, which is incorporated by reference in its entirety. Kloss et al., describe a strategy that integrates combinatorial antigen recognition, split signaling, and, critically, balanced strength of T-cell activation and co-stimulation to generate T cells that eliminate target cells that express a combination of antigens while sparing cells that express each antigen individually (Kloss et al., Nature Biotechnology (2013); 31(1):71-75, the content of which is incorporated by reference in its entirety). With this approach, T-cell activation requires CAR-mediated recognition of one antigen, whereas co-stimulation is independently mediated by a CCR specific for a second antigen. To achieve tumor selectivity, the combinatorial antigen recognition approach diminishes the efficiency of T-cell activation to a level where it is ineffective without rescue provided by simultaneous CCR recognition of the second antigen.

In certain embodiments, the CCR comprises an extracellular antigen-binding domain that binds to a second antigen, a transmembrane domain, and a co-stimulatory signaling region that comprises at least one co-stimulatory molecule. In certain embodiments, the CCR does not alone deliver an activation signal to the cell. Non-limiting examples of co-stimulatory molecules include CD28, 4-1BB, OX40, ICOS, DAP-10 and any combination thereof. In certain embodiments, the co-stimulatory signaling region of the CCR comprises one co-stimulatory signaling molecule. In certain embodiments, the one co-stimulatory signaling molecule is CD28. In certain embodiments, the one co-stimulatory signaling molecule is 4-1BB. In certain embodiments, the co-stimulatory signaling region of the CCR comprises two co-stimulatory signaling molecules. In certain embodiments, the two co-stimulatory signaling molecules are CD28 and 4-1BB. A second antigen is selected so that expression of both the first antigen and the second antigen is restricted to the targeted cells (e.g., cancerous tissue or cancerous cells). Similar to a CAR, the extracellular antigen-binding domain can be a scFv, a Fab, a F(ab)2, or a fusion protein with a heterologous sequence to form the extracellular antigen-binding domain.

In certain embodiments, the CCR is co-expressed with a HI-TCR binding to an antigen that is different from the antigen to which the CCR binds, e.g., the HI-TCR binds to a first antigen and the CCR binds to a second antigen.

Types of human lymphocytes of the presently disclosed subject matter include, without limitation, peripheral donor lymphocytes, e.g., those disclosed in Sadelain, M., et al. 2003 Nat Rev Cancer 3:35-45 (disclosing peripheral donor lymphocytes genetically modified to express CARs), in Morgan, R. A., et al. 2006 Science 314:126-129 (disclosing peripheral donor lymphocytes genetically modified to express a full-length tumor antigen-recognizing T cell receptor complex comprising the α and β heterodimer), in Panelli, M. C., et al. 2000 J Immunol 164:495-504; Panelli, M. C., et al. 2000 J Immunol 164:4382-4392 (disclosing lymphocyte cultures derived from tumor infiltrating lymphocytes (TILs) in tumor biopsies), and in Dupont, J., et al. 2005 Cancer Res 65:5417-5427; Papanicolaou, G. A., et al. 2003 Blood 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

The presently disclosed immunoresponsive cells are capable of modulating the tumor microenvironment. Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory CD4+ T cells (Tregs), myeloid derived suppressor cells (MDSCs), tumor associated macrophages (TAMs), immune suppressive cytokines including TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. In certain embodiments, at least about 80%, usually at least about 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). In certain embodiments, the cells are collected in a medium comprising 2% fetal calf serum (FCS) or 0.2% bovine serum albumin (BSA) or any other suitable, e.g., sterile, isotonic medium.

4. Vectors

Genetic modification of an immunoresponsive cell (e.g., a T cell or an NKT cell) can be accomplished by transducing a substantially homogeneous cell composition with a recombinant DNA construct. In certain embodiments, a retroviral vector (either gamma-retroviral or lentiviral) is employed for the introduction of the DNA construct into the cell. For example, a polynucleotide encoding an HI-TCR can be cloned into a retroviral vector and expression can be driven from its endogenous promoter, from the retroviral long terminal repeat, or from a promoter specific for a target cell type of interest. Non-viral vectors may be used as well.

For initial genetic modification of an immunoresponsive cell to include an HI-TCR, a retroviral vector is generally employed for transduction, however any other suitable viral vector or non-viral delivery system can be used. The HI-TCR can be constructed with an auxiliary molecule (e.g., a cytokine) in a single, multicistronic expression cassette, in multiple expression cassettes of a single vector, or in multiple vectors. Examples of elements that create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-κB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) Mol. Cell. Biol. 5:431-437); PA317 (Miller, et al. (1986) Mol. Cell. Biol. 6:2895-2902); and CRIP (Danos, et al. (1988) Proc. Natl. Acad. Sci. USA 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) Blood 80:1418-1422, or culturing with viral supernatant alone or concentrated vector stocks with or without appropriate growth factors and polycations, e.g., by the method of Xu, et al. (1994) Exp. Hemat. 22:223-230; and Hughes, et al. (1992) J. Clin. Invest. 89:1817.

Other transducing viral vectors can be used to modify an immunoresponsive cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263-267, 1996; and Miyoshi et al., Proc. Natl. Acad. Sci. U.S.A. 94:10319, 1997). Other viral vectors that can be used include, for example, adenoviral, lentiviral, and adena-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; LeGal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for genetic modification of an immunoresponsive cell. For example, a nucleic acid molecule can be introduced into an immunoresponsive cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases, CRISPR). Transient expression may be obtained by RNA electroporation. In certain embodiments, recombinant receptors can be introduced by a transposon-based vector. In certain embodiments, the transposon-based vector comprises a transposon (a.k.a. a transposable element). In certain embodiments, the transposon can be recognized by a transposase. In certain embodiments, the transposase is a Sleeping Beauty transposase.

Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to form a single-guide RNA (sgRNA). This sgRNA can be joined together with the Cas9 gene and made into a plasmid in order to be transfected into cells.

A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of basepairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome.

Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome. cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

6. Genome Editing Methods

In certain non-limiting embodiments, an HI-TCR, a costimulatory ligand, a CCR or any other molecule/transgene disclosed herein is expressed by an immunoresponsive cell through a modified genomic locus. In certain embodiments, an expression cassette of the transgene is integrated into a targeted genomic locus of an immunoresponsive cell through targeted genome editing methods. In certain embodiments, the targeted genomic locus can be CD3δ, CD3ε, CD247, B2M, TRAC, TRBC1, TRBC2, TRGC1 and/or TRGC2 loci.

6.1. Engineering T Cell Receptor Locus

In certain embodiments, an HI-TCR is expressed by an immunoresponsive cell through a modified endogenous T cell receptor locus. In certain embodiments, an HI-TCR expression cassette is integrated at an endogenous T cell receptor locus. In certain embodiments, the HI-TCR expression cassette is integrated within the T cell receptor alpha locus (TRA, GenBank ID: 6955). In certain embodiments, the HI-TCR expression cassette is integrated within the T cell receptor beta locus (TRB, GenBank ID: 6957). In certain embodiments, the HI-TCR expression cassette is integrated within the T cell receptor gamma locus (TRG, GenBank ID: 6965).

In certain embodiments, the HI-TCR expression cassette comprises an extracellular antigen-binding domain that is integrated in the first exon of a TCR constant domain locus, so that the extracellular antigen-binding domain and the TCR constant domain are comprised in one antigen binding chain of the HI-TCR. In certain embodiments, the TCR constant domain locus can be TRAC, TRBC1, TRBC2, TRGC1, or TRGC2. In certain embodiments, the HI-TCR expression cassette comprises an extracellular antigen-binding domain that is integrated in the first exon of a TRAC locus, so that the extracellular antigen-binding domain and a TRAC peptide are comprised in a first antigen binding chain of the HI-TCR. In certain embodiments, the HI-TCR expression cassette further comprises a second antigen binding chain, which optionally comprises an extracellular antigen-binding domain and a TRBC peptide. In certain embodiments, the HI-TCR expression cassette comprises an extracellular antigen-binding domain that is integrated in the first exon of a TRBC locus, so that the extracellular antigen-binding domain and a TRBC peptide are comprised in a first antigen binding chain of the HI-TCR. In certain embodiments, the HI-TCR expression cassette further comprises a second antigen binding chain, which optionally comprises an extracellular antigen-binding domain and a TRAC peptide. In certain embodiments, the expression cassette comprises elements that create polycistronic expression cassette, e.g., a cleavable peptide, e.g., a 2A peptide.

In certain embodiments, the recombinant TCR is expressed from an expression cassette placed in an endogenous TRAC locus and/or a TRBC locus of an immunoresponsive cell. In certain embodiments, the placement of the recombinant TCR expression cassette disrupts or abolishes the endogenous expression of a TCR comprising a native TCR α chain and/or a native TCR β chain in the immunoresponsive cell. In certain embodiments, the placement of the recombinant TCR expression cassette prevents or eliminates mispairing between the recombinant TCR and a native TCR α chain and/or a native TCR β chain in the immunoresponsive cell.

Any suitable genetic editing methods and systems can be used to modify an endogenous T cell receptor locus. The genome editing methods disclosed in Section 4 can be used to modify the endogenous T cell receptor locus. In certain embodiments, a CRISPR system is used to modify T cell receptor locus. In certain embodiments, the CRISPR system targets exon 1 of a human TRAC locus. In certain embodiments, the CRISPR system comprises a guide RNA (gRNA) that targets exon 1 of a human TRAC locus.

In certain embodiments, a zinc-finger nuclease is used to modify an endogenous T cell receptor locus. In certain embodiments, a TALEN system is used to modify an endogenous T cell receptor locus.

In certain embodiments, when one endogenous T cell receptor locus in a cell is modified to express one or more antigen binding chain of an HI-TCR, one or more other endogenous T cell receptor locus in the cell are modified to eliminate the endogenous expression of the endogenous TCR chain. In certain embodiments, the one or more other endogenous T cell receptor locus are further modified to express a gene of interest, e.g., an anti-tumor cytokine (e.g., IL-2, IL-12, TNFα, and INFγ), a co-stimulatory molecule ligand (e.g., 4-1BBL), a tracking gene (e.g., eGFP) or a suicide gene.

6.2. Modifying Gene Expression Through Genome Editing of a Promoter or a Transcription Terminator In certain non-limiting embodiments, the expression of an HI-TCR expression cassette integrated into a targeted genomic locus is driven by an endogenous promoter/enhancer of the genomic locus. In certain embodiments, the expression of an HI-TCR expression cassette integrated into a targeted genomic locus is driven by a modified promoter/enhancer introduced to the genomic locus. Any targeted genome editing methods can be used to modify the promoter/enhancer region of a targeted genomic locus, and thereby enhancing or modifying the expression of an HI-TCR in an immunoresponsive cell. In certain embodiments, the modification comprises replacement of an endogenous promoter with a constitutive promoter or an inducible promoter, or insertion of a constitutive promoter or inducible promoter to the promoter region of a targeted genomic locus. In certain embodiments, a constitutive promoter is positioned on a targeted genomic locus to drive gene expression of the HI-TCR. Eligible constitutive promoters include, but are not limited to, a CMV promoter, an EF1a promoter, a SV40 promoter, a PGK1 promoter, a Ubc promoter, a beta-actin promoter, and a CAG promoter. Alternatively or additionally, a conditional or inducible promoter is positioned on a targeted genomic locus to drive gene expression of the HI-TCR. Non-limiting examples of conditional promoters include a tetracycline response element (TRE) promoter and an estrogen response element (ERE) promoter. In addition, enhancer elements can be placed in regions other than the promoter region.

In certain non-limiting embodiments, the expression of an HI-TCR expression cassette integrated into a targeted genomic locus is regulated by an endogenous transcription terminator of the genomic locus. In certain embodiments, the expression of an HI-TCR expression cassette integrated into a targeted genomic locus is regulated by a modified transcription terminator introduced to the genomic locus. Any targeted genome editing methods can be used to modify the transcription terminator region of a targeted genomic locus, and thereby modifying the expression of an HI-TCR in an immunoresponsive cell. In certain embodiments, the modification comprises replacement of an endogenous transcription terminator with an alternative transcription terminator, or insertion of an alternative transcription terminator to the transcription terminator region of a targeted genomic locus. In certain embodiments, the alternative transcription terminator comprises a 3'UTR region or a ploy A region of a gene. In certain embodiments, the alternative transcription terminator is endogenous. In certain embodiments, the alternative transcription terminator is exogenous. In certain embodiments, alternative transcription terminators include, but are not limited to, a TK transcription terminator, a GCSF transcription terminator, a TCRA transcription terminator, an HBB transcription terminator, a bovine growth hormone transcription terminator, an SV40 transcription terminator and a P2A element.

Any targeted genome editing methods can be used to modify the promoter/enhancer region and/or the transcription terminator region of a targeted genomic locus. In certain embodiments, a CRISPR system is used to modify the promoter/enhancer region and/or the transcription terminator region of a targeted genomic locus. In certain embodiments, zinc-finger nucleases are used to modify the promoter/enhancer region and/or the transcription terminator region of a targeted genomic locus. In certain embodiments, a TALEN system is used to modify the promoter/enhancer region and/or the transcription terminator region of a targeted genomic locus.

Methods for delivering the genome editing agents/systems can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

Modification can be made anywhere within a targeted genomic locus, or anywhere that can impact gene expression of a targeted genomic locus. In certain embodiments, the modification occurs upstream of the transcriptional start site of a targeted genomic locus. In certain embodiments, the modification occurs between the transcriptional start site and the protein coding region of a targeted genomic locus. In certain embodiments, the modification occurs downstream of the protein coding region of a targeted genomic locus. In certain embodiments, the modification occurs upstream of the transcriptional start site of a targeted genomic locus, wherein the modification produces a new transcriptional start site.

7. Polypeptides and Analogs

Also included in the presently disclosed subject matter are polypeptides (e.g., CD19, CD8, CD28, CD3ζ, CD40, 4-1BB, OX40, CD84, CD166, CD8a, CD8b, ICOS, ICAM-1, TRAC, TRBC1, TRBC2, TRGC1, TRGC2, CD3γ, CD3δ, CD3ε and CTLA-4) or fragments thereof that are modified in ways that enhance their anti-neoplastic activity when expressed in an immunoresponsive cell. The presently disclosed subject matter provides methods for optimizing an amino acid sequence or nucleic acid sequence by producing an alteration in the sequence. Such alterations may include certain mutations, deletions, insertions, or post-translational modifications. The presently disclosed subject matter further includes analogs of any naturally-occurring polypeptide disclosed herein (including, but not limited to, CD19, CD8, CD28, CD3ζ, CD40, 4-1BB, OX40, CD84, CD166, CD8a, CD8b, ICOS, ICAM-1, TRAC, TRBC1, TRBC2, TRGC1, TRGC2, CD3γ, CD3δ, CD3ε and CTLA-4). Analogs can differ from a naturally-occurring polypeptide disclosed herein by amino acid sequence differences, by post-translational modifications, or by both. Analogs can exhibit at least about 85%, about 90%, about 91%, about 92%, about 93%, about 94%, about 95%, about 96%, about 97%, about 98%, about 99% or more homologous to all or part of a naturally-occurring amino, acid sequence of the presently disclosed subject matter. The length of sequence comparison is at least 5, 10, 15 or 20 amino acid residues, e.g., at least 25, 50, or 75 amino acid residues, or more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., β or γ amino acids.

In addition to full-length polypeptides, the presently disclosed subject matter also provides fragments of any one of the polypeptides or peptide domains disclosed herein. As used herein, the term "a fragment" means at least 5, 10, 13, or 15 amino acids. In certain embodiments, a fragment comprises at least 20 contiguous amino acids, at least 30 contiguous amino acids, or at least 50 contiguous amino acids. In certain embodiments, a fragment comprises at least 60 to 80, 100, 200, 300 or more contiguous amino acids. Fragments can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein disclosed herein. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. In certain embodiments, the protein analogs are relatively resistant to in vivo degradation, resulting in a more prolonged therapeutic effect upon administration. Assays for measuring functional activity include, but are not limited to, those described in the Examples below.

8. Administration

Compositions comprising the presently disclosed immunoresponsive cells can be provided systemically or directly to a subject for inducing and/or enhancing an immune response to an antigen and/or treating and/or preventing a neoplasia, pathogen infection, or infectious disease. In certain embodiments, the presently disclosed immunoresponsive cells or compositions comprising thereof are directly injected into an organ of interest (e.g., an organ affected by a neoplasia). Alternatively, the presently disclosed immunoresponsive cells or compositions comprising thereof are provided indirectly to the organ of interest, for example, by administration into the circulatory system (e.g., the tumor vasculature). Expansion and differentiation agents can be provided prior to, during or after administration of the cells or compositions to increase production of T cells, NKT cells, or CTL cells in vitro or in vivo.

The presently disclosed immunoresponsive cells can be administered in any physiologically acceptable vehicle, normally intravascularly, although they may also be introduced into bone or other convenient site where the cells may find an appropriate site for regeneration and differentiation (e.g., thymus). Usually, at least about $1\times10^5$ cells will be administered, eventually reaching about $1\times10^{10}$ or more. The presently disclosed immunoresponsive cells can comprise a purified population of cells. Those skilled in the art can readily determine the percentage of the presently disclosed immunoresponsive cells in a population using various well-known methods, such as fluorescence activated cell sorting (FACS). Suitable ranges of purity in populations comprising the presently disclosed immunoresponsive cells are about 50% to about 55%, about 5% to about 60%, and about 65% to about 70%. In certain embodiments, the purity is about 70% to about 75%, about 75% to about 80%, or about 80% to about 85%. In certain embodiments, the purity is about 85% to about 90%, about 90% to about 95%, and about 95% to about 100%. Dosages can be readily adjusted by those skilled in the art (e.g., a decrease in purity may require an increase in dosage). The cells can be introduced by injection, catheter, or the like.

The presently disclosed compositions can be pharmaceutical compositions comprising the presently disclosed immunoresponsive cells or their progenitors and a pharmaceutically acceptable carrier. Administration can be autologous or heterologous. For example, immunoresponsive cells, or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition of the presently disclosed subject matter (e.g., a pharmaceutical composition comprising a presently disclosed immunoresponsive cell), it can be formulated in a unit dosage injectable form (solution, suspension, emulsion).

9. Formulations

Compositions comprising the presently disclosed immunoresponsive cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified immunoresponsive cells in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the genetically modified immunoresponsive cells or their progenitors.

The compositions can be isotonic, i.e., they can have the same osmotic pressure as blood and lacrimal fluid. The desired isotonicity of the compositions may be accomplished using sodium chloride, or other pharmaceutically acceptable agents such as dextrose, boric acid, sodium tartrate, propylene glycol or other inorganic or organic solutes. Sodium chloride can be particularly for buffers containing sodium ions.

Viscosity of the compositions, if desired, can be maintained at the selected level using a pharmaceutically acceptable thickening agent. For example, methylcellulose is is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

The quantity of cells to be administered will vary for the subject being treated. In a one embodiment, between about $10^4$ and about $10^{10}$, between about $10^5$ and about $10^9$, or between about $10^6$ and about $10^8$ of the presently disclosed immunoresponsive cells are administered to a human subject. More effective cells may be administered in even smaller numbers. In certain embodiments, at least about $1\times10^8$, about $2\times10^8$, about $3\times10^8$, about $4\times10^8$, or about $5\times10^8$ of the presently disclosed immunoresponsive cells are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods. Typically, any additives (in addition to the active cell(s) and/or agent (s)) are present in an amount of 0.001 to 50% (weight) solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, or about 0.05 to about 5 wt %. For any composition to be administered to an animal or human, the followings can be determined: toxicity such as by determining the lethal dose (LD) and LD50 in a suitable animal model e.g., rodent such as mouse; the dosage of the composition(s), concentration of components therein and timing of administering the composition (s), which elicit a suitable response. Such determinations do not require undue experimentation from the knowledge of the skilled artisan, this disclosure and the documents cited herein. And, the time for sequential administrations can be ascertained without undue experimentation.

10. Methods of Treatment

The presently disclosed subject matter provides methods for inducing and/or increasing an immune response in a subject in need thereof. The presently disclosed immunoresponsive cells and compositions comprising thereof can be used for treating and/or preventing a neoplasia in a subject. The presently disclosed immunoresponsive cells and compositions comprising thereof can be used for prolonging the survival of a subject suffering from a neoplasia. The presently disclosed immunoresponsive cells and compositions comprising thereof can also be used for treating and/or preventing a pathogen infection or other infectious disease in a subject, such as an immunocompromised human subject. Such methods comprise administering the presently disclosed immunoresponsive cells in an amount effective or a composition (e.g., pharmaceutical composition) comprising thereof to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

In certain embodiments, immunoresponsive cells comprising a HI-TCR disclosed herein can be used to treat a subject having tumor cells with a low expression level of a surface antigen, .e.g, from a relapse of a disease, wherein the subject received treatment which leads to residual tumor cells. In certain embodiments, the tumor cells have low density of a target molecule on the surface of the tumor cells In certain embodiments, a target molecule having a low density on the cell surface has a density of less than about 5,000 molecules per cell, less than about 4,000 molecules per cell, less than about 3,000 molecules per cell, less than about 2,000 molecules per cell, less than about 1,500 molecules per cell, less than about 1,000 molecules per cell, less than about 500 molecules per cell, less than about 200 molecules per cell, or less than about 100 molecules per cell. In certain embodiments, a target molecule having a low density on the cell surface has a density of less than about 2,000 molecules per cell. In certain embodiments, a target molecule having a low density on the cell surface has a density of less than about 1,500 molecules per cell. In certain embodiments, a target molecule having a low density on the cell surface has a density of less than about 1,000 molecules per cell. In certain embodiments, a target molecule having a low density on the cell surface has a density of between about 4,000 molecules per cell and about 2,000 molecules per cell, between about 2,000 molecules per cell and about 1,000 molecules per cell, between about 1,500 molecules per cell and about 1,000 molecules per cell, between about 2,000 molecules per cell and about 500 molecules per cell, between about 1,000 molecules per cell and about 200 molecules per cell, or between about 1,000 molecules per cell and about 100 molecules per cell. In certain embodiments, immunoresponsive cells comprising a HI-TCR disclosed herein can be used to treat a subject having a relapse of a disease, wherein the subject received immunoresponsive cells (e.g., T cells) comprising a CAR comprising an intracellular signaling domain that comprises a co-stimulatory signaling domain comprising a 4-1BB polypeptide (e.g., a 4-1BBz CAR). In certain embodiments, the tumor cells have a low density of a tumor specific antigen on the surface of the tumor cells. In certain embodiments, the disease is CD19$^+$ ALL. In certain embodiments, the tumor cells have a low density of CD19 on the tumor cells. Such methods comprise administering the presently disclosed immunoresponsive cells in an amount effective or a composition (e.g., pharmaceutical composition) comprising thereof to achieve the desired effect, alleviation of an existing condition or prevention of recurrence.

An "effective amount" (or, "therapeutically effective amount") is an amount sufficient to effect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific T cells, cell doses in the range of about $10^6$-$10^{10}$ (e.g., about $10^9$) are typically infused. Upon administration of the presently disclosed cells into the host and subsequent differentiation, T cells are induced that are specifically directed against the specific antigen. The modified cells can be administered by any method known in the art including, but not limited to, intravenous, subcutaneous, intranodal, intratumoral, intrathecal, intrapleural, intraperitoneal and directly to the thymus.

The presently disclosed subject matter provides methods for treating and/or preventing a neoplasia in a subject. The method can comprise administering an effective amount of the presently disclosed immunoresponsive cells or a composition comprising thereof to a subject having a neoplasia.

Non-limiting examples of neoplasia include blood cancers (e.g. leukemias, lymphomas, and myelomas), ovarian cancer, breast cancer, bladder cancer, brain cancer, colon cancer, intestinal cancer, liver cancer, lung cancer, pancreatic cancer, prostate cancer, skin cancer, stomach cancer, glioblastoma, throat cancer, melanoma, neuroblastoma, adenocarcinoma, glioma, soft tissue sarcoma, and various carcinomas (including prostate and small cell lung cancer). Suitable carcinomas further include any known in the field of oncology, including, but not limited to, astrocytoma, fibrosarcoma, myxosarcoma, liposarcoma, oligodendroglioma, ependymoma, medulloblastoma, primitive neural ectodermal tumor (PNET), chondrosarcoma, osteogenic sarcoma, pancreatic ductal adenocarcinoma, small and large cell lung adenocarcinomas, chordoma, angiosarcoma, endotheliosarcoma, squamous cell carcinoma, bronchoalveolarcarcinoma, epithelial adenocarcinoma, and liver metastases thereof, lymphangiosarcoma, lymphangioendotheliosarcoma, hepatoma, cholangiocarcinoma, synovioma, mesothelioma, Ewing's tumor, rhabdomyosarcoma, colon carcinoma, basal cell carcinoma, sweat gland carcinoma, papillary carcinoma, sebaceous gland carcinoma, papillary adenocarcinoma, cystadenocarcinoma, medullary carcinoma, bronchogenic carcinoma, renal cell carcinoma, bile duct carcinoma, choriocarcinoma, seminoma, embryonal carcinoma, Wilms' tumor, testicular tumor, medulloblastoma, craniopharyngioma, ependymoma, pinealoma, hemangioblastoma, acoustic neuroma, oligodendroglioma, meningioma, neuroblastoma, retinoblastoma, leukemia, multiple myeloma, Waldenstrom's macroglobulinemia, and heavy chain disease, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas. In certain embodiments, the neoplasm is selected from the group consisting of blood cancers (e.g. leukemias, lymphomas, and myelomas), ovarian cancer, prostate cancer, breast cancer, bladder cancer, brain cancer, colon cancer, intestinal cancer, liver cancer, lung cancer, pancreatic cancer, prostate cancer, skin cancer, stomach cancer, glioblastoma, and throat cancer. In certain embodiments, the presently disclosed immunoresponsive cells and compositions comprising thereof can be used for treating and/or preventing blood cancers (e.g., leukemias, lymphomas, and myelomas) or ovarian cancer, which are not amenable to conventional therapeutic interventions. In certain embodiments, the neoplasm is a solid tumor.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition is administered to these subjects to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group have a genetic predisposition to neoplasia but have not yet evidenced clinical signs of neoplasia. For instance, women testing positive for a genetic mutation associated with breast cancer, but still of childbearing age, can wish to receive one or more of the immunoresponsive cells described herein in treatment prophylactically to prevent the occurrence of neoplasia until it is suitable to perform preventive surgery.

Additionally, the presently disclosed subject matter provides methods for treating and/or preventing a pathogen infection (e.g., viral infection, bacterial infection, fungal infection, parasite infection, or protozoal infection) in a subject, e.g., in an immunocompromised subject. The method can comprise administering an effective amount of the presently disclosed immunoresponsive cells or a composition comprising thereof to a subject having a pathogen infection. Exemplary viral infections susceptible to treatment include, but are not limited to, Cytomegalovirus (CMV), Epstein Barr Virus (EBV), Human Immunodeficiency Virus (HIV), and influenza virus infections.

Further modification can be introduced to the presently disclosed immunoresponsive cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the presently disclosed immunoresponsive cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T cell elimination by administering anti-EGFR monoclonal antibody (e.g., cetuximab). EGFRt can be covalently joined to the upstream of the antigen-recognizing receptor of a presently disclosed CAR. The suicide gene can be included within the vector comprising nucleic acids encoding a presently disclosed CAR. In this way, administration of a prodrug designed to activate the suicide gene (e.g., a prodrug (e.g., AP1903 that can activate iCasp-9) during malignant T-cell transformation (e.g., GVHD) triggers apoptosis in the suicide gene-activated CAR-expressing T cells. The incorporation of a suicide gene into the a presently disclosed CAR gives an added level of safety with the ability to eliminate the majority of CAR T cells within a very short time period. A presently disclosed immunoresponsive cell (e.g., a T cell) incorporated with a suicide gene can be pre-emptively eliminated at a given timepoint post CAR T cell infusion, or eradicated at the earliest signs of toxicity.

11. Kits

The presently disclosed subject matter provides kits for inducing and/or enhancing an immune response and/or treating and/or preventing a neoplasia or a pathogen infection in a subject. In certain embodiments, the kit comprises an effective amount of presently disclosed immunoresponsive cells or a pharmaceutical composition comprising thereof. In certain embodiments, the kit comprises a sterile container; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In certain non-limiting embodiments, the kit includes an isolated nucleic acid molecule encoding an HI-TCR disclosed herein which is directed toward an antigen of interest in expessible form, which may optionally be comprised in one or more vectors.

If desired, the immunoresponsive cells and/or nucleic acid molecules are provided together with instructions for administering the cells or nucleic acid molecules to a subject having or at risk of developing a neoplasia or pathogen or immune disorder. The instructions generally include information about the use of the composition for the treatment and/or prevention of neoplasia or a pathogen infection. In certain embodiments, the instructions include at least one of the following: description of the therapeutic agent; dosage schedule and administration for treatment or prevention of a neoplasia, pathogen infection, or immune disorder or symptoms thereof; precautions; warnings; indications; counter-indications; over-dosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides disclosed herein, and, as such, may be considered in making and practicing the the presently disclosed subject matter. Particularly useful techniques for particular embodiments will be discussed in the sections that follow.

The following examples are put forth so as to provide those of ordinary skill in the art with a complete disclosure and description of how to make and use the presently disclosed cells and compositions, and are not intended to limit the scope of what the inventors regard as their invention.

Example 1—Targeting T Cells with Endogenous Non-HLA Restricted T Cell Receptor/CD3 Complexes Introduction Specific modifications were made at a TCR locus designed to alter the antigen specificity of human T cells without disrupting or bypassing their CD3 complex, which physiologically controls and regulates T cell activation. In this approach, the T cell lost its endogenous T cell receptor and acquired the ability to recognize antigen independent of HLA, making use of its CD3 complex, which is otherwise bypassed when using CARs. This was accomplished through the targeted disruption of the endogenous TCR combined with the introduction of antigen binding domains into the TRAC locus in such a way as to preserve all components of the natural CD3 complex in their native structure. The recombinant TCR-like molecule (i.e., HI-TCR, FvTCR or HIT-CAR) can harbor variable domains derived from immunoglobulin genes, or alternative ligands, to direct antigen recognition. The recombined receptor signals via the CD3 complex, which can either be intact (i.e., in its physiological composition) or augmented through the non-covalent incorporation of costimulatory domains.

Results

A novel strategy for one-step generation of TCR and TCR-like T cells was developed by integrating a TCR or TCR-like gene with a distinct variable domain for a predetermined antigen. This resulted in the expression of the new TCR/TCR-like gene under the control of the endogenous TCR promoter (alpha, beta or both) with concomitant disruption of surface expression of the endogenous TCR.

A strategy for one-step generation of universal CAR T cells were developed by targeting the integration of a promoter-less CAR gene cassette in the TCR alpha constant chain (TRAC) first exon. This resulted in CAR expression under the control of the endogenous TCR alpha promoter with concomitant disruption of the TCR alpha gene expression, leading to lack of TCR expression at the cell surface. CAR gene targeting at the TRAC locus was accomplished through homologous recombination (HR) by using a site-specific nuclease (e.g. CRISPR/Cas9) and an AAV donor template. Using HR-based gene targeting, the present strategy permitted the generation of T cells with a unique specificity, which was encoded by a chimeric TCR receptor containing a specific antigen-binding domain. The antigen-binding domain was derived from either an Immunoglobulin (i.e. Fv fragment), a ligand for a cell-surface receptor or a TCR ($\alpha\beta$ or $\gamma\delta$). The hybrid Immunoglobulin-TCR chimeric antigen receptor (i.e., HIT-CAR, FvTCR or HI-TCR) or the $\gamma\delta$TCR allowed the T cell to recognize a target cell in an HLA-independent manner. Inserting a new $\alpha\beta$TCR could be accomplished in the same way but would result in HLA-restricted antigen recognition.

Figure 1C:
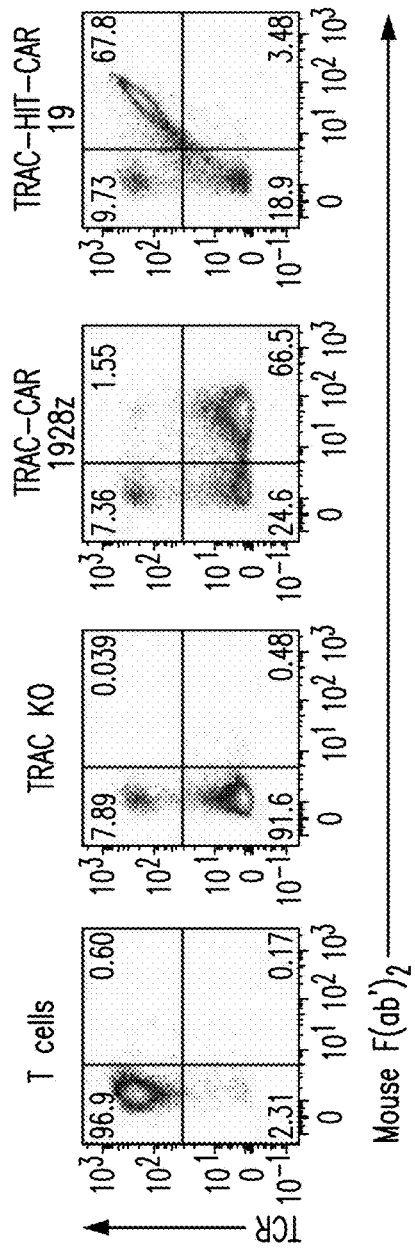
Figure 1D:
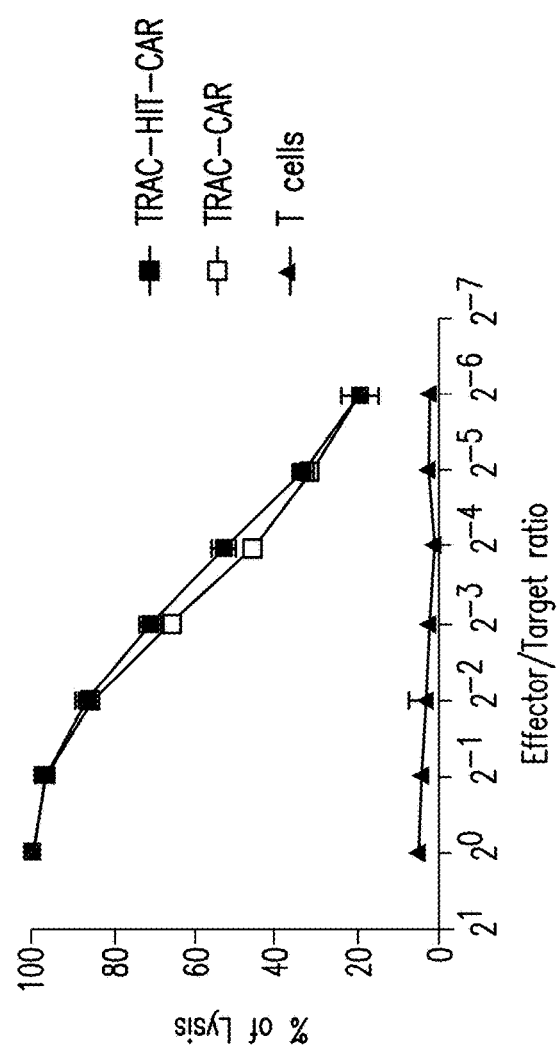
Figure 1E:
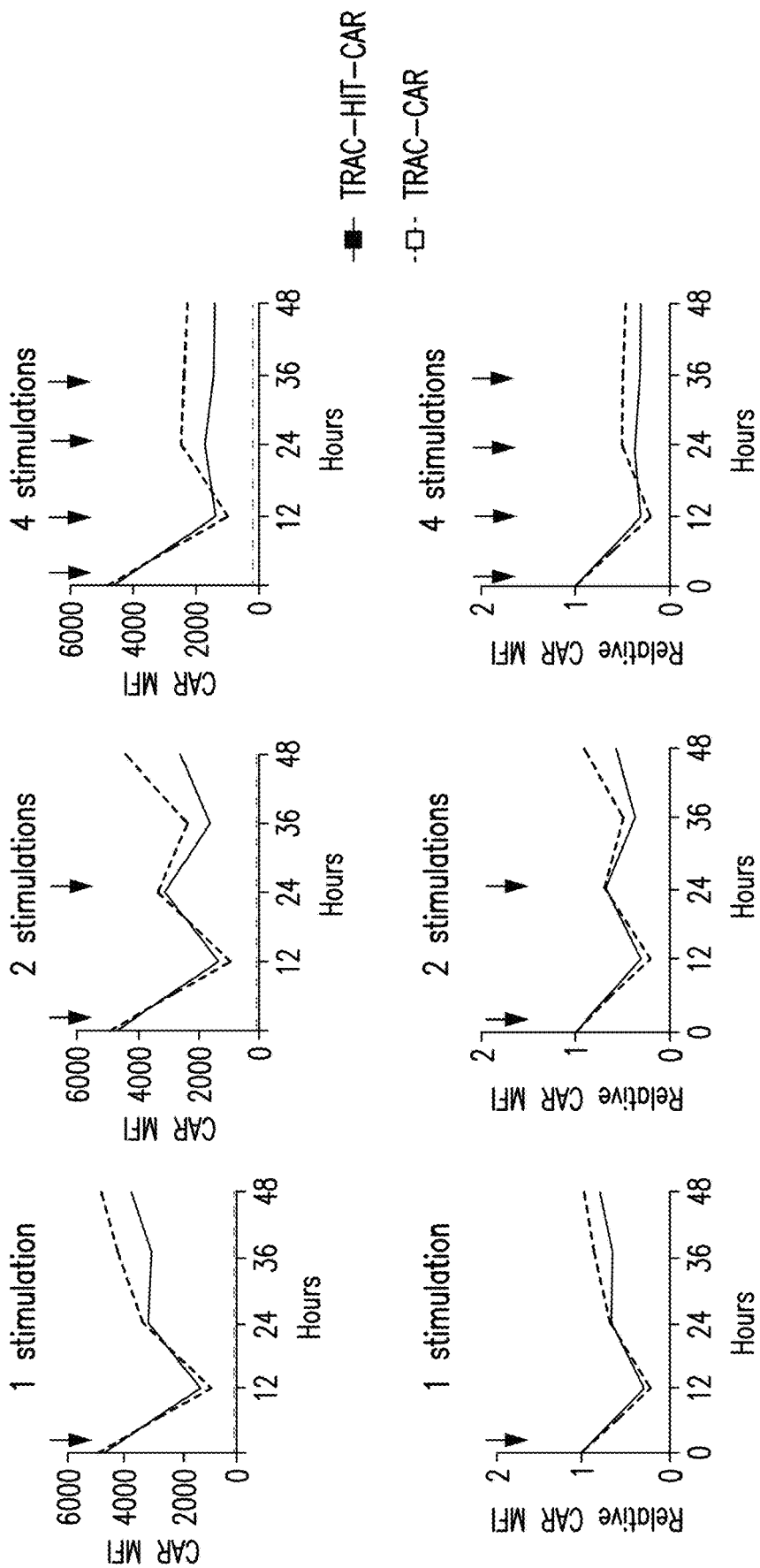

For example, FIG. 1A shows schematic representation of the T Cell Receptor (TCR), the B Cell Receptor (BCR), a Chimeric Antigen Receptor (CAR) and the HLA-Independent TCR-based Chimeric Antigen Receptor (i.e., HIT-CAR, FvTCR or HI-TCR). CRISPR/Cas9-targeted integration of the three receptors into the TRAC locus is shown in FIG. 1B. The engineered HIT-CAR targets CD19. Cell surface expression of HIT-CAR (i.e., HI-TCR) from TRAC locus is show in FIG. 1C. Cytolytic effects and proliferation of HIT-CAR (i.e., HI-TCR or FvTCR) T cells are shown in FIGS. 1D and 1E respectively.

Figure 2A:
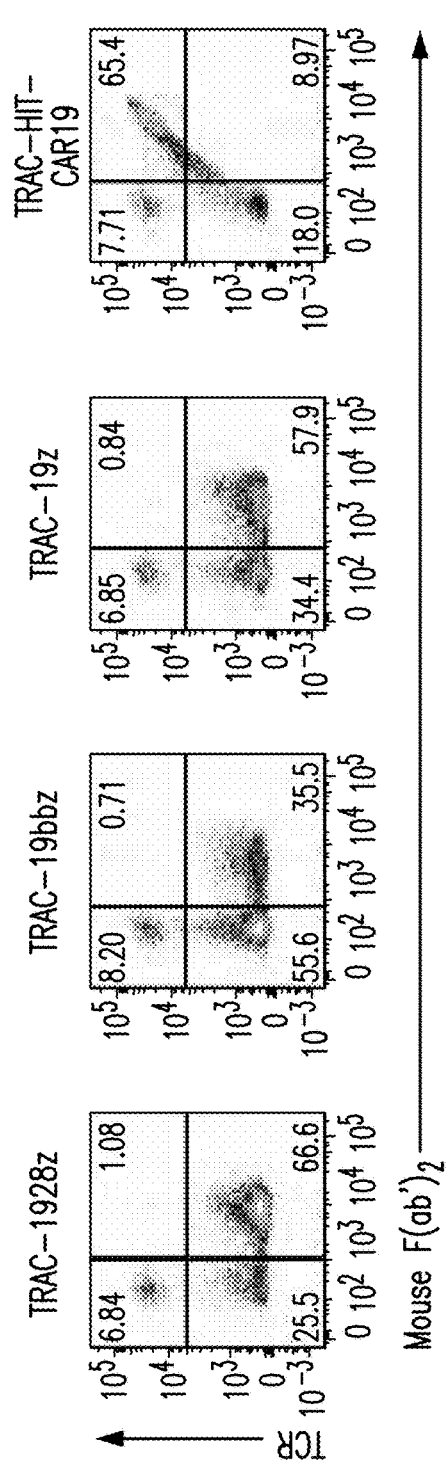
FIGS. 2A-2B depict expression and therapeutic efficacy of HI-TCR.
Figure 2B:
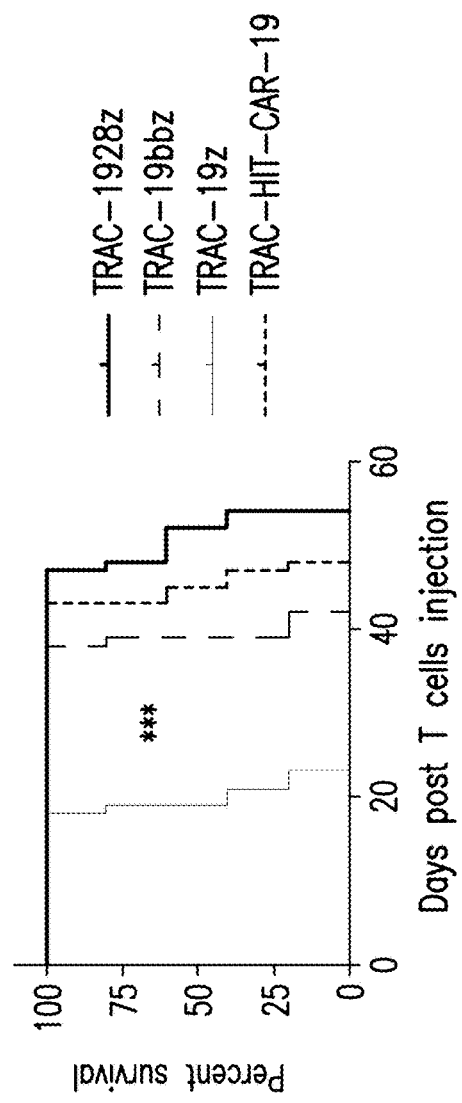

Conditions were established to yield up to 65% of HIT-CAR (i.e., HI-TCR or FvTCR) T cells combining target gene disruption and HIT-CAR (i.e., HI-TCR or FvTCR) targeted insertion in a single step as shown in FIG. 2A. These T cells exhibited in vitro and in vivo tumor lysis activity similar to the previously characterized TRAC-CAR T cells expressing the 1928z CAR as shown in FIG. 2B. In addition, antigen interaction induced down-regulation of the HIT-CAR (i.e., HI-TCR or FvTCR) T cells, which was dependent of the number of antigen-dependent stimulations. As endogenous TCR expression is eliminated at the cell surface, these HIT-CAR (i.e., HI-TCR or FvTCR) T cells were useful for the development of off-the-shelf immunotherapy.

Figure 3D:
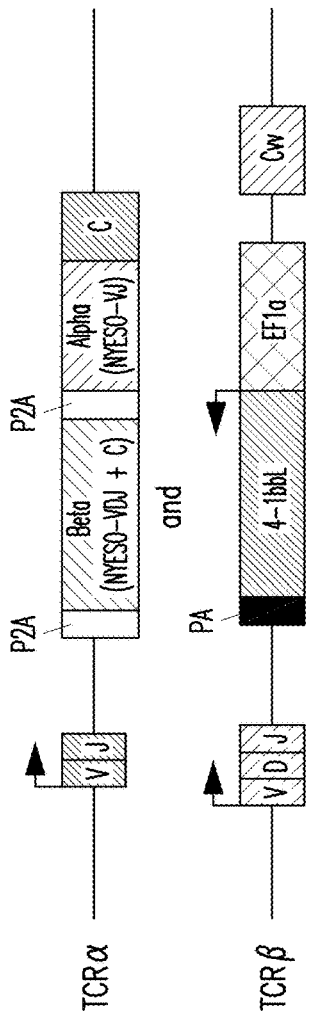
Figure 3E:
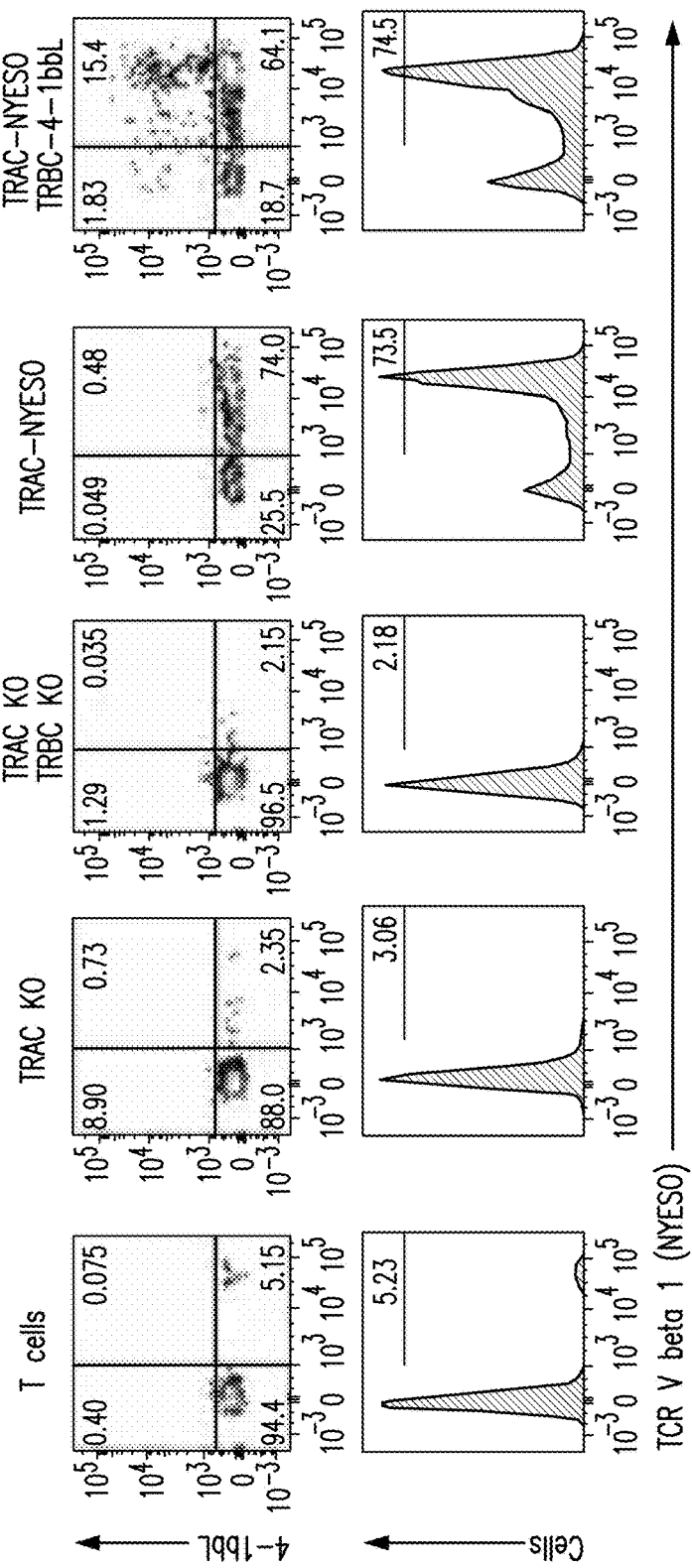

Targets other than CD19 can be employed for immunotherapy. Schematic representation of the NYESO TCR genes integrated into the TCR alpha or beta chain is shown in FIG. 3A. Cell surface expressions of TRAC-NYESO-TCR and TRBC-NYESO-TCR (i.e., HI-TCRs or FvTCRs) are show in FIG. 3B. Representative TCR-V-beta-1 flow cytometry plots 4 days after TRAC or TRBC targeting are shown in FIG. 3B. Cytotoxic activity of the engineered T cells is shown in FIG. 3C. Schematic representation of an alternative design of co-targeting into both the TCR alpha and the TCR beta is shown in FIG. 3D, where a NYESO-HI-TCR was placed in the TRAC locus and 4-1BBL expression cassette was placed in TRBC locus. Cell surface expressions of the TRAC-NYESO-TCR and TRBC-4-1BBL are shown in FIG. 3E.

A variant approach was also provided in which a costimulatory domain is non-covalently inserted into the CD3 complex, which provides supraphysiological antigen sensing and activation. This is achieved by fusing the costimulatory domain to one or both TCR chains. Moreover, two costimulatory dosages are possible, by ether fusing the costimulatory domain to one or both modified TCR chains (i.e., antigen binding chains).

Moreover, HI-TCR exhibited greater sensitivity in comparison to CARs. Human T cells edited to replace endogenous TCR with HI-TCR acquired the ability to engage lower antigen densities and kill such cells. For example, Table 2 shows in vitro cytotoxic activity of HI-TCR cells. HI-TCR or CD19-CAR was introduced at the endogenous TRAC locus of human peripheral T cells via CRISPR/Cas9-mediated gene editing and AAV6 donor vectors. Five days post-gene targeting, T cells (6, 30, or 150 thousands) were incubated with 250 thousands Nalm6 leukemia cells that express different CD19 levels (from very low to high levels). Cells were incubated for 22 h in 500-ul of X-Vivo medium containing serum (without IL2). Co-cultures were analyzed by FACS in the presence of counting beads to determine the total number of Nalm6 cells. Cytotoxic activity is shown as a percentage of Nalm6 killed. E/T: effector (T cells) to target (Nalm6) ratio. The data clearly demonstrate that the HI-TCR can detect lower levels of CD19 antigen than a CAR. This feature can be very useful for antigens with moderate or low expression such as CD22, BCMA, CCR1, CD70, etc., and can also be useful to treat relapse after CAR therapy for any antigen, as the relapse tumor cells frequently show reduced antigen densities on their surface.

TABLE 2

Tumor Cell Killing Percentage

| E/T | HI-TCR | CD19 CAR | CD19 levels |
|---|---|---|---|
| 0.024 | 0 | 0 | very low |
|  | 22.53 | 16.32 | low |
|  | 29.19 | 17.18 | medium |
|  | 38.3 | 32 | high |
| 0.12 | 15.48 | 0.4 | very low |
|  | 51.46 | 53.31 | low |
|  | 54.14 | 63.58 | medium |
|  | 63.28 | 63.38 | high |
| 0.6 | 30.36 | 8.37 | very low |
|  | 68.32 | 77.2 | low |
|  | 77.01 | 79.38 | medium |
|  | 78.72 | 84.37 | high |

Figure 4A:
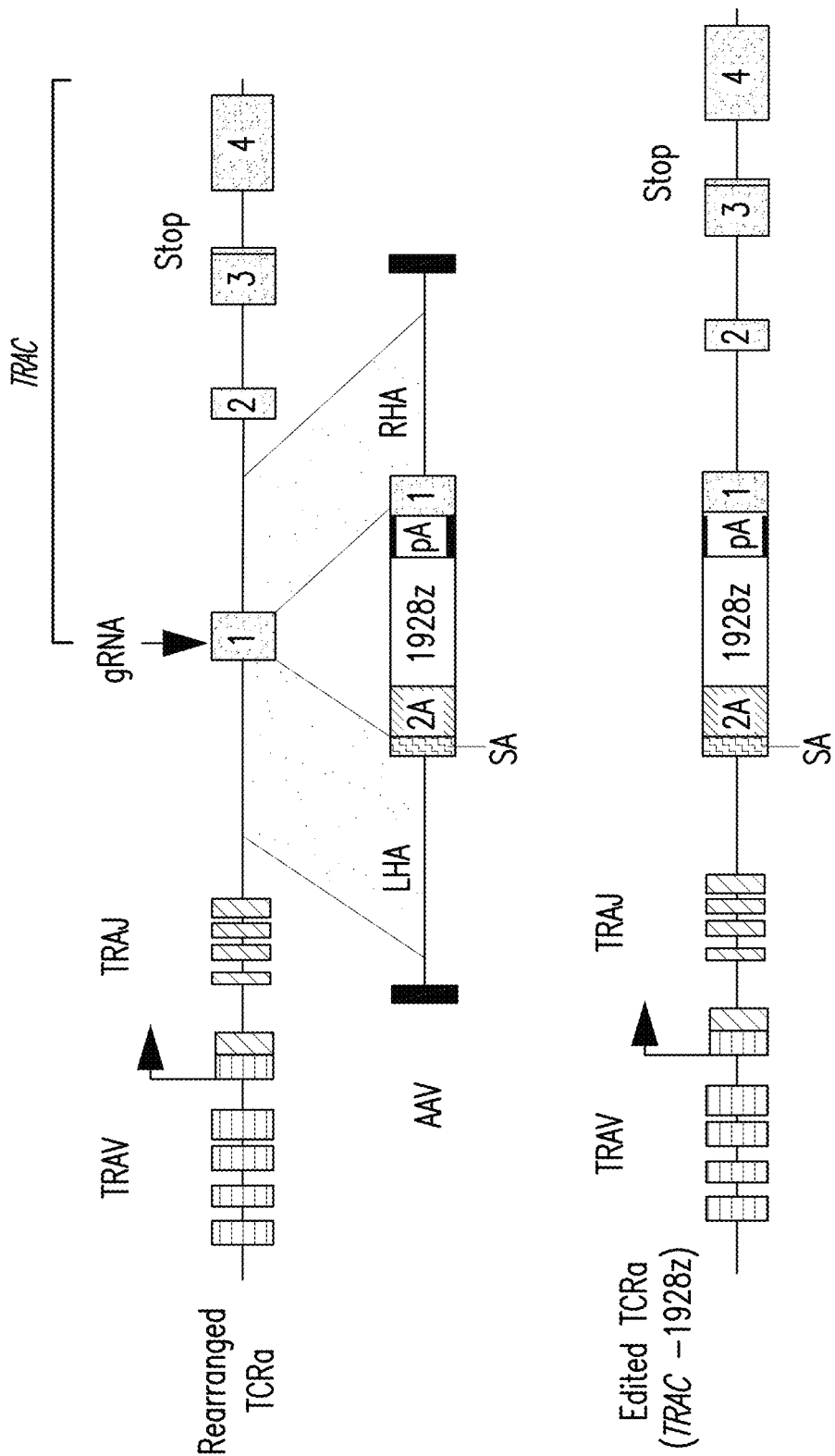
FIGS. 4A-4C depict strategy of integrating a CAR into a TRAC locus and modulation the expression by various transcriptional termination signals/3' untranslated regions (3'UTR).
Figure 4B:
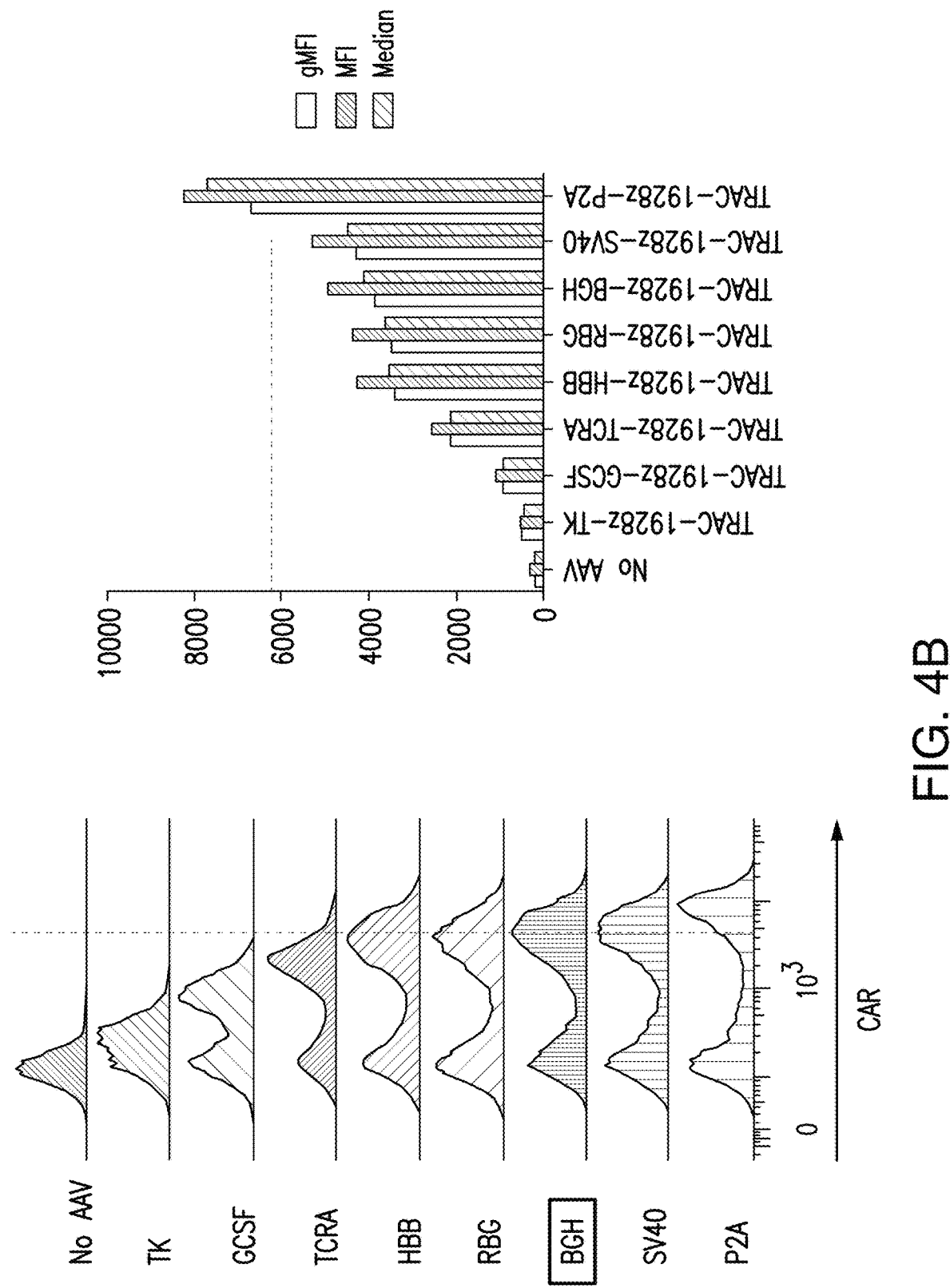
Figure 4C:
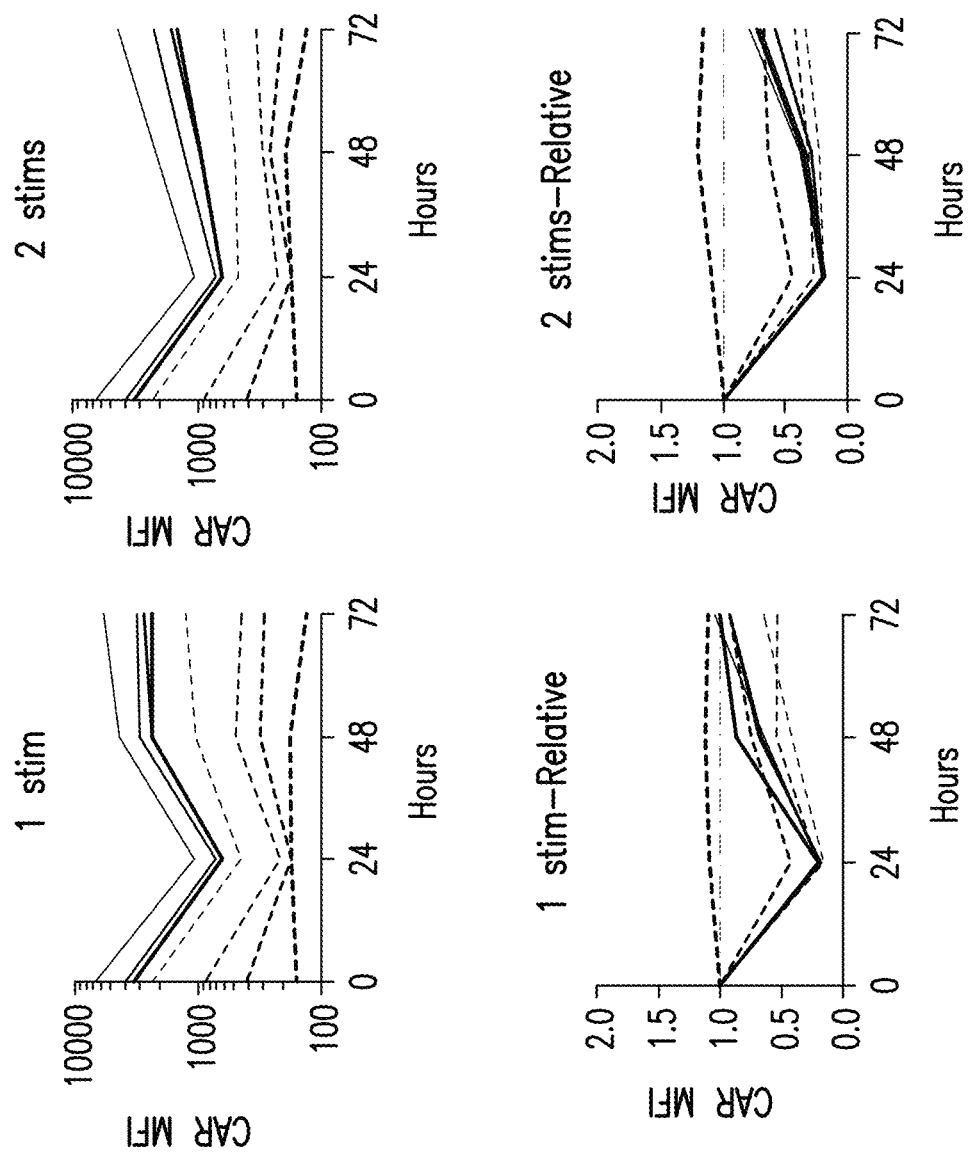
Figure 5A:
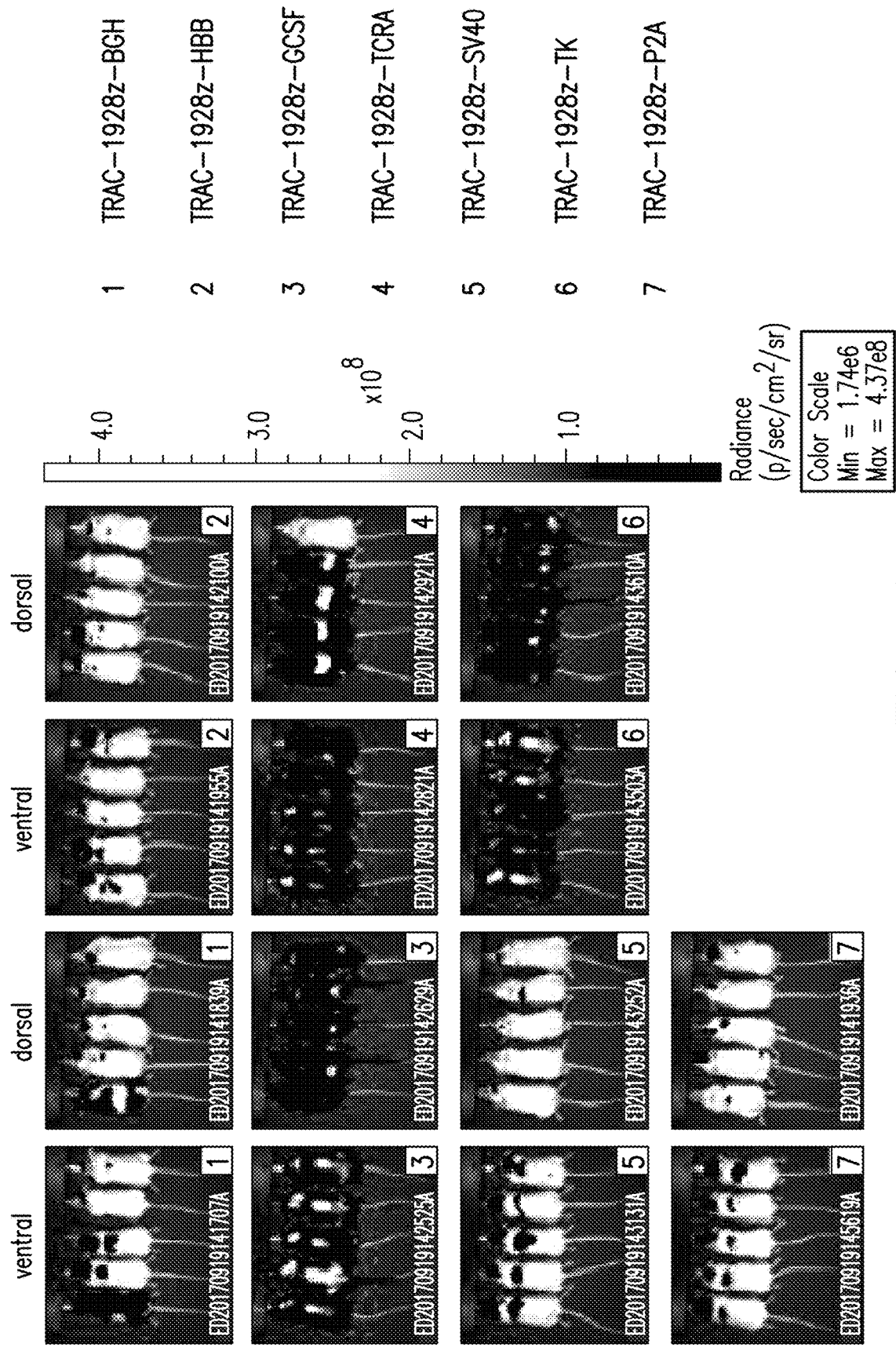
FIGS. 5A and 5B depict efficacy of genetically integrated CARs with different 3'UTR sequences.
Figure 5B:
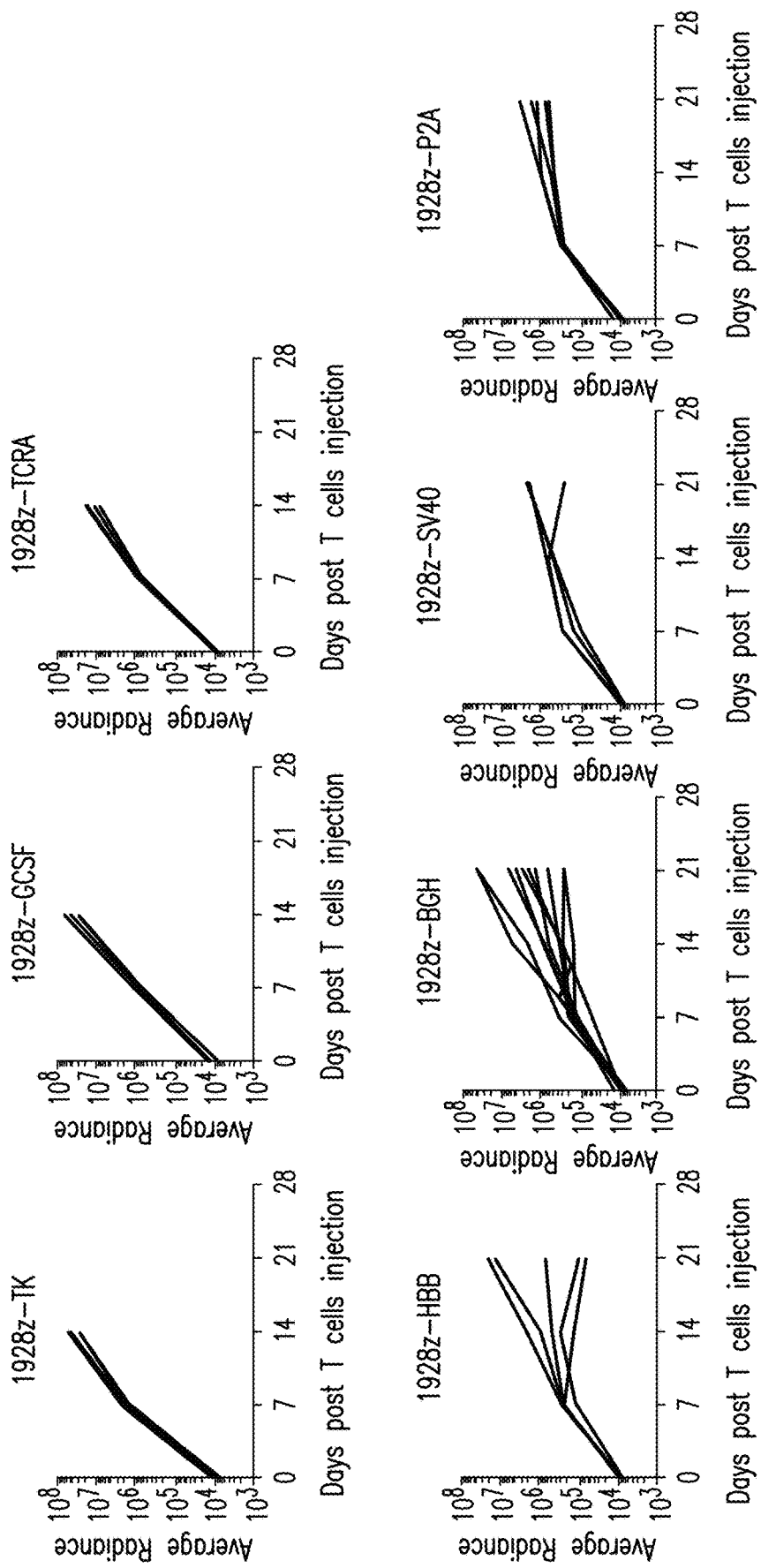

Furthermore, a panel of exogenous and endogenous 3' untranslated regions (3'UTR) were found as capable of regulate precise and predictable gene expression at the TCR locus. For example, FIG. 4A shows schematic representation of the CD28z CAR gene integrated into the TRAC locus. Poly A (black box) corresponds to the segment of the CAR cassette that was modified to test different viral and mammalian 3' UTRs. Using TRAC-CAR T cells expressing the CD28z CAR as a model, certain 3'UTRs were shown to lower the CAR expression compared to the bovine growth hormone (bGH) polyA sequence (FIGS. 4B and 4C), which yielded CAR-T cells with impaired in vivo cytotoxic activity (FIGS. 5A and 5B). Certain other 3'UTRs, including the endogenous TRAC 3'UTR, were shown to increase CAR surface expression levels (FIGS. 4B and 4C), which produced CAR-T cells with improved in vivo cytotoxic activity (FIGS. 5A and 5B). These 3'UTRs can also be used to regulate precise and predictable gene expression of any HI-TCR disclosed herein.

The above-described genetic modifications at the TRAC locus permit the generation of T cells expressing optimal levels of HI-TCR that like the physiological TCR but unlike CARs, take advantage of the endogenous T cell activating machinery (the CD3 complex and downstream signaling elements). This approach can advance both autologous and allogeneic T cell therapies.

Another relevant area where TCR gene editing has relevant applications is T-iPS-derived T cells. T-iPS cells are pluripotent stem cells obtained through reprogramming of peripheral T lymphocytes. These T-iPS cells therefore contain a rearranged T-cell receptor, either an αβ or a γδ TCR, which can be modified using gene-editing technologies. T cells obtained from T-iPS cells through directed differentiation express the rearranged TCR, which can be detected and sequenced. Using this sequence, one can determine the precise location of the rearranged variable domain in the genome of T-iPS cells. Using nucleases that specifically target this rearranged variable domain and a donor DNA containing a TCR variable domain of known specificity, one can replace the endogenous variable domain with the new one. This approach requires two steps of gene editing: one targeting the α (or γ) chain, and the other the β (or δ) chain. The approach can be performed in a single step since only two alleles need to be modified. In addition, using a strategy similar as to the one described for primary human T cells, the TCR chains can be modified to express any HI-TCR disclose herein.

Example 2

Figure 6A:
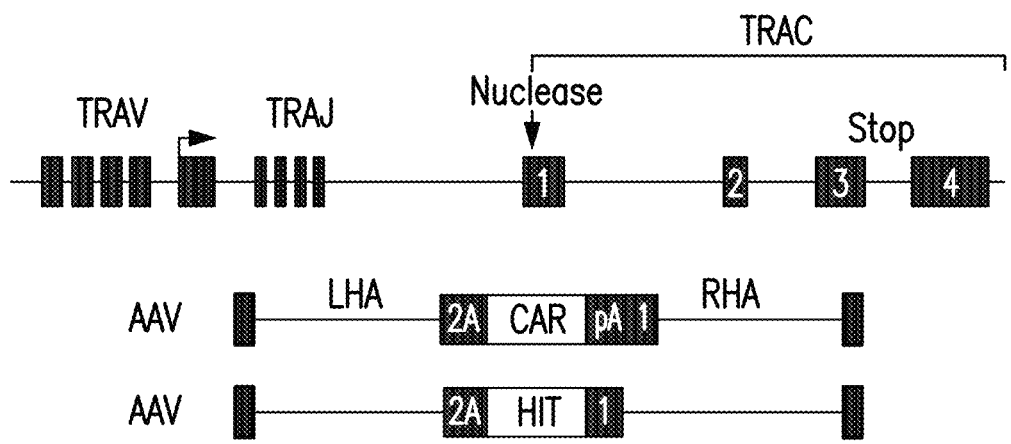
FIGS. 6A-6C depict HIT gene targeting at the TRAC locus in human T cells.
Figure 6B:
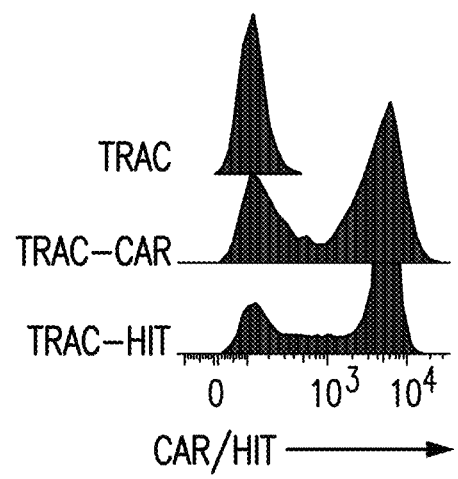
Figure 6C:
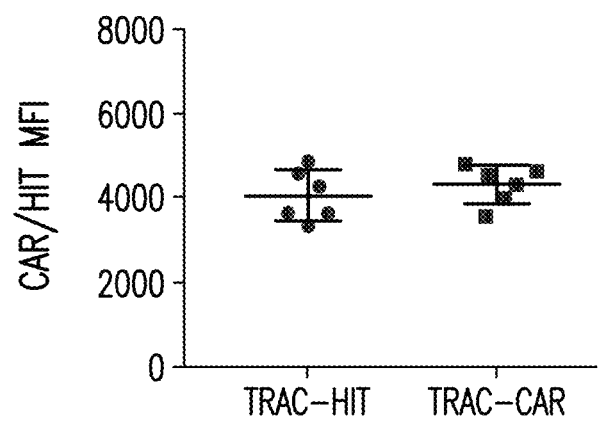
Figure 7A:
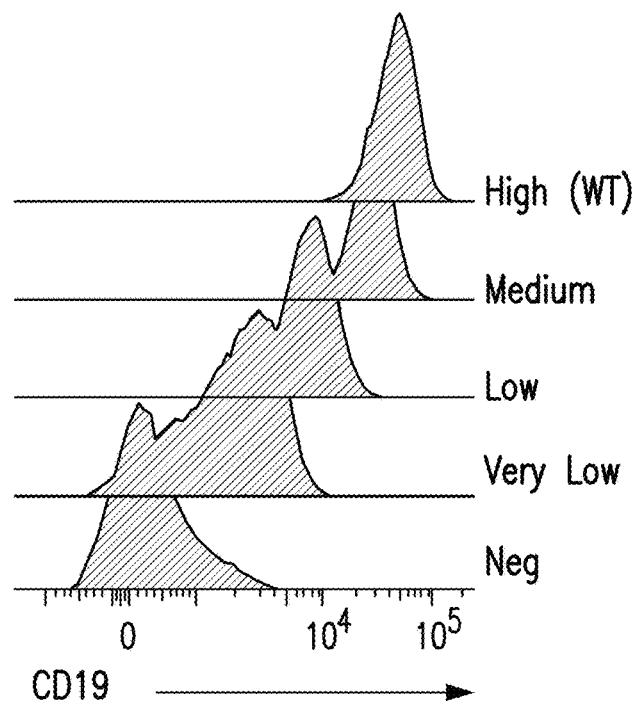
FIGS. 7A-7B depict HIT T cells outperform CAR T cells at killing target cells expressing low antigen levels. Nalm6 cell line (expressing firefly luciferase) was gene edited at the CD19 locus using CRISPR/Cas9, and clones expressing different CD19 levels were generated.
Figure 7B:
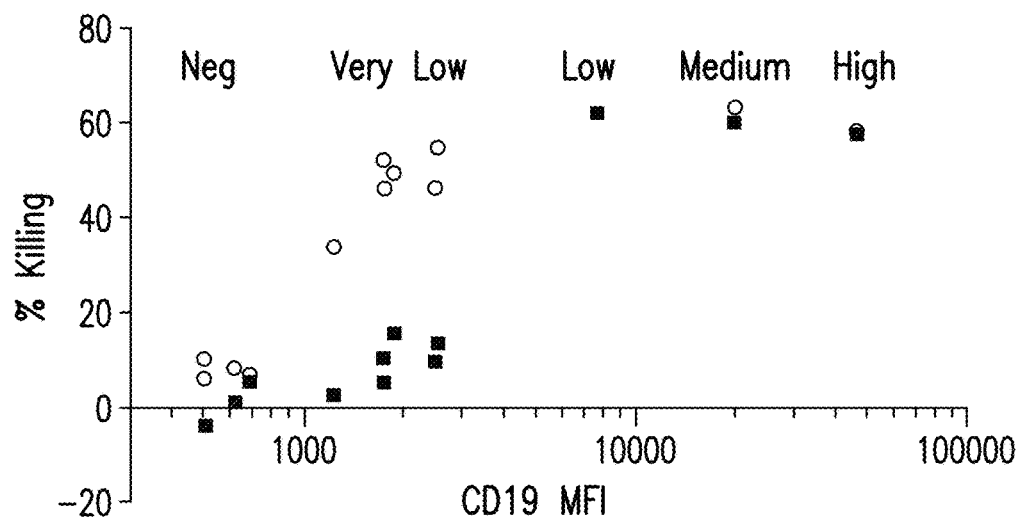
Figure 8A:
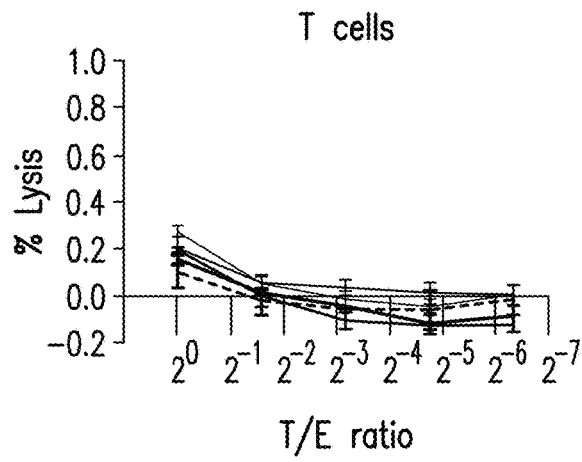
FIGS. 8A-8C depict HIT T cells outperform CAR T cells at killing target cells expressing low antigen levels. Cytotoxic activity using an 18 h bioluminescence assay, using NALM6 as targets cells expressing different CD19 levels (indicated at the right), which were incubated with untransduced T cells (FIG. 8A), CAR T cells (FIG. 8B), and HIT T cells (FIG. 8C) at different effector (E):target (T) ratios.
Figure 8B:
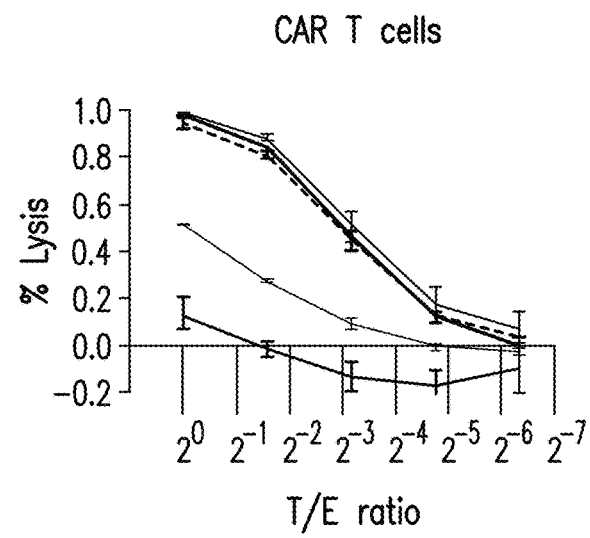
Figure 8C:
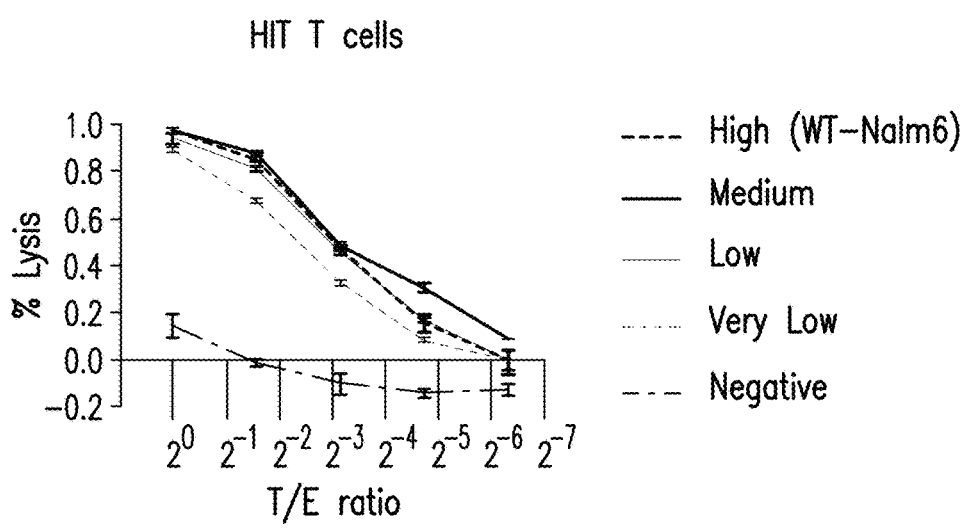

CRISPR/Cas9-targeted integration of the three receptors into the TRAC locus is shown in FIG. 1A. The engineered HIT-CAR targets CD19. Cell surface expression of HIT-CAR (i.e., HI-TCR) from TRAC locus is show in FIGS. 6B and 6C. Cytolytic effects and proliferation of HIT-CAR (i.e., HI-TCR or FvTCR) T cells are shown in FIGS. 7A,7B and 8A-8C. In particular, these data show that HIT T cells outperformed CAR-T cells at killing target cells expressing low antigen levels.

Furthermore, as shown in FIGS. 9A-9D the HI-TCR T cells were engineered to co-express costimulatory ligands. In this specific experiment, the day after targeting the HI-TCR to the TRAC locus, the T cells were transferred with retroviral SFG vectors coding for CD80, 41BBL or both. 5 days after expanding these cells ex vivo, 4e5 TRAC-CAR or TRAC-HI-TCR positive T cells were injected into NSG mice bearing NALM6 cells expressing very low level of CD19. The TRAC-HI-TCR T cells we either expressing CD80, 41BBL, both ligand or none. Bioluminescence was used to assess the tumor burden every week and follow the survival of the mice.

It was observed that the TRAC-CAR T cells were not able to control the tumor with very low levels of CD19 and all the mice were terminally ill by day 30. At this low dose, the HI-TCR T cells initially controlled the tumor burden, however the mice relapsed by day 10 and were terminally ill by day 40. The addition of costimulatory ligands to the HI-TCR T cells improved the anti-tumor activity with an optimal response when the HI-TCR T cells co-expressed CD80 and 4-1BBL. This improved activity resulted in a long-term control of NALM6 expressing very low levels of CD19.

Figure 10A:
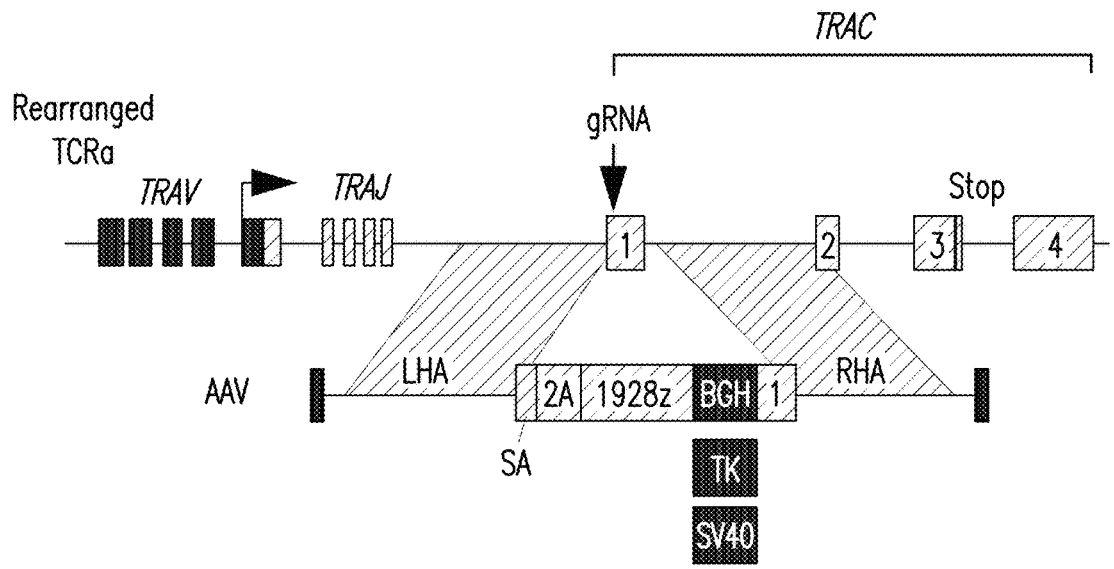
FIGS. 10A-10C depict that baseline TRAC-CAR expression can be controlled by distinct 3'UTR sequences without affecting cell surface replenishment kinetic after antigen encounter.
Figure 10B:
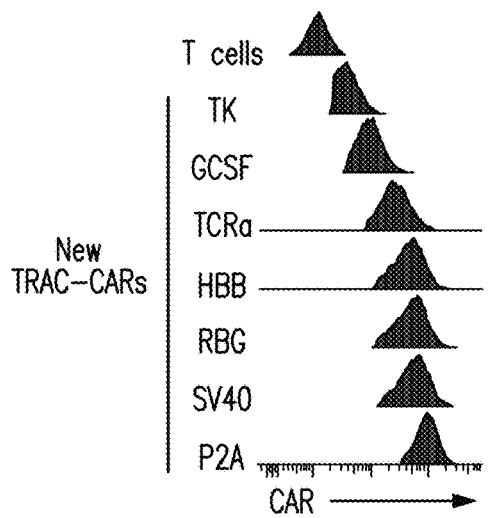
Figure 10C:
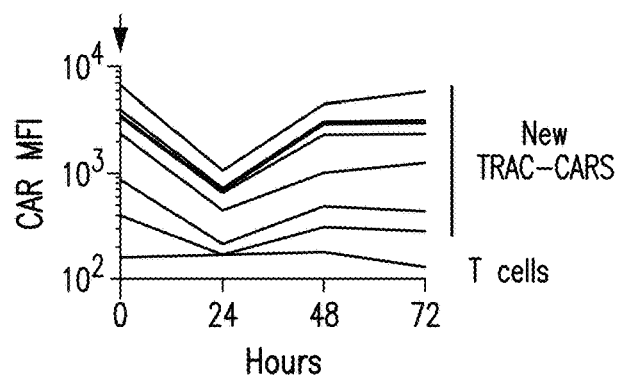

FIGS. 10A-10C further demonstrate that baseline TRAC-CAR expression can be controlled by distinct 3'UTR sequences without affecting cell surface replenishment kinetic after antigen encounter. The TRAC-CAR T cells were engineered the same way as previously described, so that the all the constructs were under the transcriptional control of the TRAC endogenous promoter. It was observed that by modifying the 3'UTR (that includes polyA signal), the baseline expression level were modulated (FIG. 10B). When these different TRAC-CAR T cells were cultivated on CD19 expressing tumor cells, a drop in the CAR cell surface expression followed by a replenishment was observed by flow cytometry (FIG. 10C). The different 3'UTR changed the baseline expression level but they retained the same replenishment kinetic and the final expression level was similar to the baseline.

Furthermore, a HI-TCR targeting CD70 and a HI-TCR targeting CD22 were also created. HI-TCR targeting an interested antigen can be created by sequencing an existing scFv or a Fab region of an existing antibody targeting the same antigen to obtain the extracellular antigen-binding domain.

Embodiments of the Presently Disclosed Subject Matter

From the foregoing description, it will be apparent that variations and modifications may be made to the presently disclosed subject matter to adopt it to various usages and conditions. Such embodiments are also within the scope of the following claims.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating a tumor cell in a subject, the method comprising administering to the subject an effective amount of immunoresponsive cells, wherein the immunoresponsive cell comprises a recombinant T cell receptor (TCR) that comprises:
   i) a first antigen-binding chain comprising an antigen-binding fragment of a heavy chain variable region ($V_H$) of an antibody; and
   ii) a second antigen-binding chain comprising an antigen-binding fragment of a light chain variable region ($V_L$) of the antibody;
   wherein the first and second antigen-binding chains each comprise a TRAC polypeptide or a TRBC polypeptide, and the first and the second antigen-binding chains bind to an antigen,
   wherein the tumor cell expresses the antigen on its surface at a density of less than about 10,000 molecules per cell.

2. A method of treating a tumor cell in a subject, the method comprising administering to the subject an effective amount of immunoresponsive cells, wherein the immunoresponsive cell comprises a recombinant T cell receptor (TCR) that comprises:
   i) a first antigen-binding chain comprising an antigen-binding fragment of a heavy chain variable region ($V_H$) of an antibody; and
   ii) a second antigen-binding chain comprising an antigen-binding fragment of a light chain variable region ($V_L$) of the antibody;
   wherein the first and second antigen-binding chains each comprise a TRAC polypeptide or a TRBC polypeptide, and the first and the second antigen-binding chains bind to an antigen with a dissociation constant ($K_D$) of about $1 \times 10^{-8}$ M or less, and the tumor cell expresses the antigen.

3. The method of claim 1, wherein at least one of the TRAC polypeptide and the TRBC polypeptide is endogenous.

4. The method of claim 1, wherein the immunoresponsive cell is a cell of lymphoid lineage or a pluripotent stem cell from which a cell of lymphoid lineage may be differentiated.

5. The method of claim 1, wherein the immunoresponsive cell is a B cell, a T cell, a Natural Killer (NK) cell, a pluripotent stem cell from which a lymphoid cell may be differentiated, or a combination thereof.

6. The method of claim 1, wherein the immunoresponsive cell is a T cell, optionally wherein the T cell is selected from the group consisting of a cytotoxic T lymphocyte (CTL), a regulatory T cell, and a Natural Killer T (NKT) cell.

7. The method of claim 2, wherein the tumor cell expresses the antigen on its surface at a density of less than about 10,000 molecules per cell.

8. The method of claim 1, wherein the antigen is selected from the group consisting of CD19, MUC16, MUC1, CAIX, CEA, CD8, CD7, CD10, CD20, CD22, CD30, CLL1, CD33, CD34, CD38, CD41, CD44, CD49f, CD56, CD74, CD133, CD138, EGP-2, EGP-40, EpCAM, erb-B2,3,4, FBP, Fetal acetylcholine receptor, folate receptor-a, GD2, GD3, HER- 2, hTERT, IL-13R-a2, K-light chain, KDR, LeY, L1 cell adhesion molecule, MAGE-A1, Mesothelin, ERBB2, MAGEA3, p53, MART1, GP100, Proteinase3 (PR1), Tyrosinase, Survivin, hTERT, EphA2, NKG2D ligands, NY-ESO-1, oncofetal antigen (h5T4), PSCA, PSMA, ROR1, TAG-72, VEGF-R2, WT-1, BCMA, CD123, CD44V6, NKCS1, EGF1R, EGFR-VIII, CD99, CD70, ADGRE2, CCR1, LILRB2, LILRB4, PRAME, and ERBB.

9. The method of claim 8, wherein antigen is selected from the group consisting of CD22, BCMA, CCR1, and CD70.

10. The method of claim 9, wherein the antigen is CD70.

11. The method of claim 1, wherein the recombinant TCR is expressed by a transgene that is integrated at an endogenous gene locus of the immunoresponsive cell.

12. The method of claim 11, wherein the endogenous gene locus is a CD3δ locus, a CD3ε locus, a CD247 locus, a B2M locus, a TRAC locus, a TRBC locus, a TRDC locus and/or a TRGC locus.

13. The method of claim 11, wherein the endogenous expression of a TCR comprising a native TCR α chain and/or a native TCR β chain is disrupted or abolished in the immunoresponsive cell, thereby preventing or eliminating mispairing between the recombinant TCR and a native TCR α chain and/or a native TCR β chain in the immunoresponsive cell.

14. The method of claim 11, wherein the endogenous gene locus is a first endogenous TCR locus, and a second endogenous TCR locus that is different from the first endogenous TCR locus is modified to eliminate the expression of an endogenous TCR chain encoded by the second endogenous TCR locus.

15. The method of claim 1, wherein the tumor cell is a cancer cell.

16. The method of claim 1, wherein the tumor cell is a relapsed tumor cell.

17. The method of claim 1, wherein the tumor cell is a solid tumor cell.

18. The method of claim 1, wherein the tumor cell is a hematologic malignancy cell.

19. The method of claim 1, wherein the tumor cell is a blood cancer cell.

20. The method of claim 1, wherein the tumor cell is selected from the group consisting of B cell leukemia cells, multiple myeloma cells, acute lymphoblastic leukemia (ALL) cells, chronic lymphocytic leukemia (CLL) cells, Hodgkin's lymphoma cells, non-Hodgkin's lymphoma cells, Acute myeloid leukemia (AML) cells, and adenocarcinoma cells.

21. A method of treating a tumor cell in a subject, the method comprising administering to the subject an effective amount of immunoresponsive cells, wherein the immunoresponsive cell comprises a recombinant T cell receptor (TCR) that comprises:
i) a first antigen-binding chain comprising an antigen-binding fragment of a heavy chain variable region ($V_H$) of an antibody; and
ii) a second antigen-binding chain comprising an antigen-binding fragment of a light chain variable region ($V_L$) of the antibody;
wherein the first and second antigen-binding chains each comprise a TRAC polypeptide or a TRBC polypeptide, and the first and the second antigen-binding chains bind to an antigen, and the tumor is associated with the antigen, and
wherein at least one of the TRAC polypeptide and the TRBC polypeptide is endogenous.

* * * * *

```
                        SEQUENCE LISTING

<160> NUMBER OF SEQ ID NOS: 48

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ala Phe Ser Ser
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Pro Gly Asp Gly Asp
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Thr Ile Ser Ser Val Val Asp Phe
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Ser Gln Asn Val Gly Thr Asn Val Ala
1               5                   10

<210> SEQ ID NO 5
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Thr Tyr Arg Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Tyr Asn Arg Tyr Pro Tyr Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr Val Ser Ser
            115                 120

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
```

```
                35                  40                  45
Tyr Ser Ala Thr Tyr Arg Asn Ser Gly Val Pro Asp Arg Phe Thr Gly
         50                  55                  60

Ser Gly Ser Gly Thr Asp Phe Thr Leu Thr Ile Thr Asn Val Gln Ser
 65                  70                  75                  80

Lys Asp Leu Ala Asp Tyr Phe Cys Gln Gln Tyr Asn Arg Tyr Pro Tyr
                 85                  90                  95

Thr Ser Gly Gly Gly Thr Lys Leu Glu Ile Lys Arg
            100                 105

<210> SEQ ID NO 9
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Leu Pro Val Thr Ala Leu Leu Leu Pro Leu Ala Leu Leu Leu
 1               5                  10                  15

His Ala Glu Val Lys Leu Gln Gln Ser Gly Ala Glu Leu Val Arg Pro
                 20                  25                  30

Gly Ser Ser Val Lys Ile Ser Cys Lys Ala Ser Gly Tyr Ala Phe Ser
            35                  40                  45

Ser Tyr Trp Met Asn Trp Val Lys Gln Arg Pro Gly Gln Gly Leu Glu
 50                  55                  60

Trp Ile Gly Gln Ile Tyr Pro Gly Asp Gly Asp Thr Asn Tyr Asn Gly
 65                  70                  75                  80

Lys Phe Lys Gly Gln Ala Thr Leu Thr Ala Asp Lys Ser Ser Ser Thr
                 85                  90                  95

Ala Tyr Met Gln Leu Ser Gly Leu Thr Ser Glu Asp Ser Ala Val Tyr
            100                 105                 110

Phe Cys Ala Arg Lys Thr Ile Ser Ser Val Val Asp Phe Tyr Phe Asp
        115                 120                 125

Tyr Trp Gly Gln Gly Thr Val Thr Val Ser Ser Gly Gly Gly Gly
    130                 135                 140

Ser Gly Gly Gly Ser Gly Gly Gly Gly Ser Asp Ile Glu Leu Thr
145                 150                 155                 160

Gln Ser Pro Lys Phe Met Ser Thr Ser Val Gly Asp Arg Val Ser Val
                165                 170                 175

Thr Cys Lys Ala Ser Gln Asn Val Gly Thr Asn Val Ala Trp Tyr Gln
            180                 185                 190

Gln Lys Pro Gly Gln Ser Pro Lys Pro Leu Ile Tyr Ser Ala Thr Tyr
        195                 200                 205

Arg Asn Ser Gly Val Pro Asp Arg Phe Thr Gly Ser Gly Ser Gly Thr
    210                 215                 220

Asp Phe Thr Leu Thr Ile Thr Asn Val Gln Ser Lys Asp Leu Ala Asp
225                 230                 235                 240

Tyr Phe Cys Gln Gln Tyr Asn Arg Tyr Pro Tyr Thr Ser Gly Gly Gly
                245                 250                 255

Thr Lys Leu Glu Ile Lys Arg
            260

<210> SEQ ID NO 10
<211> LENGTH: 789
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggctctcc cagtgactgc cctactgctt ccctagcgc ttctcctgca tgcagaggtg    60
aagctgcagc agtctggggc tgagctggtg aggcctgggt cctcagtgaa gatttcctgc   120
aaggcttctg gctatgcatt cagtagctac tggatgaact gggtgaagca gaggcctgga   180
cagggtcttg agtggattgg acagatttat cctggagatg gtgatactaa ctacaatgga   240
aagttcaagg gtcaagccac actgactgca gacaaatcct ccagcacagc ctacatgcag   300
ctcagcggcc taacatctga ggactctgcg gtctatttct gtgcaagaaa gaccattagt   360
tcggtagtag atttctactt tgactactgg ggccaaggga ccacggtcac cgtctcctca   420
ggtggaggtg gatcaggtgg aggtggatct ggtggaggtg gatctgacat tgagctcacc   480
cagtctccaa aattcatgtc cacatcagta ggagacaggg tcagcgtcac ctgcaaggcc   540
agtcagaatg tgggtactaa tgtagcctgg tatcaacaga aaccaggaca atctcctaaa   600
ccactgattt actcggcaac ctaccggaac agtggagtcc ctgatcgctt cacaggcagt   660
ggatctggga cagatttcac tctcaccatc actaacgtgc agtctaaaga cttggcagac   720
tatttctgtc aacaatataa caggtatccg tacacgtccg gagggggggac caagctggag   780
atcaaacgg                                                           789
```

<210> SEQ ID NO 11
<211> LENGTH: 272
<212> TYPE: PRT
<213> ORGANISM: Homo sapiens

<400> SEQUENCE: 11

```
Pro Glu Glu Pro Leu Val Val Lys Val Glu Glu Gly Asp Asn Ala Val
1               5                   10                  15

Leu Gln Cys Leu Lys Gly Thr Ser Asp Gly Pro Thr Gln Gln Leu Thr
            20                  25                  30

Trp Ser Arg Glu Ser Pro Leu Lys Pro Phe Leu Lys Leu Ser Leu Gly
        35                  40                  45

Leu Pro Gly Leu Gly Ile His Met Arg Pro Leu Ala Ile Trp Leu Phe
    50                  55                  60

Ile Phe Asn Val Ser Gln Gln Met Gly Gly Phe Tyr Leu Cys Gln Pro
65                  70                  75                  80

Gly Pro Pro Ser Glu Lys Ala Trp Gln Pro Gly Trp Thr Val Asn Val
                85                  90                  95

Glu Gly Ser Gly Glu Leu Phe Arg Trp Asn Val Ser Asp Leu Gly Gly
            100                 105                 110

Leu Gly Cys Gly Leu Lys Asn Arg Ser Ser Glu Gly Pro Ser Ser Pro
        115                 120                 125

Ser Gly Lys Leu Met Ser Pro Lys Leu Tyr Val Trp Ala Lys Asp Arg
    130                 135                 140

Pro Glu Ile Trp Glu Gly Glu Pro Pro Cys Leu Pro Pro Arg Asp Ser
145                 150                 155                 160

Leu Asn Gln Ser Leu Ser Gln Asp Leu Thr Met Ala Pro Gly Ser Thr
                165                 170                 175

Leu Trp Leu Ser Cys Gly Val Pro Pro Asp Ser Val Ser Arg Gly Pro
            180                 185                 190
```

```
Leu Ser Trp Thr His Val His Pro Lys Gly Pro Lys Ser Leu Leu Ser
            195                 200                 205
Leu Glu Leu Lys Asp Asp Arg Pro Ala Arg Asp Met Trp Val Met Glu
            210                 215                 220
Thr Gly Leu Leu Leu Pro Arg Ala Thr Ala Gln Asp Ala Gly Lys Tyr
225                 230                 235                 240
Tyr Cys His Arg Gly Asn Leu Thr Met Ser Phe His Leu Glu Ile Thr
                245                 250                 255
Ala Arg Pro Val Leu Trp His Trp Leu Leu Arg Thr Gly Gly Trp Lys
                260                 265                 270

<210> SEQ ID NO 12
<211> LENGTH: 20
<212> TYPE: PRT
<213> ORGANISM: Homo sapiens

<400> SEQUENCE: 12

Met Tyr Arg Met Gln Leu Leu Ser Cys Ile Ala Leu Ser Leu Ala Leu
1               5                   10                  15
Val Thr Asn Ser
            20

<210> SEQ ID NO 13
<211> LENGTH: 20
<212> TYPE: PRT
<213> ORGANISM: Mus sp.

<400> SEQUENCE: 13

Met Tyr Ser Met Gln Leu Ala Ser Cys Val Thr Leu Thr Leu Val Leu
1               5                   10                  15
Leu Val Asn Ser
            20

<210> SEQ ID NO 14
<211> LENGTH: 20
<212> TYPE: PRT
<213> ORGANISM: Homo sapiens

<400> SEQUENCE: 14

Met Glu Thr Pro Ala Gln Leu Leu Phe Leu Leu Leu Leu Trp Leu Pro
1               5                   10                  15
Asp Thr Thr Gly
            20

<210> SEQ ID NO 15
<211> LENGTH: 20
<212> TYPE: PRT
<213> ORGANISM: Mus sp.

<400> SEQUENCE: 15

Met Glu Thr Asp Thr Leu Leu Leu Trp Val Leu Leu Leu Trp Val Pro
1               5                   10                  15
Gly Ser Thr Gly
            20

<210> SEQ ID NO 16
<211> LENGTH: 21
<212> TYPE: PRT
<213> ORGANISM: Homo sapiens

<400> SEQUENCE: 16
```

```
Met Ala Leu Pro Val Thr Ala Leu Leu Pro Leu Ala Leu Leu Leu
1               5                   10                  15

His Ala Ala Arg Pro
                20
```

<210> SEQ ID NO 17
<211> LENGTH: 164
<212> TYPE: PRT
<213> ORGANISM: Homo sapiens

<400> SEQUENCE: 17

```
Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
                35                  40                  45

Leu Phe Leu Arg Val Lys Phe Ser Arg Ser Ala Asp Ala Pro Ala Tyr
            50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                    85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 18
<211> LENGTH: 112
<212> TYPE: PRT
<213> ORGANISM: Homo sapiens

<400> SEQUENCE: 18

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
            50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

<210> SEQ ID NO 19
<211> LENGTH: 336

<212> TYPE: DNA
<213> ORGANISM: Homo sapiens

<400> SEQUENCE: 19

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336
```

<210> SEQ ID NO 20
<211> LENGTH: 220
<212> TYPE: PRT
<213> ORGANISM: Homo sapiens

<400> SEQUENCE: 20

```
Met Leu Arg Leu Leu Leu Ala Leu Asn Leu Phe Pro Ser Ile Gln Val
  1               5                  10                  15

Thr Gly Asn Lys Ile Leu Val Lys Gln Ser Pro Met Leu Val Ala Tyr
             20                  25                  30

Asp Asn Ala Val Asn Leu Ser Cys Lys Tyr Ser Tyr Asn Leu Phe Ser
         35                  40                  45

Arg Glu Phe Arg Ala Ser Leu His Lys Gly Leu Asp Ser Ala Val Glu
     50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 21
<211> LENGTH: 41
<212> TYPE: PRT
<213> ORGANISM: Homo sapiens

<400> SEQUENCE: 21

```
Arg Ser Lys Arg Ser Arg Leu Leu His Ser Asp Tyr Met Asn Met Thr
  1               5                  10                  15

Pro Arg Arg Pro Gly Pro Thr Arg Lys His Tyr Gln Pro Tyr Ala Pro
```

```
              20                  25                  30

Pro Arg Asp Phe Ala Ala Tyr Arg Ser
         35                  40

<210> SEQ ID NO 22
<211> LENGTH: 123
<212> TYPE: DNA
<213> ORGANISM: Homo sapiens

<400> SEQUENCE: 22
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 23
<211> LENGTH: 255
<212> TYPE: PRT
<213> ORGANISM: Homo sapiens

<400> SEQUENCE: 23
```

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

```
<210> SEQ ID NO 24
<211> LENGTH: 42
<212> TYPE: PRT
```

<213> ORGANISM: Homo sapiens

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 25
<211> LENGTH: 277
<212> TYPE: PRT
<213> ORGANISM: Homo sapiens

<400> SEQUENCE: 25

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 26
<211> LENGTH: 199
<212> TYPE: PRT

<213> ORGANISM: Homo sapiens

<400> SEQUENCE: 26

| Met | Lys | Ser | Gly | Leu | Trp | Tyr | Phe | Phe | Leu | Phe | Cys | Leu | Arg | Ile | Lys |
| 1 | | | | 5 | | | | | 10 | | | | | 15 | |

| Val | Leu | Thr | Gly | Glu | Ile | Asn | Gly | Ser | Ala | Asn | Tyr | Glu | Met | Phe | Ile |
| | | | 20 | | | | | 25 | | | | | 30 | | |

| Phe | His | Asn | Gly | Gly | Val | Gln | Ile | Leu | Cys | Lys | Tyr | Pro | Asp | Ile | Val |
| | | 35 | | | | | 40 | | | | | 45 | | | |

| Gln | Gln | Phe | Lys | Met | Gln | Leu | Leu | Lys | Gly | Gly | Gln | Ile | Leu | Cys | Asp |
| | 50 | | | | | 55 | | | | | 60 | | | | |

| Leu | Thr | Lys | Thr | Lys | Gly | Ser | Gly | Asn | Thr | Val | Ser | Ile | Lys | Ser | Leu |
| 65 | | | | | 70 | | | | | 75 | | | | | 80 |

| Lys | Phe | Cys | His | Ser | Gln | Leu | Ser | Asn | Asn | Ser | Val | Ser | Phe | Phe | Leu |
| | | | | 85 | | | | | 90 | | | | | 95 | |

| Tyr | Asn | Leu | Asp | His | Ser | His | Ala | Asn | Tyr | Tyr | Phe | Cys | Asn | Leu | Ser |
| | | | 100 | | | | 105 | | | | | 110 | | | |

| Ile | Phe | Asp | Pro | Pro | Phe | Lys | Val | Thr | Leu | Thr | Gly | Gly | Tyr | Leu |
| | | 115 | | | | 120 | | | | | 125 | | | |

| His | Ile | Tyr | Glu | Ser | Gln | Leu | Cys | Cys | Gln | Leu | Lys | Phe | Trp | Leu | Pro |
| | 130 | | | | | 135 | | | | | 140 | | | | |

| Ile | Gly | Cys | Ala | Ala | Phe | Val | Val | Cys | Ile | Leu | Gly | Cys | Ile | Leu |
| 145 | | | | | 150 | | | | | 155 | | | | | 160 |

| Ile | Cys | Trp | Leu | Thr | Lys | Lys | Lys | Tyr | Ser | Ser | Ser | Val | His | Asp | Pro |
| | | | | 165 | | | | | 170 | | | | | 175 | |

| Asn | Gly | Glu | Tyr | Met | Phe | Met | Arg | Ala | Val | Asn | Thr | Ala | Lys | Lys | Ser |
| | | | 180 | | | | | 185 | | | | | 190 | | |

| Arg | Leu | Thr | Asp | Val | Thr | Leu |
| | | | | 195 | | |

<210> SEQ ID NO 27
<211> LENGTH: 126
<212> TYPE: DNA
<213> ORGANISM: Homo sapiens

<400> SEQUENCE: 27

```
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126
```

<210> SEQ ID NO 28
<211> LENGTH: 18
<212> TYPE: PRT
<213> ORGANISM: Homo sapiens

<400> SEQUENCE: 28

| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |

| His | Ala |
| | |

<210> SEQ ID NO 29
<211> LENGTH: 4627
<212> TYPE: DNA
<213> ORGANISM: Homo sapiens

<400> SEQUENCE: 29

```
atatccagaa ccctgaccct gccgtgtacc agctgagaga ctctaaatcc agtgacaagt      60
```

```
ctgtctgcct attcaccgat tttgattctc aaacaaatgt gtcacaaagt aaggattctg    120
atgtgtatat cacagacaaa actgtgctag acatgaggtc tatggacttc aagagcaaca    180
gtgctgtggc ctggagcaac aaatctgact ttgcatgtgc aaacgccttc aacaacagca    240
ttattccaga agacaccttc ttccccagcc caggtaaggg cagcttttgg gccttcgcag    300
gctgtttcct tgcttcagga atggccaggt tctgcccaga gctctggtca atgatgtcta    360
aaactcctct gattggtggt ctcggcctta tccattgcca ccaaaaccct cttttttacta   420 agaaacagtg agccttgttc tggcagtcca gagaatgaca cgggaaaaaa gcagatgaag    480
agaaggtggc aggagagggc acgtggccca gcctcagtct ctccaactga gttcctgcct    540
gcctgccttt gctcagactg tttgcccctt actgctcttc taggcctcat tctaagcccc    600
ttctccaagt tgcctctcct tatttctccc tgtctgccaa aaaatctttc ccagctcact    660
aagtcagtct cacgcagtca ctcattaacc caccaatcac tgattgtgcc ggcacatgaa    720
tgcaccaggt gttgaagtgg aggaattaaa aagtcagatg aggggtgtgc ccagaggaag    780
caccattcta gttgggggag cccatctgtc agctgggaaa agtccaaata acttcagatt    840
ggaatgtgtt ttaactcagg gttgagaaaa cagctacctt caggacaaaa gtcagggaag    900
ggctctctga agaaatgcta cttgaagata ccagccctac caagggcagg gagaggaccc    960
tatagaggcc tgggacagga gctcaatgag aaaggagaag agcagcaggc atgagttgaa   1020
tgaaggaggc agggccgggt cacagggcct tctaggccat gagagggtag acagtattct   1080
aaggacgcca gaaagctgtt gatcggcttc aagcagggga gggacaccta atttgctttt   1140
cttttttttt ttttttttt tttttttttt tgagatggag ttttgctctt gttgcccagg    1200
ctggagtgca atggtgcatc ttggctcact gcaacctccg cctcccaggt tcaagtgatt   1260
ctcctgcctc agcctcccga gtagctgaga ttacaggcac ccgccaccat gcctggctaa   1320 tttttttgtat ttttagtaga cagggtttt cactatgttg gccaggctgg tctcgaactc    1380
ctgacctcag gtgatccacc cgcttcagcc tcccaaagtg ctgggattac aggcgtgagc   1440
caccacaccc ggcctgcttt tcttaaagat caatctgagt gctgtacgga gagtgggttg    1500
taagccaaga gtagaagcag aaagggagca gttgcagcag agagatgatg gaggcctggg   1560
cagggtggtg gcagggaggt aaccaacacc attcaggttt caaaggtaga accatgcagg   1620
gatgagaaag caaagagggg atcaaggaag gcagctggat tttggcctga gcagctgagt   1680
caatgatagt gccgtttact aagaagaaac caaggaaaaa atttggggtg cagggatcaa   1740 aacttttttgg aacatatgaa agtacgtgtt tatactcttt atggcccttg tcactatgta    1800
tgcctcgctg cctccattgg actctagaat gaagccaggc aagagcaggg tctatgtgtg   1860
atggcacatg tggccaggt catgcaacat gtactttgta caaacagtgt atattgagta    1920
aatagaaatg gtgtccagga gccgaggtat cggtcctgcc agggccaggg gctctcccta   1980
gcaggtgctc atatgctgta agttccctcc agatctctcc acaaggaggc atggaaaggc   2040
tgtagttgtt cacctgccca agaactagga ggtctggggt gggagagtca gcctgctctg   2100
gatgctgaaa gaatgtctgt ttttccttttt agaaagttcc tgtgatgtca agctggtcga   2160
gaaaagcttt gaaacaggta agacaggggt ctagcctggg tttgcacagg attgcggaag   2220
tgatgaaccc gcaataaccc tgcctggatg agggagtggg aagaaattag tagatgtggg   2280
aatgaatgat gaggaatgga aacagcggtt caagacctgc ccagagctgg gtggggtctc   2340
tcctgaatcc ctctcaccat ctctgacttt ccattctaag cactttgagg atgagtttct   2400
```

```
agcttcaata gaccaaggac tctctcctag gcctctgtat tcctttcaac agctccactg    2460
tcaagagagc cagagagagc ttctgggtgg cccagctgtg aaatttctga gtcccttagg    2520
gatagcccta acgaaccag atcatcctga ggacagccaa gaggttttgc cttctttcaa     2580
gacaagcaac agtactcaca taggctgtgg gcaatggtcc tgtctctcaa gaatcccctg    2640
ccactcctca cacccaccct gggcccatat tcatttccat ttgagttgtt cttattgagt    2700
catccttcct gtggtagcgg aactcactaa ggggcccatc tggacccgag gtattgtgat    2760
gataaattct gagcacctac cccatcccca aagggctca gaaataaaat aagagccaag     2820
tctagtcggt gtttcctgtc ttgaaacaca atactgttgg ccctggaaga atgcacagaa    2880
tctgtttgta aggggatatg cacagaagct gcaagggaca ggaggtgcag gagctgcagg    2940
cctcccccac ccagcctgct ctgccttggg aaaaccgtg ggtgtgtcct gcaggccatg     3000
caggcctggg acatgcaagc ccataaccgc tgtggcctct tggttttaca gatacgaacc    3060
taaactttca aaacctgtca gtgattgggt tccgaatcct cctcctgaaa gtggccgggt    3120
ttaatctgct catgacgctg cggctgtggt ccagctgagg tgaggggcct tgaagctggg    3180 agtgggggttt agggacgcgg gtctctgggt gcatcctaag ctctgagagc aaacctccct   3240
gcagggtctt gcttttaagt ccaaagcctg agcccaccaa actctcctac ttcttcctgt    3300
tacaaattcc tcttgtgcaa taataatggc ctgaaacgct gtaaaatatc ctcatttcag    3360
ccgcctcagt tgcacttctc ccctatgagg taggaagaac agttgtttag aaacgaagaa    3420
actgaggccc cacagctaat gagtggagga agagagacac ttgtgtacac cacatgcctt    3480
gtgttgtact tctctcaccg tgtaacctcc tcatgtcctc tctccccagt acggctctct    3540
tagctcagta gaaagaagac attacactca tattcacccc caatcctggc tagagtctcc    3600
gcaccctcct cccccagggt ccccagtcgt cttgctgaca actgcatcct gttccatcac    3660
catcaaaaaa aaactccagg ctgggtgcgg gggctcacac ctgtaatccc agcactttgg    3720
gaggcagagg caggaggagc acaggagctg gagaccagcc tgggcaacac agggagaccc    3780
cgcctctaca aaaagtgaaa aaattaacca ggtgtggtgc tgcacacctg tagtcccagc    3840
tacttaagag gctgagatgg gaggatcgct tgagccctgg aatgttgagg ctacaatgag    3900
ctgtgattgc gtcactgcac tccagcctgg aagacaaagc aagatcctgt ctcaaataat    3960
aaaaaaaata agaactccag ggtacatttg ctcctagaac tctaccacat agccccaaac    4020
agagccatca ccatcacatc cctaacagtc ctgggtcttc tcagtgtcc agcctgactt     4080 ctgttcttcc tcattccaga tctgcaagat tgtaagacag cctgtgctcc ctcgctcctt    4140
cctctgcatt gccctcttc tccctctcca aacagaggga actctcctac ccccaaggag     4200
gtgaaagctg ctaccacctc tgtgcccccc cggcaatgcc accaactgga tcctacccga    4260
atttatgatt aagattgctg aagagctgcc aaacactgct gccaccccct ctgttccctt    4320
attgctgctt gtcactgcct gacattcacg gcagaggcaa ggctgctgca gcctcccctg    4380
gctgtgcaca ttccctcctg ctcccagag actgcctccg ccatcccaca gatgatggat    4440
cttcagtggg ttctcttggg ctctaggtcc tgcagaatgt tgtgaggggt ttattttttt    4500
ttaatagtgt tcataaagaa atacatagta ttcttcttct caagacgtgg ggggaaatta   4560
tctcattatc gaggccctgc tatgctgtgt atctgggcgt gttgtatgtc ctgctgccga    4620
tgccttc                                                             4627
```

<210> SEQ ID NO 30
<211> LENGTH: 1448

<212> TYPE: DNA
<213> ORGANISM: Homo sapiens

<400> SEQUENCE: 30

```
aggacctgaa caaggtgttc cacccgagg tcgctgtgtt tgagccatca gaagcagaga      60
tctcccacac ccaaaaggcc acactggtgt gcctggccac aggcttcttc cccgaccacg    120
tggagctgag ctggtgggtg aatgggaagg aggtgcacag tggggtcagc acagacccgc    180
agccccctcaa ggagcagccc gccctcaatg actccagata ctgcctgagc agccgcctga   240
gggtctcggc caccttctgg cagaaccccc gcaaccactt ccgctgtcaa gtccagttct    300
acgggctctc ggagaatgac gagtggaccc aggatagggc caaacccgtc acccagatcg    360
tcagcgccga ggcctggggt agagcaggtg agtgggcct ggggagatgc ctggaggaga     420
ttaggtgaga ccagctacca gggaaaatgg aaagatccag gtagcagaca agactagatc    480
caaaagaaa ggaaccagcg cacaccatga aggagaattg ggcacctgtg gttcattctt     540
ctcccagatt ctcagcccaa cagagccaag cagctgggtc ccctttctat gtggcctgtg   600
taactctcat ctgggtggtg cccccatcc ccctcagtgc tgccacatgc catggattgc     660
aaggacaatg tggctgacat ctgcatggca gaagaaagga ggtgctgggc tgtcagagga    720
agctggtctg ggcctgggag tctgtgccaa ctgcaaatct gactttactt ttaattgcct   780
atgaaaataa ggtctctcat ttattttcct ctccctgctt tctttcagac tgtggcttta   840
cctcgggtaa gtaagccctt cctttttcctc tccctctctc atggttcttg acctagaacc   900
aaggcatgaa gaactcacag acactggagg gtggagggtg ggagagacca gagctacctg   960
tgcacaggta cccacctgtc cttcctccgt gccaacagtg tcctaccagc aagggggtcct 1020
gtctgccacc atcctctatg agatcctgct agggaaggcc accctgtatg ctgtgctggt 1080
cagcgccctt gtgttgatgg ccatggtaag caggagggca ggatggggcc agcaggctgg 1140
aggtgacaca ctgacaccaa gcacccagaa gtatagagtc cctgccagga ttggagctgg 1200
gcagtaggga gggaagagat ttcattcagg tgcctcagaa gataacttgc acctctgtag 1260
gatcacagtg gaagggtcat gctgggaagg agaagctgga gtcaccagaa aacccaatgg 1320
atgttgtgat gagccttact atttgtgtgg tcaatgggcc ctactacttt ctctcaatcc 1380
tcacaactcc tggctcttaa taacccccaa aactttctct tctgcaggtc aagagaaagg 1440
atttctga                                                              1448
```

<210> SEQ ID NO 31
<211> LENGTH: 1489
<212> TYPE: DNA
<213> ORGANISM: Homo sapiens

<400> SEQUENCE: 31

```
aggacctgaa aaacgtgttc cacccgagg tcgctgtgtt tgagccatca gaagcagaga     60
tctcccacac ccaaaaggcc acactggtat gcctggccac aggcttctac cccgaccacg   120
tggagctgag ctggtgggtg aatgggaagg aggtgcacag tggggtcagc acagacccgc   180
agccccctcaa ggagcagccc gccctcaatg actccagata ctgcctgagc agccgcctga  240
gggtctcggc caccttctgg cagaaccccc gcaaccactt ccgctgtcaa gtccagttct   300
acgggctctc ggagaatgac gagtggaccc aggatagggc caaacccgtc acccagatcg   360
tcagcgccga ggcctggggt agagcaggtg agtgggcct ggggagatgc ctggaggaga    420
ttaggtgaga ccagctacca gggaaaatgg aaagatccag gtagcggaca agactagatc   480
```

| | | | | | |
|---|---|---|---|---|---|
| cagaagaaag | ccagagtgga | caaggtggga | tgatcaaggt | tcacagggtc | agcaaagcac | 540 |
| ggtgtgcact | tcccccacca | agaagcatag | aggctgaatg | gagcacctca | agctcattct | 600 |
| tccttcagat | cctgacacct | tagagctaag | ctttcaagtc | tccctgagga | ccagccatac | 660 |
| agctcagcat | ctgagtggtg | tgcatcccat | tctcttctgg | ggtcctggtt | tcctaagatc | 720 |
| atagtgacca | cttcgctggc | actggagcag | catgagggag | acagaaccag | ggctatcaaa | 780 |
| ggaggctgac | tttgtactat | ctgatatgca | tgtgtttgtg | gcctgtgagt | ctgtgatgta | 840 |
| aggctcaatg | tccttacaaa | gcagcattct | ctcatccatt | tttcttcccc | tgttttcttt | 900 |
| cagactgtgg | cttcacctcc | ggtaagtgag | tctctccttt | ttctctctat | ctttcgccgt | 960 |
| ctctgctctc | gaaccagggc | atggagaatc | cacggacaca | ggggcgtgag | ggaggccaga | 1020 |
| gccacctgtg | cacaggtgcc | tacatgctct | gttcttgtca | acagagtctt | accagcaagg | 1080 |
| ggtcctgtct | gccaccatcc | tctatgagat | cttgctaggg | aaggccacct | tgtatgccgt | 1140 |
| gctggtcagt | gccctcgtgc | tgatggccat | ggtaaggagg | agggtgggat | agggcagatg | 1200 |
| atggggggcag | gggatggaac | atcacacatg | ggcataaagg | aatctcagag | ccagagcaca | 1260 |
| gcctaatata | tcctatcacc | tcaatgaaac | cataatgaag | ccagactggg | gagaaaatgc | 1320 |
| agggaatatc | acagaatgca | tcatgggagg | atggagacaa | ccagcgagcc | ctactcaaat | 1380 |
| taggcctcag | agcccgcctc | ccctgcccta | ctcctgctgt | gccatagccc | ctgaaaccct | 1440 |
| gaaaatgttc | tctcttccac | aggtcaagag | aaaggattcc | agaggctag | | 1489 |

<210> SEQ ID NO 32
<211> LENGTH: 5591
<212> TYPE: DNA
<213> ORGANISM: Homo sapiens

<400> SEQUENCE: 32

| | | | | | |
|---|---|---|---|---|---|
| ataaacaact | tgatgcagat | gtttccccca | agcccactat | ttttcttcct | tcaattgctg | 60 |
| aaacaaagct | ccagaaggct | ggaacatacc | tttgtcttct | tgagaaattt | ttccctgatg | 120 |
| ttattaagat | acattggcaa | gaaaagaaga | gcaacacgat | tctgggatcc | caggagggga | 180 |
| acaccatgaa | gactaacgac | acatacatga | aatttagctg | gttaacggtg | ccagaaaagt | 240 |
| cactggacaa | agaacacaga | tgtatcgtca | gacatgagaa | taataaaaac | ggagttgatc | 300 |
| aagaaattat | ctttcctcca | ataaagacag | gtatgtgttt | acgcatatca | tctgtcagaa | 360 |
| cacttctttg | aaagtgaatg | ctgcattttt | tcctttcagt | attaatgaaa | acaaacata | 420 |
| aatctttctt | aaatattgtt | acatttaatg | gtagcataaa | tgccctgcta | cttttctata | 480 |
| gaattaaaat | ggtataggtt | ttggagaaaa | caaaattgaa | aaagttactg | aaggtttgtc | 540 |
| agcctcagct | ccattatcca | aaataagaaa | gtcacgtgct | ggttttttagg | gttgttagat | 600 |
| ggattaaaga | acaacatac | acagaagcat | ctagcaacgt | gacacgtggt | aaacgctcaa | 660 |
| aaagtgttct | cccttctttt | gatgacttta | cttgatcagg | aaataacata | tatatgtctt | 720 |
| tcaggaatgt | tctgcccaag | caggagagtc | actcacctca | atcttgctac | ccacaaagtt | 780 |
| taacctaaaa | acaacgggtt | cattgttgac | aaaatgatgt | ttatctgttg | ttgacagaat | 840 |
| gatgtttatc | taaaaacagt | tccaattttc | tatttccttt | gctgagacac | aaaggggagg | 900 |
| caaatgtgca | agcttgagg | gtagtcttac | cactgtgctt | aagtgttctg | attttttctag | 960 |
| tgatcagggc | aaaataaaaa | gtatagtaag | ttccaaggca | gtgaatatta | tacaggagag | 1020 |
| aagttacagt | tttataatgt | gttttccttt | acactaaatt | ctaaaagtaa | aaagtcttt | 1080 |
| ttttttttg | acagagtttc | actcttgttg | cccaagcagg | tgtgctatgg | tatgatctca | 1140 |

```
gctcactgca acctccacct cccgggttca agtgattctc ttacttcagc ctcccgacag    1200
gctgggattg caggcgcctg ccaccacacc tggctaattt ttgtgttttt agtagagatg    1260
gggtttcacc atgttggcca ggctggtctc aaattcctga cctcaagtga tccatccacc    1320
tcggcctcca agtgctggga ttatgggcgt cagccactgt gcccagccta aaagtaaaat    1380
gtctttcatg agcttcccaa ggcagctacg ttaaggagga cacttctctt aatgtcattc    1440
tacagtagat ttctaatgct ctttcttgga agtttgtttt tctgagaaaa gctaaaaata    1500
taacatggaa gtgatcatat tatataatca atgaagtgct tttcaaggag ataaaactaa    1560
tctggtccac acttgcaacc aaccttgatt gagagagaga gagaactcag gatacacttg    1620
aagattttat tatggggaac agttacttta ttcttttttac ctcaatcaat gcatggaaat    1680
aagtgatagt cattttcatt tatctttttaa taaatgaagt caccatgagg aaaataaaaa    1740
gacattgaaa acccattaaa gtcagccctt aaagatattt ggacatgcag acttgataac    1800
taacgtttgc attcttgaga cttacccaaa acccatacct caagtccaag ttttttagaat    1860 tcatgaaata aagatctcag tgagtgcata aaattgcgca ccagaatcat atccgtatag    1920
acaagaacac atctactaga aaataataaa accaacacac caatgcaact gtgttttctt    1980
ctgttttaaa gtatgttgtc tttgtatgca tgtttgcttc ttcctttttt ttttttaacat    2040 cacagataaa ttcaactctc acctcaggtt ttattgagag aactgtcaat gtgacttggc    2100
ctctgtcttt ctagtcccag aaagaattgc actgaaatct gagctcctgt aataaaaaca    2160
accatttgct gagagtaatt aacatactga aagagatttt cttagagtac acaatggtga    2220
cattatattg cctctttata aataactttc tatctatttc tgtggattat tcctacaaag    2280 tactttttcat atgtccaatt tctttttcttc ccctacaact actgtctgaa tactggctct    2340
gctatttgct gatatgattc tcggcaagtt gcctgcactt ttttaaacttt atttcctcat    2400 tcagaacatg gggccataca taatacaact cacttcagtg ttattgggga attaaacaaa    2460
aaatgcatgg gaagcattta acatagtgcc tgacacaata atgagtactc agtagatgtt    2520
agctttattt aatattgttg ttgttatgtc cagaaacact ataccctccag aaaatcatgg    2580 gtacttgctg gggacattgg ggatatgcat gatttggaaa agaatgactg ctttttttgc    2640
ttagatgaga aatttttcta agccagactc cttcaaatat gtaagattct gttgtggatt    2700
caaggactga aagaattctt ggccgagtgt ggtggcttat ccctgtaatc ccagcatttt    2760
gtgaggacaa ggcaggaaga ttgcttgagt ccaggagttt gaaaccagcc tgcgcaacat    2820
ggcgaaaccc tgtctctaca aaaaatacaa acattagctc ggagtgagtg ctgacatgtg    2880
cctgtactcc cagctactca gaaggctgag atgggaggat ctcatgagcc tggggagttt    2940
gaggcttcag tgagccgtga tgacaccgta ctatactcca ctccagcctg ggtgacagtg    3000
agaccctgcc tcaaaaaaca aacaaacaaa caaacaaaac aaaattaatc ttttttgctga    3060 tgtcatgtca gcagtgtgtg ttgaaggctg taaagcagcc atttgttcag tttatttttc    3120
cattgaacaa gtatttatca aaaacatact ttgtggcagt cactatgcta ggagctatga    3180
atacagaagg aaaagtaaat gctcttggat actacactcc agttgtgata aaaagaaaa    3240 aatgtattct tcaccaactt caacatcttg atgtgcaaaa acataataca tgaattagat    3300
ctacctaatt acacagaatt agaccaattg tttctggaat tgtgggctca tattttttaat    3360 aactgtcctc ctgcctctct gtcgacaggt tttataaata ttcatttaat tacacacaca    3420
cacacgaaca attgactagt acttgctctc attcttctag atgtcatcac aatggatccc    3480
```

```
aaagacaatt gttcaaaaga tgcaaatggt aagcttttgt gttttccct tcctcctgat    3540
cattttgttt tgaacttctc tggcttgaaa aatcagggaa tggattttgc taggttggat    3600
gctgcagaat ggacctagtg atattttaaa ttagtccctc attttctagg agttgtatta    3660
acaaacctaa ctactgcttt ggggtatgag atgactgtaa attagagagg gtacagtggt    3720
atagtgatat gcttttaatt atttcaaaaa aaagatttta ttcattcatg tgtcttttt    3780
ctttttcttt tctttttttt tttttttgg acagagtctt gctctgtcac ccaggctgga    3840
gtgcggtggc agtatctcag ctcaccacaa cctccgcctc ccggcttcaa gtgattctcc    3900
tgcctcagct tctcgagtag ctgggactac aggcgcgtgc caccatgccc ggctaatttt    3960
tgtatttta gtagagttgg ggtttcacca tgttggccag gatggcctcg aatttgtgac    4020
ctcgtgatct gcccctcgc cctcccgaac tgttgggatt acaggcgtga gtcactgtgc    4080
ccggcctcct gtcctgtctt tgtttaatg actgggaaaa acatgatacc atgttgcttc    4140
tcgagttgtt ttgttttagt ctttggtctt tgctagtagc taataacacg aactagtgtt    4200
tatcaagtgc tttttacaca gaagggcttg ggctgtgttc tgcattttct tgtttaaccc    4260
tcttaaaact cctataaaat ggtacatatt tttctcccaa tttacagtcc ctttaaagca    4320
aataattata aaaatcccta tacatgtcac acagctagat ctgggatttc aaatcaggcc    4380
atcaaacaaa gagtttatgt acttagtaag ttttctgttc tttttctaca atagagtcag    4440
atagcaagaa attaccaagc caggaacctg aaacaaaacg gacatcatgt ggggctgggt    4500
gggtgcatgg gctttgcaga ctggactttc actccagctc ttttaatgat taggtgtaag    4560
tgacctacat tttgtgagca acagttttct catcagccaa caagaataa ttacaccaga    4620
ttcacagtta ttgaagagat aaaggcatga atgtgagatg tctggcatag gcatctcat    4680
ttagcagaca cagaatgagt acttgtttct ggctttttct ctctacatat gcacaaagaa    4740
tgcgactaga agcatgggct ctagccctgc tcaactttcc tctatttcca ataccaaggg    4800
gctctgactt aggctgccac accaggcaag gagggcagta ccacctcact tgaccaaggg    4860
cagggagtca cggacacatc acttcttgag atccttttcc acaccaagga ctgatgtttc    4920
tggaattctc actttatgaa gacaaaacat ataaatggaa attttctcag gtagagactc    4980
actcttgtag ctcattgagt aggcactagt ggtccacccc cactgtcttt acttattcct    5040
tgacatcaca tatctcttgc aaaacctcaa ataatattaa atgcaatcac ccaataatag    5100
catagccata attagaggca tttaggaaag acaggtgagt gtgccacaac tacctaacac    5160
atcagcaaat ctggattaac cactttcttt gattttccac aatgcaacct tacttttaa    5220
tagttgggaa tgttctaagt gaatttagca gaggttgtta atcaacttga aagctgaatt    5280
ctgacttgtc tgactcttgg tggtgctggt agcagtagat gtttactttt aggttttggt    5340
ggtggtggaa tatcacttca acgtaaatca tcagaaataa gtatttgtga acccctctcg    5400
cattaatgta tcttattctg taaaaagaac atgtgcaatt tctcttagat acactactgc    5460
tgcagctcac aaacacctct gcatattaca tgtacctcct cctgctcctc aagagtgtgg    5520
tctatttgc catcatcacc tgctgtctgc ttagaagaac ggctttctgc tgcaatggag    5580
agaaatcata a                                                         5591
```

<210> SEQ ID NO 33
<211> LENGTH: 9549
<212> TYPE: DNA
<213> ORGANISM: Homo sapiens

<400> SEQUENCE: 33

```
ataaacaact tgatgcagat gtttccccca agcccactat ttttcttcct tcgattgctg      60
aaacaaaact ccagaaggct ggaacatacc tttgtcttct tgagaaattt ttcccagata     120
ttattaagat acattggcaa gaaaagaaga gcaacacgat tctgggatcc caggagggga     180
acaccatgaa gactaacgac acatacatga aatttagctg gttaacggtg ccagaagagt     240
cactggacaa agaacacaga tgtatcgtca gacatgagaa taataaaaac ggaattgatc     300
aagaaattat ctttcctcca ataaagacag gtatgtgttt acacatatca tctgtcagaa     360
cacttctttg aaagtgaatg ctgcattttt tcctttcagt attaatgaaa aacataaatc     420
tttcttaaaa attgttacat ttaatggtag cgtaaatgcc ctgctacttt tctatagaat     480
taaaatggta taggttttgg agaaaacaaa attgaaaaag ttgctgaagg tttgtcagcc     540
tcagctccat tatccaaaat aagaaagtca cgtgctggtt tttagggttg ttagatggat     600
taaagaaaca acatacacag aagcatctag caacgtgaca cgtggtaaac gctcaaaaag     660
tgttctccct tctttgatg actttacttg atcaggaaat aacatatata tgtctttcag     720
gaatgttctg cccaagcagg agagtcactc acctcaatct tgctacccac aaagtttaac     780
ctaaaaacaa cgggttcatt gttgacaaaa taatgtttat ctgaagataa ctgtagatca     840
tatttatctg tagataatgt ttatctgtgg agtgtggctc tacaaaacat agaatagtct     900
tggtcactgc agttttatag aggccttggg ttttcagag tttcatttta tatatccacca     960 taaagtaaca tttcataatt acaggttggt aaggcttaca tgtacaaaca ttcttccatt    1020
ttccataata aatgcatttc ctgccattgg tgaatgcagc tcaataaaca tttattgtac    1080
aattatgaca cgccaggctt agtggaaatg tggatgaaca gacaaggatg agttactgtc    1140
ctaaggatga tgcatgacag tgcagagaat atactctctt cctgatcact cagggtcact    1200
catgattcat gcgcgaggtc ccaaaacagt gcctttgatg cagattctgt acatctctag    1260
acgattggtc caagggctga atgtgctctg gcccagtggt ccagtctgtc actatatgtc    1320
aacatcctga atatgaacat aacagtccaa catctcaaga gtgggcatga aaaggactca    1380
ttttgtgctt tttcctgtgg ttaacaagtc cttttttagcc tgggggaaca agcattaaca    1440
aaatgtttga agatctttgc cacgtaccat tccaaatttc tagggtaagt ctttagcttt    1500
tcagatcctg agtttctgca atgatcaaat gtgatttgga cagttgcgtt gactttctcc    1560
tggggctata atggagtgca aaggaaacaa tggcagggaa aatgcttgct ttcaaaatgg    1620
tagcatggat gtgttcattc gtgtagttac tgtattaggt atagccttc ctgaaactaa    1680 ctgaagtggg gttataaaaa cagtcccaat tttctatttc ctttgctgag acacaaagag    1740
gagacaaaag agcaaagctt gagggtagtt ttaccactgt gcttaagtgt tctgattttt    1800
ccagtgatca gggtgaaata aaaagcatag taagttccag ggcagtgaat accatacagg    1860
agacaagtta cagttttata atgtgttta ctttacacta aattctaaaa gtaaaatgtc    1920
tttttttttt tccgagacag agtttcactc ttgtagccca ggcaggagtg ctatggtgtg    1980
atctcggctc acagcaacct ccacctccca gtttcaagcg attcttctgc ctcagcctcc    2040
cgagaagttg aaattacagg tgcctggcac catatctcgc taattattct attttagta    2100 gagatcgggt tttaccatgt tggccaggct ggtctcgaac tcctgacttc aagtgatcca    2160
cccgcctcag cctcccaaag tgctgggatt acaggtgtga gtcactgtgc cggacctaac    2220
agtaaaatgt ctttcatgtg cttctcaagg caactacatt aaggaggaca catctcttaa    2280
tgtcattcta cagtagattt ctaatgctct ttcttggaag tttgttttc tgagaagagc    2340
```

```
taaaaatata ataacatgga agtgatcata ttatataatc aatgaagtgc tttcaaagga    2400
gataaaacta acctggtctg catttgcaac cagccttgat tgagagagag agaactcagg    2460
atacacttag agattttatt atggggaata gttactttat tcattttacc tcaatcaatg    2520
catgaaaata agtgacagtc attttcattt atcttttaat aaataaagtc accatgagga    2580
aaatgaaaac ccattaaagt cagtccttaa agatatttgg acatgcagac atgataacta    2640
acatttccat tcgtgagact tacccaaaac ctatacctca agtccatttc ttagaataca    2700
tgaaataaag atctcagtga gtgtataaaa ctgcacacca gaatcatatc cgtatagaca    2760
agaatacatc tactagaaaa atataaacca aaacaccaag gtgactctgt ttttttctgt    2820
tttaaaatat gttgtctttg tatgcatgtt tgcttcttcc ttttttttt taaacatcgc     2880 agataaaattc aactctcacc tcagttgaga gagaactgtc aatgtgactt ggcctctctc   2940
tttctagtcc cagaaagaat tgcactgaaa tgctgagctc ctgtaataaa aatgaccatt    3000
tgctgagagt aattaacata ctgaaagaga ttttcttaga atagtgcaca atggcccaat    3060
ggtgacatta tattgtctct ttataaatta ttttctatct atttctgtgg attatttcta    3120
caaagcactt ttcatatgtc caattccttt tattccccta caagtactga ctgactactg    3180
gctctgctgt tcactgatat gactttcggc aagttgcctg cacttttaa acgttatttc     3240 ctcattcaga acatggggcc atacaaaata caactcactt cagtgttatt ggggaattaa    3300
acaaataaat gcatgggaag catttaacat agtgcctgac acaataatga gcactcagta    3360
gatgttagct tttattaata ttgttgttgc tatgtccaga aacactatac ctccagaaaa    3420
tcatgggtac ttgctgggga cgttggggat atgcatgatt ttgaaaggag tgactgctct    3480
ttactgctca gatgagaaat ttttctaagc cagactcctt caaacatgta agattctgtt    3540
gtggattcta ggactgaaag aattcttggc cgagtgtggt ggcttatcct ggtaatctca    3600
tcatttggga ggacaaggca ggaagattgc ttgagcccag gagttggaaa caagcctgga    3660
caacatggcg aaaccctgtc tctacaaaaa atacaaacat tagctggtca tgggagtgag    3720
tgcctgtact cccagctact caggaggcta agataggagg atcacctgag cctgggcagt    3780
ttgaggtttc agtgagccgt gatgacacca tactatactc cactccagcc tgggtgacag    3840
tgacatcctg cctcaaaaaa acccccaaaa ttattctttt tgctgatttc atgtcagcag    3900
tgtgtgctga aggctgtaaa gtagccactt gttctgttta ttttccatt gaacaagtat     3960 ttatcaaaaa cgtactttgt ggaaggcact gtgctaggaa ctatgcatac agaaggaaaa    4020
ccaaatgttc ttggatacta cactccagtt gtgataaaaa agaaaaaagt attcttcaca    4080
aacttcaaca ttttgatgtg caaaaacata atatatgaat tagatctacc taactacaca    4140
gaattagacc aattatttct gggattatgg gctcatattt ttaataactg tcctcctacc    4200
tctctgttga caggttttat aaatattcat ttaattacac acagtcacag acacactcag    4260
acacacacac atacacacac acacacacct tgacaaataa tgggcatgaa caattgactg    4320
gtacttgctc tcattcttct agatgtcacc acagtggatc ccaaatacaa ttattcaaag    4380
gatgcaaatg gtaagttttt gtgttttttta tttcctcctg atcattttaa gttttgaact    4440
tctctggctt gaaaaatcag ggaatggatt ttgctaggtt ggatgctgca gaatggacct    4500
aatcatattt taaattagtc cctcttttc taggagttgt attaacaaac ctaactactg     4560
cttcatgtaa gagatgactg taaattgaag ggtacagtga tatgctttca gttatttcaa    4620
aaaacagact ttactcatcc atgtgtcttt tttctttct ttttttcttt ttttgagacg     4680
gagtctcgct ctgttgaaca ggctggattg cagtgacgcg atctcacctc actacaacct    4740
```

```
ccgcctctgg agttcaagcg attctccagc ctcagcttct caagtagctg ggactacagg    4800
cacatgccac catgtccggg tcatctttgt attttagca gagaccgggt ttcactatgt      4860
tggccaggct ggtctagaat tcctgacttc gtgatctgcc ccctcagccc tccgaagtgc    4920
tgggattaca gacgtgagtc actgtgcccg gcctaacagt aaaatgtctt tcatgcgctt    4980
ctcaaggcaa ctacgttaag gaggacactt ctcttaatgt cattctacag tagatttcta    5040
atgctctttc ttggaagttt gtttttctga gaaaagctaa aaatataaca tggaagtgat    5100
catattgtat aatcaatgaa gtgcttttca aggagataaa actaatctgg tccacgtttg    5160
caaccaacct tgattgagag agagagagaa ctcaggatac acttggagat tttattatgg    5220
ggaatagtta ctttattctt ttttcctcaa tcaattcatg gaaataagtg atagtcatat    5280
tcatttatct tttaataaat gaagtcacca tgaggaaaat aaaagacat tgaaaaccca    5340 ttaaagttag cccttaaaga tatttggaca tgcagacttg ataactaacg tttgcattct    5400
tgagacttac ccaaaaccca tacctcaagt ccatgttttt agaattcatg aaataaagat    5460
ctcagtgagt gcataaaatt gcgcaccaga atcatatccg tatagacaag aacacatcta    5520
ctagaaaaat aataaaccaa cacaccaatg caactgtgtt ttcttctgtt ttaaaatatg    5580
ttgtctttgt atgcatgttt gcttcttcct ttttttttt taacatcaca gataaattca    5640
actctcacct caggttttat tgagagaact gtcaatgtga cttggcctct gtctttctag    5700
tcccagaaag aatcgcactg aaatgctgag ctcctgtaat aaaaatgacc atttgctgag    5760
agtaattaac atactgaaag agattttctt agagtacaca atggtgacat tatattgtct    5820
ctttataaat aactttctat ctatttctgt ggattattcc tacaaagtac ttttcatatg    5880
tccagtttct tttcttcccc tacaactacc gtctgaatac tggctctgct atttgctgat    5940
atgattctcg gcaagttgcc tgcactttt aaactttatt tcctcattca gaacatgggg    6000
ccatgtaata ctcatgtacg tgagtattac gtaataatgc tcacttaagt gttactgggg    6060
aattaaacaa aaaatgcat ggcaagcatt taacatagtg cctgacacaa taatgagcac    6120
tcagtagatg ttagatttta ttaatattgt tgttgttatg tccggaaaca ctatacctcc    6180
agaaaatcat gggtacttgc ttgggatgtt ggggatatgc atgatttgga aaggtatgac    6240
tgcttttttc tgcttagatg agaaattttt ctaagccaga ctccttcaaa tatgtaagat    6300
tctgttgtgg attctaggac ggaaagaatt cttggtcagg tgtggtttct tatccctgta    6360
atcccagaat tttgggagga caaggcagga agattgcttg agcccaggag tttgaaacca    6420
gcctgggcaa caagacgaaa ccctgtctct acaaagtac ataaattagc ttggcttggt    6480
ggtgtgtgcc tgtattacca gctattcggg agactgagat gggaggatct cctgaacctg    6540
tgaagtttga ggcttcagtg agccgtgatg acaccatact atactcgact ccagcctgtg    6600
cgacagtgag actctgcgtc aaaaaaaaa ccccaaaatt attgtttttg ctgatttcag    6660
gtcagcagtg tgtgctgaag ggtgtaaagt agccacttga tcagtttatt tttccactga    6720
acaagtattt atcaaaaaca tactttgtgg tctgttttg ataaataaaa aggcactgtg    6780
ctaggagcca tgaatacaga aggaaaacca aatgttcttg gatactacac tccagttgtg    6840
ataaaaaaga aaaatgtatt cttcacgaac ttcaacattt tgatatgcaa aaacatagta    6900
tataaattag atctacctga ttacgtagaa tcagaccaat tatttctgga attgagggct    6960
catattttta ataactgtcc tcctgcctct ctgttgacag gttttataaa tattcattta    7020
attacacaca cacacacaca caccttgaca aataatggac atgaacaatt gactagtact    7080
```

```
tgctctcatt cttctagatg tcatcacaat ggatcccaaa gacaattggt caaaagatgc    7140
aaatggtaag cttttgtgtt tttcctttcc tcctgatcat tttaagtttt gaacttctct    7200
ggcttgaaaa atcagggaat gggccgggtg cggtggctca cgcctgtaat cccagcactt    7260
tgggaggccg aggcgggcgg atcacgaggt caggagatcg agaccatccc ggctaaaacg    7320
gtgaaacccc gtctctacta aaaatacaaa aaattagccg ggcttagtgg cgggcgcctg    7380
tagtcccagc tacttgggag gctgaggcag gagaatggcg tgaacccggg aggcggagct    7440
tgcagtgagc cgagattgcg ccactgcact ccactccagc ctgggcgaca gagcgagact    7500
ccgtctcaaa aaaaaaaaa aaaaaaaaa aagaaaaatc agggaatgga ttttgctagg    7560
ttggatgctg cagaatggac ctagtgatat tttaaattag tccctctttt tctaggagtt    7620
gtattaacaa acctaactac tgcttcgggt atgagatgac tgtaaattag agggtacagt    7680
gatatgcttt cagttatttc aaaaaacaga ctttattcat ccgtctgtct ttttttttt    7740 ttttttttt tttttttgag acggaggagt ctcactctat cacccaggct ggagtgcagt    7800
ggcgcgatct cggctcacca taacctccgc cttactggtt caagcgattc tccagcctca    7860
gcttctcaag tagctgggac tacaggtgca caccaccata cctggctaat ttttgtattt    7920
ttaatagaga tggggtttca ccacgctggc caggatggtc ttgaattctt gacctcgtga    7980
tctgccccct cgggctccca aacttctggg attataggcg tgagccactg tgcccggcct    8040
tctgtctttt gttataatga ctggggaaaa catgatacca tgttgcttct tgagttgttt    8100
tgttttagtc tttggtcttt gctagtagct aataacacga actagtgttt atcaagtgct    8160
ttttacacag aagggcttgt tctgcatttt ctagtttaat catcttaata ctcctataaa    8220
gtagtacaat atattttctc ccattttaca gtcccttta agtaaataac tataaaaatc    8280
ccttatacat gtcacacagc taggtctggc atttcaaatc aggacatcaa acaaagaatt    8340
cgtgcagtta ctaagtcctc tattttttct acaatagaaa aaatagcaag aattacagat    8400
agcaagacat tacaaggcag gaatctgaaa cgaaagggac ataatgtggg gctgggtggg    8460
tgcatgagct ttgcagacta gactttcatt ccagctcttt taatgattag gtgtaagtga    8520
cctacatttt gtgagtaaca gttttctcat cagccaacta agaataatta caccagattc    8580
acagttattg aagagataag ggcatgaatg tgagatgtct ggcgtagggt atctcattta    8640
gcagacacag aatgaatact tgtttctggc ttttctctc tacatatgca caaagaatgt    8700
gactagaagc attggctcta gccctgctca actttcctct atttccaata ccaaggggct    8760
ctgacttagg ctgccacacc aggcaaggag gggcagtacc acctcacttg accaagggca    8820
gggagtcacg gacacatcac ttcctgagat ccttttccac accaaggact gatgtttctg    8880
gaattctcac tttatgaaga caaaacatat aaatggaaat ttctgcagga agagactcac    8940
tcttgtagct cattgagtag gcactagtgg tccacccca ctgtctttac ttattccttg    9000
acatcacata tctcttgtaa aacctcaaat aatgttaaat gcaatcaccc aataatagca    9060
tagccataat tagaggcatt taggaaagac aggtgagtgt gccacaacta cctaacacat    9120
cagcaaatct ggattaacca ctttctttga ttttccacaa tgcaacctta cttttaata    9180 gttgggaatg ttctaagtga atttagcaga ggttgttaat caacttgaaa gctgaattct    9240
gacttgtctg actcttggtg gtgctggtag cagtagatgt ttacttttag gttttggtgg    9300
tggtggaata tcacttcaac gtaaatcatc agaaataagt atttgtgaac ccctctcgca    9360
ttaatatatc ttattctgta aaagaacat gtgcaatttc tcttagatac actactgctg    9420
cagctcacaa acacctctgc atattacacg tacctcctcc tgctcctcaa gagtgtggtc    9480
```

```
tattttgcca tcatcacctg ctgtctgctt agaagaacgg ctttctgctg caatggagag    9540
aaatcataa                                                            9549
```

<210> SEQ ID NO 34
<211> LENGTH: 182
<212> TYPE: PRT
<213> ORGANISM: Homo sapiens

<400> SEQUENCE: 34

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
            35                  40                  45

Glu Ala Lys Asn Ile Thr Trp Phe Lys Asp Gly Lys Met Ile Gly Phe
        50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

<210> SEQ ID NO 35
<211> LENGTH: 171
<212> TYPE: PRT
<213> ORGANISM: Homo sapiens

<400> SEQUENCE: 35

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
```

```
                115                 120                 125
Glu Thr Gly Arg Leu Ser Gly Ala Ala Asp Thr Gln Ala Leu Leu Arg
            130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 36
<211> LENGTH: 127
<212> TYPE: PRT
<213> ORGANISM: Homo sapiens

<400> SEQUENCE: 36

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys
        115                 120                 125

<210> SEQ ID NO 37
<211> LENGTH: 207
<212> TYPE: PRT
<213> ORGANISM: Homo sapiens

<400> SEQUENCE: 37

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
```

```
                145                 150                 155                 160
Pro Val Thr Arg Gly Ala Gly Gly Arg Gln Arg Gly Gln Asn
                    165                 170                 175
Lys Glu Arg Pro Pro Val Pro Asn Pro Asp Tyr Glu Pro Ile Arg
                    180                 185                 190
Lys Gly Gln Arg Asp Leu Tyr Ser Gly Leu Asn Gln Arg Ile
                    195                 200                 205
```

<210> SEQ ID NO 38
<211> LENGTH: 140
<212> TYPE: PRT
<213> ORGANISM: Homo sapiens

<400> SEQUENCE: 38

```
Ile Gln Asn Pro Asp Pro Ala Val Tyr Gln Leu Arg Asp Ser Lys Ser
1               5                   10                  15
Ser Asp Lys Ser Val Cys Leu Phe Thr Asp Phe Asp Ser Gln Thr Asn
                20                  25                  30
Val Ser Gln Ser Lys Asp Ser Asp Val Tyr Ile Thr Asp Lys Thr Val
            35                  40                  45
Leu Asp Met Arg Ser Met Asp Phe Lys Ser Asn Ser Ala Val Ala Trp
    50                  55                  60
Ser Asn Lys Ser Asp Phe Ala Cys Ala Asn Ala Phe Asn Asn Ser Ile
65                  70                  75                  80
Ile Pro Glu Asp Thr Phe Phe Pro Ser Pro Glu Ser Ser Cys Asp Val
                85                  90                  95
Lys Leu Val Glu Lys Ser Phe Glu Thr Asp Thr Asn Leu Asn Phe Gln
            100                 105                 110
Asn Leu Ser Val Ile Gly Phe Arg Ile Leu Leu Leu Lys Val Ala Gly
        115                 120                 125
Phe Asn Leu Leu Met Thr Leu Arg Leu Trp Ser Ser
    130                 135                 140
```

<210> SEQ ID NO 39
<211> LENGTH: 178
<212> TYPE: PRT
<213> ORGANISM: Homo sapiens

<400> SEQUENCE: 39

```
Asp Leu Lys Asn Val Phe Pro Pro Glu Val Ala Val Phe Glu Pro Ser
1               5                   10                  15
Glu Ala Glu Ile Ser His Thr Gln Lys Ala Thr Leu Val Cys Leu Ala
                20                  25                  30
Thr Gly Phe Tyr Pro Asp His Val Glu Leu Ser Trp Trp Val Asn Gly
            35                  40                  45
Lys Glu Val His Ser Gly Val Ser Thr Asp Pro Gln Pro Leu Lys Glu
    50                  55                  60
Gln Pro Ala Leu Asn Asp Ser Arg Tyr Cys Leu Ser Ser Arg Leu Arg
65                  70                  75                  80
Val Ser Ala Thr Phe Trp Gln Asn Pro Arg Asn His Phe Arg Cys Gln
                85                  90                  95
Val Gln Phe Tyr Gly Leu Ser Glu Asn Asp Glu Trp Thr Gln Asp Arg
            100                 105                 110
Ala Lys Pro Val Thr Gln Ile Val Ser Ala Glu Ala Trp Gly Arg Ala
        115                 120                 125
Asp Cys Gly Phe Thr Ser Glu Ser Tyr Gln Gln Gly Val Leu Ser Ala
```

```
            130                 135                 140
Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 40
<211> LENGTH: 176
<212> TYPE: PRT
<213> ORGANISM: Homo sapiens

<400> SEQUENCE: 40

Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
                20                  25                  30

Thr Gly Phe Phe Pro Asp His Val Glu Leu Ser Trp Trp Val Asn Gly
            35                  40                  45

Lys Glu Val His Ser Gly Val Ser Thr Asp Pro Gln Pro Leu Lys Glu
        50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175

<210> SEQ ID NO 41
<211> LENGTH: 153
<212> TYPE: PRT
<213> ORGANISM: Homo sapiens

<400> SEQUENCE: 41

Ser Gln Pro His Thr Lys Pro Ser Val Phe Val Met Lys Asn Gly Thr
1               5                   10                  15

Asn Val Ala Cys Leu Val Lys Glu Phe Tyr Pro Lys Asp Ile Arg Ile
                20                  25                  30

Asn Leu Val Ser Ser Lys Lys Ile Thr Glu Phe Asp Pro Ala Ile Val
            35                  40                  45

Ile Ser Pro Ser Gly Lys Tyr Asn Ala Val Lys Leu Gly Lys Tyr Glu
        50                  55                  60

Asp Ser Asn Ser Val Thr Cys Ser Val Gln His Asp Asn Lys Thr Val
65                  70                  75                  80

His Ser Thr Asp Phe Glu Val Lys Thr Asp Ser Thr Asp His Val Lys
                85                  90                  95

Pro Lys Glu Thr Glu Asn Thr Lys Gln Pro Ser Lys Ser Cys His Lys
            100                 105                 110
```

```
Pro Lys Ala Ile Val His Thr Glu Lys Val Asn Met Met Ser Leu Thr
        115                 120                 125

Val Leu Gly Leu Arg Met Leu Phe Ala Lys Thr Val Ala Val Asn Phe
130                 135                 140

Leu Leu Thr Ala Lys Leu Phe Phe Leu
145                 150

<210> SEQ ID NO 42
<211> LENGTH: 173
<212> TYPE: PRT
<213> ORGANISM: Homo sapiens

<400> SEQUENCE: 42

Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Val Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Lys
65                  70                  75                  80

Ser Leu Asp Lys Glu His Arg Cys Ile Val Arg His Glu Asn Asn Lys
                85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170

<210> SEQ ID NO 43
<211> LENGTH: 189
<212> TYPE: PRT
<213> ORGANISM: Homo sapiens

<400> SEQUENCE: 43

Asp Lys Gln Leu Asp Ala Asp Val Ser Pro Lys Pro Thr Ile Phe Leu
1               5                   10                  15

Pro Ser Ile Ala Glu Thr Lys Leu Gln Lys Ala Gly Thr Tyr Leu Cys
            20                  25                  30

Leu Leu Glu Lys Phe Phe Pro Asp Ile Ile Lys Ile His Trp Gln Glu
        35                  40                  45

Lys Lys Ser Asn Thr Ile Leu Gly Ser Gln Glu Gly Asn Thr Met Lys
    50                  55                  60

Thr Asn Asp Thr Tyr Met Lys Phe Ser Trp Leu Thr Val Pro Glu Glu
65                  70                  75                  80

Ser Leu Asp Lys Glu His Arg Cys Ile Val Arg His Glu Asn Asn Lys
                85                  90                  95

Asn Gly Ile Asp Gln Glu Ile Ile Phe Pro Pro Ile Lys Thr Asp Val
            100                 105                 110
```

```
Thr Thr Val Asp Pro Lys Tyr Asn Tyr Ser Lys Asp Ala Asn Asp Val
        115                 120                 125

Ile Thr Met Asp Pro Lys Asp Asn Trp Ser Lys Asp Ala Asn Asp Thr
    130                 135                 140

Leu Leu Leu Gln Leu Thr Asn Thr Ser Ala Tyr Tyr Thr Tyr Leu Leu
145                 150                 155                 160

Leu Leu Leu Lys Ser Val Val Tyr Phe Ala Ile Ile Thr Cys Cys Leu
                165                 170                 175

Leu Arg Arg Thr Ala Phe Cys Cys Asn Gly Glu Lys Ser
                180                 185

<210> SEQ ID NO 44
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
                100                 105                 110

Gly Gln Gly Thr Thr Val Thr Val
            115                 120

<210> SEQ ID NO 45
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Pro Leu Ile
            35                  40                  45

Tyr Ser Ala Thr Tyr Arg Asn Ser Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95
```

```
Thr Ser Gly Gly Gly Thr Lys Leu Glu Ile Lys Arg
            100                 105

<210> SEQ ID NO 46
<211> LENGTH: 16
<212> TYPE: PRT
<213> ORGANISM: Homo sapiens

<400> SEQUENCE: 46

Met Lys Trp Val Thr Phe Ile Ser Leu Leu Phe Ser Ser Ala Tyr Ser
1               5                   10                  15

<210> SEQ ID NO 47
<211> LENGTH: 30
<212> TYPE: PRT
<213> ORGANISM: Homo sapiens

<400> SEQUENCE: 47

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Gly Ser Gly Gly Gly Gly Ser Gly Gly Gly Gly Ser
1               5                   10                  15
```